United States Patent
Madden et al.

(10) Patent No.: US 10,401,241 B2
(45) Date of Patent: Sep. 3, 2019

(54) SURFACE SENSOR ARRAYS USING IONICALLY CONDUCTING MATERIAL

(71) Applicant: The University of British Columbia, Vancouver (CA)

(72) Inventors: John Madden, Vancouver (CA); Yuta Dobashi, Vancouver (CA); Mirza Saquib Sarwar, Vancouver (CA)

(73) Assignee: The University of British Columbia, Vancouver (CA)

(*) Notice: Subject to any disclaimer, the term of this patent is extended or adjusted under 35 U.S.C. 154(b) by 52 days.

(21) Appl. No.: 15/618,113

(22) Filed: Jun. 8, 2017

(65) Prior Publication Data
US 2017/0356815 A1    Dec. 14, 2017

Related U.S. Application Data

(60) Provisional application No. 62/347,601, filed on Jun. 8, 2016.

(51) Int. Cl.
    *G01L 1/00*    (2006.01)
    *G01L 5/00*    (2006.01)
    (Continued)

(52) U.S. Cl.
    CPC .......... *G01L 1/2287* (2013.01); *A61B 5/0205* (2013.01); *A61B 5/6804* (2013.01);
    (Continued)

(58) Field of Classification Search
    CPC ... G01L 1/00; G01L 1/14; G01L 1/146; G01L 1/16; G01L 1/18; G01L 1/205;
    (Continued)

(56) References Cited

U.S. PATENT DOCUMENTS

| 4,574,438 A | 3/1986 | Diepers et al. |
| 6,543,299 B2 | 4/2003 | Taylor |

(Continued)

FOREIGN PATENT DOCUMENTS

| WO | 2009144615 A1 | 12/2009 |
| WO | 2014169119 A1 | 10/2014 |

(Continued)

OTHER PUBLICATIONS

Sarwar et al., Transparent and Conformal 'Piezoionic' Touch Sensor. In Y. Bar-Cohen (Eds.), Proceedings of SPIE: Electroactive Polymer Actuators and Devices (EAPAD) 2015 (pp. 943026-1-943026-9). United States: S P I E—International Society for Optical Engineering.

(Continued)

*Primary Examiner* — Nguyen Q. Ha
(74) *Attorney, Agent, or Firm* — Todd A. Rattray, Oyen Wiggs Green & Mutala LLP

(57) ABSTRACT

Sensor arrays are provided for sensing pressure and/or moisture over a two-dimensional sensing surface. The sensor arrays comprise ionically conductive materials. Individual sensor elements in the sensor arrays may comprise piezoionic ionically conductive materials, piezoresistive ionically conductive materials and/or capacitive sensor elements having electrodes fabricated from ionically conductive materials. Two-dimensional pressure maps and/or moisture maps of the sensing surface may be obtained by implementing methods comprising scanning over individual sensor elements in the sensor arrays.

31 Claims, 21 Drawing Sheets

(51) Int. Cl.

| | | |
|---|---|---|
| *G01L 1/22* | (2006.01) | |
| *A61B 5/0205* | (2006.01) | |
| *A61B 5/00* | (2006.01) | |
| *G01L 1/20* | (2006.01) | |
| *G06F 3/041* | (2006.01) | |
| *G01L 1/14* | (2006.01) | |
| *A61B 5/024* | (2006.01) | |
| *A61B 5/08* | (2006.01) | |
| *A61B 5/0476* | (2006.01) | |
| *A61B 5/16* | (2006.01) | |

(52) U.S. Cl.
CPC .......... *A61B 5/6843* (2013.01); *A61B 5/6892* (2013.01); *G01L 1/146* (2013.01); *G01L 1/205* (2013.01); *G06F 3/0414* (2013.01); *G06F 3/0416* (2013.01); *A61B 5/024* (2013.01); *A61B 5/0476* (2013.01); *A61B 5/0816* (2013.01); *A61B 5/165* (2013.01); *A61B 5/6823* (2013.01); *A61B 5/6833* (2013.01); *A61B 5/6898* (2013.01); *A61B 2562/0247* (2013.01); *A61B 2562/046* (2013.01)

(58) Field of Classification Search
CPC ......... G01L 1/2287; G01L 5/00; G06F 3/041; G06F 3/0414; G06F 3/0416; A61B 5/024; A61B 5/0205; A61B 5/0476; A61B 5/0816; A61B 5/165; A61B 5/6804; A61B 5/6823; A61B 5/6833; A61B 5/6843; A61B 5/6892; A61B 5/6898; A61B 2562/0247; A61B 2562/046
See application file for complete search history.

(56) References Cited

U.S. PATENT DOCUMENTS

| | | |
|---|---|---|
| 8,726,908 B2 | 5/2014 | Squitieri |
| 8,757,165 B2 | 6/2014 | Squitieri |
| 2005/0124864 A1 | 6/2005 | Mack et al. |
| 2008/0054875 A1* | 3/2008 | Saito .................. A61B 5/1172 324/71.5 |
| 2008/0208063 A1 | 8/2008 | Brauers et al. |
| 2012/0277637 A1 | 11/2012 | Vahdatpour et al. |
| 2013/0106244 A1* | 5/2013 | Liu ...................... H01L 41/1132 310/338 |
| 2014/0152621 A1* | 6/2014 | Okayama .............. G06F 3/0416 345/174 |
| 2014/0174189 A1* | 6/2014 | Pan ........................ G01L 9/0072 73/724 |
| 2014/0327843 A1* | 11/2014 | Liu ...................... G02F 1/13338 349/12 |
| 2016/0258829 A1* | 9/2016 | Celik-Butler ........... H01L 41/37 |
| 2016/0365198 A1* | 12/2016 | Pan ......................... G01L 1/02 |
| 2017/0059426 A1* | 3/2017 | Choi ........................ G01L 5/00 |
| 2017/0059434 A1* | 3/2017 | Li .......................... G01L 9/0072 |
| 2017/0139527 A1* | 5/2017 | Nathan ................. G06F 3/0418 |
| 2017/0224280 A1* | 8/2017 | Bozkurt ................. G01L 5/0014 |
| 2018/0038745 A1* | 2/2018 | Madden .................. G01L 11/00 |
| 2018/0095582 A1* | 4/2018 | Hwang ................ G06F 3/0412 |
| 2018/0246589 A1* | 8/2018 | So .......................... G06F 3/016 |

FOREIGN PATENT DOCUMENTS

| | | |
|---|---|---|
| WO | 2016086306 A1 | 6/2016 |
| WO | 2016141468 A1 | 9/2016 |

OTHER PUBLICATIONS

Dobashi et al., Mechanoionic Transduction of Solid Polymer Electrolytes and Potential Applications—VER11, Biomaterials and Soft Materials, vol. 1, Issue 1, pp. 63-68, Jan. 26, 2016.
Liu et al., Self-Powered Piezoionic Strain Sensor Toward the Monitoring of Human Activities, Small 12 (36), 5074-5080, May 6, 2016.
Print-out of www.boditrak.com on May 23, 2015. Accessed on www.web.archive.org.
Print-out of www.themapsystem.com on Nov. 17, 2015. Accessed on www.web.archive.org.
Print-out of www.tekscan.com/product-group/medical/bedding-seating on Apr. 12, 2015. Accessed on www.web.archive.org.
United Nations Department of Economic and Social Affairs. "World Population Ageing 2013". United Nations, 2013. http://www.un.org/en/development/desa/poplulation/publications/pdf/ageing.
Brown, Brandon R. "Temperature Response in Electrosensors and Thermal Voltages in Electrolytes." Journal of Biological Physics 36.2 (2010): 121-134.

* cited by examiner

SURFACE SENSOR ARRAYS USING IONICALLY CONDUCTING MATERIAL

RELATED APPLICATIONS

This application claims priority from, and the benefit of 35 USC 119(e) in relation to, U.S. application No. 62/347,601 filed 8 Jun. 2016, which is hereby incorporated herein by reference in its entirety.

TECHNICAL FIELD

The invention relates to pressure sensors incorporating ionically conductive materials used for a variety of applications. Particular embodiments provide surface sensor arrays comprising pluralities of sensors arranged in various topologies over the surface (or a working region corresponding to the surface) for detecting pressure (e.g. providing a pressure map) over the surface.

BACKGROUND

Pressure sensing, such as touch sensing, has applications in various fields and industries. For example, touch sensors (an example of a type of pressure sensor) have been used in electronic devices, such as display or input devices and wearable or implantable electronic devices, and have applications in medical or healthcare industries. Touch sensors are tactile sensors and acquire information through physical touch with another object, such as a human finger. Existing touch sensors include capacitive, piezo-resistive, piezoelectric, inductive or optoelectronic sensors. Typically, these touch sensors require additional energy input, such as by way of an electrical signal applied to the sensor, to detect the touch. There is a desire to develop new or improved pressure sensors, including, by way of non-limiting example, touch sensors.

There is a general desire to provide pressure sensors for detecting characteristics (e.g. the presence, location and/or magnitude) of pressure applied to a two-dimensional sensing surface.

Moisture sensing has applications in various fields and industries. By way of non-limiting example, moisture sensors may be used in medical applications (e.g. to detect bodily fluids), in water management applications (e.g. to detect leakage), in building systems such as HVAC systems (e.g. to detect condensation and/or leakage) and/or the like. There is a general desire to provide moisture sensors for detecting characteristics (e.g. the presence, location and/or magnitude) of moisture on a two-dimensional sensing surface.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

The invention has a number of non-limiting aspects. Non-limiting aspects of the invention provide the following:

1. A flexible sensor array for detecting pressure at one or more locations over a sensing surface, the sensor array comprising:
a first plurality of conductive electrodes distributed over a working region adjacent the sensing surface, each of the first plurality of electrodes elongated in an x-direction that is generally tangential to the sensing surface and a second plurality of conductive electrodes distributed over the working region, each of the second plurality of electrodes elongated in a y-direction, the y-direction generally tangential to the sensing surface and non-parallel with the x-direction;
each of the first plurality of electrodes overlapping each of the second plurality of electrodes in a z-direction generally normal to the sensing surface at a corresponding overlap region;
for each overlap region between one of the first plurality of electrodes and one of the second plurality of electrodes, a corresponding region of piezoionic polymer interposed between, and in conductive contact with, the one of the first plurality of electrodes and the one of the second plurality of electrodes in the z-direction, wherein the corresponding region of piezoionic polymer exhibits ionic conductivity which generates a corresponding first electrical signal at the one of the first plurality of electrodes relative to a first electrical signal reference and a corresponding second electrical signal at the one of the second plurality of electrodes relative to a second electrical signal reference, the first and second corresponding electrical signals depending on a state of deformation of the corresponding region of piezoionic polymer.

2. A sensor array according to aspect 1 or any other aspect herein wherein the piezoionic polymer comprises a contiguous layer of piezoionic polymer interposed between the first plurality of electrodes and the second plurality of electrodes in the z-direction and each corresponding region of piezoionic polymer is part of the contiguous layer.

3. A sensor array according to aspect 1 or any other aspect herein wherein the first electrical signal reference is associated with one of the first plurality of electrodes assigned to be a reference electrode.

4. A sensor array according to any one of aspects 1 to 3 or any other aspect herein wherein, for each overlap region between one of the first plurality of electrodes and one of the second plurality of electrodes, the corresponding electrical signal at the one of the first plurality of electrodes relative to the first electrical signal reference comprises a voltage difference between the one of the first plurality of electrodes and the first electrical signal reference, the voltage difference depending on the state of deformation of the corresponding region of piezoionic polymer.

5. A sensor array according to any one of aspects 1 to 4 or any other aspect herein wherein, for each overlap region between one of the first plurality of electrodes and one of the second plurality of electrodes, the corresponding electrical signal at the one of the first plurality of electrodes relative to the first electrical signal reference comprises a current flow between the one of the first plurality of electrodes and the first electrical signal reference, the current flow depending on the state of deformation of the corresponding region of piezoionic polymer.

6. A sensor array according to aspect 4 or any other aspect herein wherein, for each overlap region between one of the first plurality of electrodes and one of the second plurality of electrodes, the first electrical signal reference is another one of the first plurality of electrodes.
7. A sensor array according to aspect 6 or any other aspect herein wherein the another one of the first plurality of electrodes is common for a least a sub-plurality of the first plurality of electrodes.
8. A sensor array according to aspect 4 or any other aspect herein wherein, for each overlap region between one of the first plurality of electrodes and one of the second plurality of electrodes, the first electrical signal reference is an adjacent one of the first plurality of electrodes.
9. A sensor array according to aspect 4 or any other aspect herein wherein, for each overlap region between one of the first plurality of electrodes and one of the second plurality of electrodes, the first electrical signal reference is a reference one of the second plurality of electrodes.
10. A sensor array according to aspect 4 or any other aspect herein wherein, for each overlap region between one of the first plurality of electrodes and one of the second plurality of electrodes, the first electrical signal reference is the one of the second plurality of electrodes.
11. A sensor array according to any one of aspects 1 to 10 or any other aspect herein comprising a sensing circuit connectable to amplify the first electrical signal for each overlap region and one or more multiplexers for connecting, for each overlap region, the one of the first plurality of electrodes and the first electrical signal reference to inputs of the sensing circuit to thereby cause the sensing circuit to amplify the first electrical signal.
12. A sensor array according to aspect 11 or any other aspect herein comprising a controller connected to provide control signals to the one or more multiplexers and configured to output control signals which control the one or more multiplexers to iteratively scan over the overlap regions in the working region and, for each overlap region, to effect the connections of the one of the first plurality of electrodes and the first electrical signal reference to the inputs of the sensing circuit.
13. A sensor array according to aspect 12 or any other aspect herein wherein, for each overlap region, the controller is configured to determine a pressure estimate for the overlap region based at least in part on the first electrical signal.
14. A sensor array according to any one of aspects 12 to 13 or any other aspect herein wherein the controller is configured to effect an iteration of a scan over the overlap regions in the working region with a frequency in a range of 10 Hz-20 Hz.
15. A sensor array according to any one of aspects 1 to 14 or any other aspect herein wherein the sensing surface comprises a surface of a bed.
16. A sensor array according to aspect 15 or any other aspect herein wherein the sensor array is used to estimate one or more of heart rate, respiratory rate, body configuration and location of a person atop the bed.
17. A sensor array according to any one of aspects 15 to 16 or any other aspect herein wherein the sensor array is used to estimate body configuration and location of a person atop the bed and is used to trigger one or more actuators to provide tactile stimulus to the patient in the hospital bed, the triggering of the one or more actuators based at least in part on the estimated body configuration and location.
18. A sensor array according to any one of aspects 1 to 14 or any other aspect herein wherein the sensing surface comprises a surface of a chair and the sensor array detects pressure associated with a person sitting in the chair.
19. A sensor array according to any one of aspects 1 to 14 or any other aspect herein used in a garment wearable by a human and the sensing surface is a surface of the garment in contact with the human.
20. A sensor array according to aspect 19 or any other aspect herein wherein the sensing surface is adhesively bonded into contact with the human.
21. A sensor array according to aspect 19 or any other aspect herein wherein the garment is elastically deformable, is deformably expanded and permitted to restore at least partially to provide contact between the surface and the human.
22. A sensor array according to any one of aspect 12 to 13 or any other aspect herein wherein the controller is configured to effect a scan iteration over the overlap regions in the working region with a frequency in a range of 60 Hz-120 Hz.
23. A sensor array according to any one of aspects 1 to 13 and 22 or any other aspect herein wherein the sensing surface comprises a surface of an electronic device and the sensor array detects pressure associated with a person interacting with the electronic device.
24. A sensor array according to any one of aspects 1 to 23 or any other aspect herein wherein the sensor array is in force-transmitting contact with the sensing surface.
25. A sensor array according to any one of aspects 1 to 24 or any other aspect herein wherein the sensing surface is non-planar.
26. A sensor array according to any one of aspects 1 to 25 or any other aspect herein wherein the first plurality of electrodes and second plurality of electrodes are substantially transparent at visible light wavelengths.
27. A sensor array according to any one of aspects 1 to 26 or any other aspect herein wherein each electrode of the first and second pluralities of electrodes have transmissivities of over 90% at visible light wavelengths.
28. A sensor array according to any one of aspects 1 to 27 or any other aspect herein wherein at least one electrode of the first and second pluralities of electrodes is elastically deformable
29. A sensor array according to any one of aspects 1 to 28 or any other aspect herein wherein at least one of the first and second pluralities of electrodes is fabricated from at least one of: a metal mesh; silver nanowires, carbon nanotubes and one or more conducting polymers.
30. A sensor array according to any one of aspects 1 to 29 or any other aspect herein wherein each electrode of the first and second pluralities of electrodes is fabricated from ionically conductive hydrogel.
31. A method for generating a pressure map of a sensing surface comprising:
providing a flexible sensor array comprising:
a first plurality of conductive electrodes distributed over a working region adjacent the sensing surface, each of the first plurality of electrodes elongated in an x-direction that is generally tangential to the sensing surface and a second plurality of conductive electrodes distributed over the working region, each of the second plurality of electrodes elongated in a y-direction, the y-direction generally tangential to the sensing surface and non-parallel with the x-direction;

each of the first plurality of electrodes overlapping each of the second plurality of electrodes in a z-direction generally normal to the sensing surface at a corresponding overlap region;

for each overlap region between one of the first plurality of electrodes and one of the second plurality of electrodes, a corresponding region of piezoionic polymer interposed between, and in conductive contact with, the one of the first plurality of electrodes and the one of the second plurality of electrodes in the z-direction;

for each overlap region:

detecting at least one electrical signal wherein the at least one electrical signal depends on a state of deformation of the corresponding region of piezoionic polymer; and estimating a pressure value for the overlap region based at least in part on the at least one electrical signal.

32. A method according to aspect 31 or any other aspect herein wherein, for each overlap region, detecting the at least one electrical signal comprises detecting a voltage difference between the one of the first plurality of electrodes and the one of the second plurality of electrodes.

33. A method according to aspect 31 or any other aspect herein wherein, for each overlap region, detecting the at least one electrical signal comprises detecting a current flow between the one of the first plurality of electrodes and the one of the second plurality of electrodes.

34. A method according to any one of aspects 31 to 33 or any other aspect herein comprising, for each overlap region, estimating a corresponding pressure based on an empirically determined relationship between the at least one electrical signal and the corresponding pressure.

35. A method according to aspect 34 or any other aspect herein wherein the empirically determined relationship is based at least in part on one or more of: a relationship between the at least one electrical signal and a difference in radius of curvature between a surface of the corresponding region of piezoionic polymer in contact with the one of the first plurality of electrodes and an opposing surface of the corresponding region of piezoionic polymer in contact with the one of the second plurality of electrodes; a relationship between the difference in radius of curvature and a strain of the corresponding region of piezoionic polymer; a relationship between the strain of the corresponding region of piezoelectric polymer and the stress on the corresponding region of piezoelectric polymer; and a relationship between the stress of the corresponding region of piezoelectric polymer and the pressure on the corresponding region of piezoelectric polymer.

36. A method according to any one of aspects 31 to 35 or any other aspect herein wherein, for each overlap region, estimating a pressure value for the overlap region based at least in part on the at least one electrical signal comprises subjecting the at least one electrical signal to a thresholding process and, if the at least one electrical signal is less than a threshold, setting the pressure value for the overlap region to be equal to a reference pressure.

37. A method according to aspect 36 or any other aspect herein wherein setting the pressure value for the overlap region to be equal to a reference pressure comprises setting the pressure value for the overlap region to be equal to atmospheric pressure.

38. A method according to aspect 31 or any other aspect herein wherein, for each overlap region, detecting the at least one electrical signal comprises:

detecting a first electrical signal at the one of the first plurality of electrodes relative to a first electrical signal reference; and detecting a second electrical signal at the one of the second plurality of electrodes relative to a second electrical signal reference;

wherein the first and second electrical signals depend on a state of deformation of the corresponding region of piezoionic polymer.

39. A method according to aspect 38 or any other aspect herein wherein, for each overlap region, detecting the first electrical signal comprises at least one of: detecting a voltage difference between the one of the first plurality of electrodes and the first electrical signal reference; and detecting a current flow between the one of the first plurality of electrodes and the first electrical signal reference.

40. A method according to any one of aspects 31 to 39 or any other aspect herein comprising any of the features, combinations of features and/or sub-combinations of features of any one or aspects 2 to 30.

41. A method for generating a pressure map of a sensing surface comprising:

providing a flexible sensor array comprising:

a first plurality of conductive electrodes distributed over a working region adjacent the sensing surface, each of the first plurality of electrodes elongated in an x-direction that is generally tangential to the sensing surface and a second plurality of conductive electrodes distributed over the working region, each of the second plurality of electrodes elongated in a y-direction, the y-direction generally tangential to the sensing surface and non-parallel with the x-direction;

each of the first plurality of electrodes overlapping each of the second plurality of electrodes in a z-direction generally normal to the sensing surface at a corresponding overlap region;

for each overlap region between one of the first plurality of electrodes and one of the second plurality of electrodes, a corresponding region of piezoionic polymer interposed between, and in conductive contact with, the one of the first plurality of electrodes and the one of the second plurality of electrodes in the z-direction;

for each one of the first plurality of electrodes detecting a first electrical signal at the one of the first plurality of electrodes relative to a first electrical signal reference;

for each one of the second plurality of electrodes detecting a second electrical signal at the one of the first plurality of electrodes relative to a second electrical signal reference;

for each overlap region between one of the first plurality of electrodes and one of the second plurality of electrodes, estimating a pressure value for the overlap region based at least in part on: the first electrical signal corresponding to the one of the first plurality of electrodes; and the second electrical signal corresponding to the one of the second plurality of electrodes.

42. A method according to aspect 41 or any other aspect herein wherein detecting the first electrical signal at the one of the first plurality of electrodes relative to the first electrical signal reference comprises detecting a voltage difference between the one of the first plurality of electrodes and the first electrical signal reference.

43. A method according to aspect 41 or any other aspect herein wherein detecting the first electrical signal at the one of the first plurality of electrodes relative to the first electrical signal reference comprises detecting a current flow between the one of the first plurality of electrodes and the first electrical signal reference.

44. A method according to any one of aspects 41 to 43 or any other aspect herein comprising:
estimating a first average pressure corresponding to each one of the first plurality of electrodes based at least in part on the first electrical signal at the one of the first plurality of electrodes relative to the first electrical signal reference;
estimating a second average pressure corresponding to each one of the second plurality of electrodes based at least in part on the second electrical signal at the one of the second plurality of electrodes relative to the second electrical signal reference; and
wherein, for each overlap region between one of the first plurality of electrodes and one of the second plurality of electrodes, estimating the pressure value for the overlap region comprises estimating the pressure value based on at least in part on the first average pressure corresponding to the one of the first plurality of electrodes and on the second average pressure corresponding to the one of the second plurality of electrodes.

45. A method according to aspect 44 or any other aspect herein wherein, for each overlap region between one of the first plurality of electrodes and one of the second plurality of electrodes, estimating the pressure value based on at least in part on the first average pressure corresponding to the one of the first plurality of electrodes and on the second average pressure corresponding to the one of the second plurality of electrodes comprises:
scaling the first average pressure corresponding to the one of the first plurality of electrodes by a first scaling factor that depends on the second average pressure corresponding to the one of the second plurality of electrodes, to thereby obtain a first scaled value;
scaling the second average pressure corresponding to the one of the second plurality of electrodes by a second scaling factor that depends on the first average pressure corresponding to the one of the first plurality of electrodes, to thereby obtain a second scaled value; and
averaging the first and second scaled values to thereby obtain the pressure value for the overlap region.

46. A method according to aspect 45 or any other aspect herein wherein, for each overlap region between one of the first plurality of electrodes and one of the second plurality of electrodes, the first scaling factor comprises a ratio of: the second average pressure corresponding to the one of the second plurality of electrodes; and a sum of the second average pressures over the second plurality of electrodes.

47. A method according to any one of aspects 44 to 46 or any other aspect herein wherein estimating the first average pressure corresponding to each one of the first plurality of electrodes based at least in part on the first electrical signal at the one of the first plurality of electrodes relative to the first electrical signal reference comprises, for each one of the first plurality of electrodes, the first average pressure based on an empirically determined relationship between the first electrical signal and the corresponding first average pressure.

48. A method according to any one of aspects 44 to 47 or any other aspect herein comprising, for each one of the first plurality of electrodes, subjecting the detected first electrical signal at the one of the first plurality of electrodes relative to the first electrical signal reference to a thresholding process and, if the detected first electrical signal is less than a threshold, setting the first average pressure corresponding to the one of the first plurality of electrodes to be equal to a reference pressure.

49. A method according to aspect 48 or any other aspect herein wherein setting the first average pressure corresponding to the one of the first plurality of electrodes to be equal to a reference pressure comprises setting the first average pressure to be equal to atmospheric pressure.

50. A method according to any one of aspects 41 to 49 or any other aspect herein comprising any of the features, combinations of features and/or sub-combinations of features of any one or aspects 2 to 30.

51. A flexible sensor array for detecting pressure at one or more locations over a sensing surface, the sensor array comprising:
a first plurality of ionically conductive electrodes distributed over a working region adjacent the sensing surface, each of the first plurality of electrodes elongated in an x-direction that is generally tangential to the sensing surface and a second plurality of ionically conductive electrodes distributed over the working region, each of the second plurality of electrodes elongated in a y-direction, the y-direction generally tangential to the sensing surface and non-parallel with the x-direction;
each of the first plurality of electrodes overlapping each of the second plurality of electrodes in a z-direction generally normal to the sensing surface at a corresponding overlap region;
for each overlap region between one of the first plurality of electrodes and one of the second plurality of electrodes, a corresponding region of a deformable dielectric interposed between the one of the first plurality of electrodes and the one of the second plurality of electrodes in the z-direction;
wherein, for each overlap region between one of the first plurality of electrodes and one of the second plurality of electrodes, a capacitance between the one of the first plurality of electrodes and the one of the second plurality of electrodes depends on a state of deformation of one or more of the one of the first plurality of electrodes, the one of the second plurality of electrodes and the corresponding region of deformable dielectric.

52. A flexible sensor array according to aspect 51 or any other aspect herein wherein, for each overlap region between one of the first plurality of electrodes and one of the second plurality of electrodes, the corresponding region of deformable dielectric interposed between the one of the first plurality of electrodes and the one of the second plurality of electrodes in the z-direction has spatially varying stiffness/deformability within the corresponding region of deformable dielectric.

53. A flexible sensor array according to any one of aspects 51 to 52 or any other aspect herein wherein, for each overlap region between one of the first plurality of electrodes and one of the second plurality of electrodes, the corresponding region of deformable dielectric is spaced apart from the corresponding regions of deformable dielectric associated with other overlap regions in the array.

54. A flexible sensor array according to any one of aspects 51 to 52 or any other aspect herein wherein the deformable dielectric comprises a contiguous layer of deformable dielectric interposed between the first plurality of electrodes and the second plurality of electrodes in the z-direction and each corresponding region of deformable dielectric is part of the contiguous layer.

55. A flexible sensor array according to any one of aspects 51 to 54 wherein, for each overlap region between one of the first plurality of electrodes and one of the second plurality of electrodes, at least one of a capacitance and a resistance between the one of the first plurality of electrodes and the one of the second plurality of electrodes depends at least in part on an amount of moisture present in a vicinity of the corresponding region of deformable dielectric.

56. A flexible sensor array according to aspect 55 or any other aspect herein wherein for each overlap region between one of the first plurality of electrodes and one of the second plurality of electrodes, at least one of a capacitance and a resistance between the one of the first plurality of electrodes and the one of the second plurality of electrodes depends on an amount of moisture present in the corresponding region of deformable dielectric.

57. A flexible sensor array according to aspect 55 or any other aspect herein wherein for each overlap region between one of the first plurality of electrodes and one of the second plurality of electrodes, at least one of a capacitance and a resistance between the one of the first plurality of electrodes and the one of the second plurality of electrodes depends on an amount of moisture absorbed in the corresponding region of deformable dielectric.

58. A sensor array according to any one of aspects 51 to 57 or any other aspect herein comprising a sensing circuit connectable to output a sensing circuit signal corresponding to the capacitance between the one of the first plurality of electrodes and the one of the second plurality of electrodes for each overlap region and one or more multiplexers for connecting, for each overlap region, the one of the first plurality of electrodes and the one of the second plurality of electrodes to inputs of the sensing circuit to thereby cause the sensing circuit to output the sensing circuit signal.

59. A sensor array according to aspect 58 or any other aspect herein comprising a controller connected to provide control signals to the one or more multiplexers and configured to output control signals which control the one or more multiplexers to iteratively scan over the overlap regions in the working region and, for each overlap region, to effect the connections of the one of the first plurality of electrodes and the one of the second plurality of electrodes to the inputs of the sensing circuit.

60. A sensor array according to aspect 59 or any other aspect herein wherein, for each overlap region, the controller is configured to determine a pressure estimate for the overlap region based at least in part on the capacitance between the one of the first plurality of electrodes and the one of the second plurality of electrodes.

61. A sensor array according to aspect 60 or any other aspect herein wherein, for each overlap region, the controller is configured to determine the pressure estimate based on an inversely correlated relationship between the capacitance between the one of the first plurality of electrodes and the one of the second plurality of electrodes and the pressure estimate.

62. A sensor array according to any of aspects 51 to 61 comprising any of the features, combinations of features or sub-combinations of features of any of aspects 14 to 30.

63. A flexible sensor array for detecting pressure at one or more locations over a sensing surface, the sensor array comprising:
one or more piezoresistive ionically conductive elements distributed over a working region adjacent the sensing surface;
for each piezoresistive ionically conductive element, a pair of conductive electrodes in conductive contact with the piezoresistive ionically conductive element at spaced apart locations;
wherein for each piezoresistive ionically conductive element, a resistance between the pair of opposed conductive electrodes depends on a state of deformation of the piezoresistive ionically conductive element.

64. A sensor array according to aspect 63 or any other aspect herein comprising a plurality of piezoresistive ionically conductive elements distributed over the working region and wherein at least one of the pair of conductive electrodes is shared between at least two of the piezoresistive ionically conductive elements.

65. A sensor array according to aspect 63 or any other aspect herein wherein the one or more piezoresistive ionically conductive elements comprise:
a first plurality of piezoresistive ionically conductive elements distributed over the working region, each of the first plurality of piezoresistive ionically conductive elements elongated in an x-direction that is generally tangential to the sensing surface and a second plurality of piezoresistive ionically conductive elements distributed over the working region, each of the second plurality of piezoresistive ionically conductive elements elongated in a y-direction, the y-direction generally tangential to the sensing surface and non-parallel with the x-direction;
each of the first plurality of piezoresistive ionically conductive elements overlapping each of the second plurality of piezoresistive ionically conductive elements in a z-direction generally normal to the sensing surface at a corresponding overlap region; and
for each overlap region between one of the first plurality of piezoresistive ionically conductive elements and one of the second plurality of piezoresistive ionically conductive elements, a corresponding region of a deformable insulator interposed between the one of the first plurality of piezoresistive ionically conductive elements and the one of the second plurality of piezoresistive ionically conductive elements in the z-direction.

66. A flexible sensor array according to aspect 65 or any other aspect herein wherein the deformable insulator comprises a contiguous layer of deformable insulator interposed between the first plurality of piezoresistive ionically conductive elements and the second plurality of piezoresistive ionically conductive elements in the z-direction and each corresponding region of deformable insulator is part of the contiguous layer.

67. A flexible sensor array according to aspect 65 or any other aspect herein wherein, for each overlap region between one of the first plurality of piezoresistive ionically conductive elements and one of the second plurality of piezoresistive ionically conductive elements, the corresponding region of deformable insulator is spaced apart from the corresponding regions of deformable insulator associated with other overlap regions in the array.

68. A sensor array according to any one of aspects 65 to 67 or any other aspect herein comprising a sensing circuit connectable to output a sensing circuit signal which depends on the resistance between a pair of its inputs and one or more multiplexers for connecting, for each piezoresistive ionically conductive element, each pair of conductive electrodes in conductive contact with the piezoresistive ionically conductive element to the inputs of the sensing circuit to thereby cause the sensing circuit to output the sensing circuit signal for the piezoresistive ionically conductive element.

69. A sensor array according to aspect 68 or any other aspect herein comprising a controller connected to provide control signals to the one or more multiplexers and configured to output control signals which control the one or more multiplexers to iteratively scan over the one or more piezoresistive ionically conductive elements in the working region and, for each piezoresistive ionically conductive element, to effect the connections of the pair of electrodes in conductive contact with the piezoresistive ionically conductive element to the inputs of the sensing circuit.

70. A sensor array according to aspect 69 or any other aspect herein wherein, for each overlap region between one of the first plurality of piezoresistive ionically conductive elements and one of the second plurality of piezoresistive ionically conductive elements, the controller is configured to determine a pressure estimate for the overlap region based at least in part on a first resistance of the one of the first plurality of piezoresistive ionically conductive elements and a second resistance of the one of the second plurality of piezoresistive ionically conductive elements.

71. A sensor array according to any of aspects 63 to 70 comprising any of the features, combinations of features or sub-combinations of features of any of aspects 14 to 30.

72. A flexible sensor array for detecting pressure at one or more locations over a sensing surface, the sensor array comprising:
a piezoresistive ionically conductive element distributed over a working region adjacent the sensing surface;
a plurality of three or more conductive electrodes in conductive contact with the piezoresistive ionically conductive element at spaced apart locations;
wherein a resistance between any pair of the plurality of conductive electrodes depends on a state of deformation of the piezoresistive ionically conductive element in a region between the pair of the plurality of conductive electrodes.

73. A sensor array according to aspect 72 or any other aspect herein comprising a sensing circuit connectable to output a sensing circuit signal corresponding to the resistance between a pair of its inputs and one or more multiplexers for connecting pairs of the plurality of conductive electrodes to the inputs of the sensing circuit to thereby cause the sensing circuit to output the sensing circuit signal for each connected pair of the plurality of conductive electrodes.

74. A sensor array according to aspect 73 or any other aspect herein comprising a controller connected to provide control signals to the one or more multiplexers and configured to output control signals which control the one or more multiplexers to iteratively scan over a plurality of pairs of the plurality of conductive electrodes and for each pair of the plurality of conductive electrodes, to effect the connections of the pair of electrodes to the inputs of the sensing circuit.

75. A sensor array according to aspect 74 or any other aspect herein wherein the controller is configured to determine a pressure map over the sensing surface based at least in part on the resistances corresponding to the plurality of pairs of the plurality of conductive electrodes.

76. A sensor array according to any of aspects 72 to 75 comprising any of the features, combinations of features or sub-combinations of features of any of aspects 14 to 30.

77. A flexible sensor array for detecting moisture at one or more locations over a sensing surface, the sensor array comprising:
a first plurality of ionically conductive electrodes distributed over a working region adjacent the sensing surface, each of the first plurality of electrodes elongated in an x-direction that is generally tangential to the sensing surface and a second plurality of ionically conductive electrodes distributed over the working region, each of the second plurality of electrodes elongated in a y-direction, the y-direction generally tangential to the sensing surface and non-parallel with the x-direction;
each of the first plurality of electrodes overlapping each of the second plurality of electrodes in a z-direction generally normal to the sensing surface at a corresponding overlap region;
for each overlap region between one of the first plurality of electrodes and one of the second plurality of electrodes, a corresponding region of deformable dielectric interposed between the one of the first plurality of electrodes and the one of the second plurality of electrodes in the z-direction;
wherein, for each overlap region between one of the first plurality of electrodes and one of the second plurality of electrodes, at least one of a capacitance and a resistance between the one of the first plurality of electrodes and the one of the second plurality of electrodes depends on an amount of moisture present in a vicinity of the corresponding region of deformable dielectric.

78. A flexible sensor array according to aspect 77 or any other aspect herein wherein, for each overlap region between one of the first plurality of electrodes and one of the second plurality of electrodes, at least one of the capacitance and the resistance between the one of the first plurality of electrodes and the one of the second plurality of electrodes depends on an amount of moisture present in the corresponding region of deformable dielectric.

79. A flexible sensor array according to any one of aspects 77 to 78 or any other aspect herein wherein, for each overlap region between one of the first plurality of electrodes and one of the second plurality of electrodes, at least one of the capacitance and the resistance between the one of the first plurality of electrodes and the one of the second plurality of electrodes depends on an amount of moisture absorbed in the corresponding region of deformable dielectric.

80. A flexible sensor array according to any one of aspects 77 to 79 or any other aspect herein wherein, for each overlap region between one of the first plurality of electrodes and one of the second plurality of electrodes, the corresponding region of deformable dielectric is spaced apart from the corresponding regions of deformable dielectric associated with other overlap regions in the array.
81. A flexible sensor array according to any one of aspects 77 to 79 or any other aspect herein wherein the deformable dielectric comprises a contiguous layer of deformable dielectric interposed between the first plurality of ionically conductive electrodes and the second plurality of ionically conductive electrodes in the z-direction and each corresponding region of deformable dielectric is part of the contiguous layer.
82. A flexible sensor array according to any one of aspects 77 to 81 or any other aspect herein wherein the sensor array is in moisture-transmitting contact with the sensing surface.
83. A sensor array according to any one of aspects 77 to 82 or any other aspect herein comprising a sensing circuit connectable to output a sensing circuit signal corresponding to an impedance between the one of the first plurality of electrodes and the one of the second plurality of electrodes for each overlap region and one or more multiplexers for connecting, for each overlap region, the one of the first plurality of electrodes and the one of the second plurality of electrodes to inputs of the sensing circuit to thereby cause the sensing circuit to output the sensing circuit signal.
84. A sensor array according to aspect 83 or any other aspect herein comprising a controller connected to provide control signals to the one or more multiplexers and configured to output control signals which control the one or more multiplexers to iteratively scan over the overlap regions in the working region and, for each overlap region, to effect the connections of the one of the first plurality of electrodes and the one of the second plurality of electrodes to the inputs of the sensing circuit.
85. A sensor array according to aspect 84 or any other aspect herein wherein, for each overlap region, the controller is configured to determine a moisture level estimate for the overlap region based at least in part on the impedance between the one of the first plurality of electrodes and the one of the second plurality of electrodes.
86. A sensor array according to any one of aspects 84 to 85 or any other aspect herein wherein, for each overlap region, the controller is configured to determine a pressure estimate for the overlap region based at least in part on the impedance between the one of the first plurality of electrodes and the one of the second plurality of electrodes.
87. A sensor array according to any of aspects 77 to 86 comprising any of the features, combinations of features or sub-combinations of features of any of aspects 14 to 30.
88. A method for generating a pressure map of a sensing surface comprising:
providing a flexible sensor array comprising:
a first plurality of ionically conductive electrodes distributed over a working region adjacent the sensing surface, each of the first plurality of electrodes elongated in an x-direction that is generally tangential to the sensing surface and a second plurality of ionically conductive electrodes distributed over the working region, each of the second plurality of electrodes elongated in a y-direction, the y-direction generally tangential to the sensing surface and non-parallel with the x-direction;
each of the first plurality of electrodes overlapping each of the second plurality of electrodes in a z-direction generally normal to the sensing surface at a corresponding overlap region;
for each overlap region between one of the first plurality of electrodes and one of the second plurality of electrodes, a corresponding region of deformable dielectric interposed between the one of the first plurality of electrodes and the one of the second plurality of electrodes in the z-direction;
for each overlap region:
detecting a capacitance which depends on a state of deformation of one or more of the one of the first plurality of electrodes, the one of the second plurality of electrodes and the corresponding region of deformable dielectric; and
estimating a pressure value for the overlap region based at least in part on the detected capacitance.
89. A method according to aspect 88 or any other aspect herein comprising, for each overlap region, estimating a corresponding pressure based on an empirically determined relationship between the detected capacitance and the corresponding pressure.
90. A method according to any one of aspects 88 to 89 or any other aspect herein wherein, for each overlap region, estimating a pressure value for the overlap region based at least in part on the detected capacitance comprises subjecting the detected capacitance to a thresholding process and, if the detected capacitance is greater than a threshold, setting the pressure value for the overlap region to be equal to a reference pressure.
91. A method according to aspect 90 or any other aspect herein wherein setting the pressure value for the overlap region to be equal to a reference pressure comprises setting the pressure value for the overlap region to be equal to atmospheric pressure.
92. A method according to any one of aspects 88 to 91 or any other aspect herein comprising any of the features, combinations of features and/or sub-combinations of features of any one or aspects 2 to 30.
93. A method for generating a pressure map of a sensing surface comprising:
providing a flexible sensor array comprising:
one or more piezoresistive ionically conductive elements distributed over a working region adjacent the sensing surface;
for each piezoresistive ionically conductive element, a pair of conductive electrodes in conductive contact with the piezoresistive ionically conductive element at spaced apart locations; and
for each piezoresistive ionically conductive element:
detecting a resistance between the pair of opposed conductive electrodes in conductive contact with piezoresistive ionically conductive element wherein the resistance depends on a state of deformation of the piezoresistive ionically conductive element; and
estimating at least one pressure value for a region of the sensing surface overlapping the piezoresistive ionically conductive element in a z-direction generally normal to the sensing surface based at least in part on the detected resistance.

94. A method according to aspect 93 or any other aspect herein wherein providing the flexible sensor array comprises providing:
a first plurality of piezoresistive ionically conductive elements distributed over the working region, each of the first plurality of piezoresistive ionically conductive elements elongated in an x-direction that is generally tangential to the sensing surface and a second plurality of piezoresistive ionically conductive elements distributed over the working region, each of the second plurality of piezoresistive ionically conductive elements elongated in a y-direction, the y-direction generally tangential to the sensing surface and non-parallel with the x-direction;
each of the first plurality of piezoresistive ionically conductive elements overlapping each of the second plurality of piezoresistive ionically conductive elements in the z-direction at a corresponding overlap region; and
for each overlap region between one of the first plurality of piezoresistive ionically conductive elements and one of the second plurality of piezoresistive ionically conductive elements, a corresponding region of a deformable insulator interposed between the one of the first plurality of piezoresistive ionically conductive elements and the one of the second plurality of piezoresistive ionically conductive elements in the z-direction;
and wherein the method further comprises:
for each one of the first plurality of piezoresistive ionically conductive elements detecting a first resistance of the one of the first plurality of piezoresistive ionically conductive elements;
for each one of the second plurality of piezoresistive ionically conductive elements detecting a second resistance of the one of the second plurality of piezoresistive ionically conductive elements;
for each overlap region between one of the first plurality of piezoresistive ionically conductive elements and one of the second plurality of piezoresistive ionically conductive elements, estimating a pressure value for the overlap region based at least in part on: the first resistance of the one of the first plurality of piezoresistive ionically conductive elements; and the second resistance of the one of the second plurality of piezoresistive ionically conductive elements.

95. A method according to aspect 94 or any other aspect herein comprising:
estimating a first average pressure corresponding to each one of the first plurality of piezoresistive ionically conductive elements based at least in part on the first resistance of the one of the first plurality of electrodes;
estimating a second average pressure corresponding to each one of the second plurality of piezoresistive ionically conductive elements based at least in part on the second resistance of the one of the second plurality of piezoresistive ionically conductive elements; and
wherein, for each overlap region between one of the first plurality of piezoresistive ionically conductive elements and one of the second plurality of piezoresistive ionically conductive elements, estimating the pressure value for the overlap region comprises estimating the pressure value based on at least in part on the first average pressure corresponding to the one of the first plurality of piezoresistive ionically conductive elements and on the second average pressure corresponding to the one of the second plurality of piezoresistive ionically conductive elements.

96. A method according to aspect 95 or any other aspect herein wherein, for each overlap region between one of the first plurality of piezoresistive ionically conductive elements and one of the second plurality of piezoresistive ionically conductive elements, estimating the pressure value based on at least in part on the first average pressure corresponding to the one of the first plurality of piezoresistive ionically conductive elements and on the second average pressure corresponding to the one of the second plurality of piezoresistive ionically conductive elements comprises:
scaling the first average pressure corresponding to the one of the first plurality of piezoresistive ionically conductive elements by a first scaling factor that depends on the second average pressure corresponding to the one of the second plurality of piezoresistive ionically conductive elements, to thereby obtain a first scaled value;
scaling the second average pressure corresponding to the one of the second plurality of piezoresistive ionically conductive elements by a second scaling factor that depends on the first average pressure corresponding to the one of the first plurality of piezoresistive ionically conductive elements, to thereby obtain a second scaled value; and
averaging the first and second scaled values to thereby obtain the pressure value for the overlap region.

97. A method according to aspect 96 or any other aspect herein wherein, for each overlap region between one of the first plurality of piezoresistive ionically conductive elements and one of the second plurality of piezoresistive ionically conductive elements, the first scaling factor comprises a ratio of: the second average pressure corresponding to the one of the second plurality of piezoresistive ionically conductive elements; and a sum of the second average pressures over the second plurality of piezoresistive ionically conductive elements.

98. A method according to any one of aspects 95 to 97 or any other aspect herein wherein estimating the first average pressure corresponding to each one of the first plurality of piezoresistive ionically conductive elements based at least in part on the first resistance of the one of the first plurality of piezoresistive ionically conductive elements comprises, for each one of the first plurality of piezoresistive ionically conductive elements, the first average pressure based on an empirically determined relationship between the first resistance and the corresponding first average pressure.

99. A method according to any one of aspects 95 to 98 or any other aspect herein comprising, for each one of the first plurality of piezoresistive ionically conductive elements, subjecting the detected first resistance of the one of the first plurality of piezoresistive ionically conductive elements to a thresholding process and, if the detected first resistance is less than a threshold, setting the first average pressure corresponding to the one of the first plurality of piezoresistive ionically conductive elements to be equal to a reference pressure.

100. A method according to aspect 99 or any other aspect herein wherein setting the first average pressure corresponding to the one of the first plurality of piezoresistive ionically conductive elements to be equal to a reference pressure comprises setting the first average pressure to be equal to atmospheric pressure.

101. A method according to any one of aspects 93 to 100 or any other aspect herein comprising any of the features, combinations of features and/or sub-combinations of features of any one of aspects 2 to 30.

102. A method for generating a moisture map of a sensing surface comprising:
providing a flexible sensor array comprising:
a first plurality of ionically conductive electrodes distributed over a working region adjacent the sensing surface, each of the first plurality of electrodes elongated in an x-direction that is generally tangential to the sensing surface and a second plurality of ionically conductive electrodes distributed over the working region, each of the second plurality of electrodes elongated in a y-direction, the y-direction generally tangential to the sensing surface and non-parallel with the x-direction;
each of the first plurality of electrodes overlapping each of the second plurality of electrodes in a z-direction generally normal to the sensing surface at a corresponding overlap region;
for each overlap region between one of the first plurality of electrodes and one of the second plurality of electrodes, a corresponding region of deformable dielectric interposed between the one of the first plurality of electrodes and the one of the second plurality of electrodes in the z-direction;
for each overlap region:
applying a frequency swept AC signal to the one of the first plurality of electrodes to determine a frequency response, over a range of frequencies, of the combination of the one of the first plurality of electrodes, the one of the second plurality of electrodes and the corresponding region of deformable dielectric, the frequency response dependent at least in part on the amount of moisture present in the corresponding region of deformable dielectric;
estimating a moisture value for the overlap region based at least in part on the frequency response.

103. A method according to aspect 102 or any other aspect herein wherein the sensing surface is in moisture-transfer contact with the sensor array.

104. A method according to any one of aspects 102 to 103 or any other aspect herein wherein, for each overlap region, estimating the moisture value for the overlap region comprises:
curve fitting the frequency response to a frequency response of a representative RC circuit, to determine a representative resistance R and representative capacitance C that fit the frequency response;
using empirically determine relationships between the representative resistance R, the representative capacitance C and moisture to estimate the moisture value for the overlap region.

105. A method according to any one of aspects 102 to 103 or any other aspect herein comprising generating a pressure map of the sensing surface, wherein generating the pressure map of the sensing surface comprises, for each overlap region, estimating a pressure value for the overlap region based at least in part on the frequency response.

106. A method according to aspect 105 or any other aspects herein wherein, for each overlap region, estimating the pressure value for the overlap region and estimating the moisture value for the overlap region comprise:
curve fitting the frequency response to a frequency response of a representative RC circuit, to determine a representative resistance R and representative capacitance C that fit the frequency response;
using empirically determine relationships between the representative resistance R, the representative capacitance C, moisture and pressure to estimate the moisture value and the pressure value for the overlap region.

107. A method according to any one of aspects 102 to 106 or any other aspect herein comprising any of the features, combinations of features and/or sub-combinations of features of any one or aspects 2 to 30.

108. A method for generating a pressure map of a sensing surface comprising:
providing a flexible sensor array comprising:
a piezoresistive ionically conductive element distributed over a working region adjacent the sensing surface;
a plurality of three or more conductive electrodes in conductive contact with the piezoresistive ionically conductive element at spaced apart locations;
wherein a resistance between any pair of the plurality of conductive electrodes depends on a state of deformation of the piezoresistive ionically conductive element in a region between the pair of the plurality of conductive electrodes;
for each of a plurality of pairs of excitation electrodes from among the plurality of conductive electrodes, obtaining a corresponding measured voltage contour by:
applying a current signal between the pair of excitation electrodes; and
measuring a voltage difference between a plurality of pairs of other electrodes;
determining the corresponding measured voltage contour based on the measured voltage differences;
estimating the pressure map over the sensing surface based on the plurality of measured voltage contours corresponding to the plurality of pairs of excitation electrodes.

109. A method according to aspect 108 or any other aspect herein wherein estimating the pressure map over the sensing surface based on the plurality of measured voltage contours corresponding to the plurality of pairs of excitation electrodes comprises superposing the plurality of measured voltage contours to obtain a superposed voltage contour and estimating the pressure map over the sensing surface based on the superposed voltage contour.

110. A method according to aspect 109 or any other aspect herein wherein estimating the pressure map over the sensing surface based on the superposed voltage contour comprises: dividing the superposed voltage contour by the applied current signal to obtain an impedance contour and determining the pressure map from the impedance contour based on an empirically determined relationship between the impedance and pressure for the piezoresistive ionically conductive element.

111. A method according to any one of aspects 108 to 110 or any other aspect herein comprising any of the features, combinations of features and/or sub-combinations of features of any one or aspects 2 to 30.

112. A method for generating a pressure map of a sensing surface comprising:
providing a flexible sensor array comprising:
a piezoionic ionically conductive element distributed over a working region adjacent the sensing surface;
a plurality of conductive electrodes in conductive contact with the piezoionic ionically conductive element at spaced apart locations;

wherein a voltage between any pair of the plurality of conductive electrodes or at any one of the conductive electrodes relative to some voltage reference depends on a state of deformation of the piezoionic ionically conductive element;

obtaining a corresponding measured voltage for each of the plurality of conductive electrodes;

meshing the sensing surface using a plurality of notional intersecting straight mesh lines, each mesh line extending between a corresponding pair of the plurality of conductive electrodes;

determining voltage values for a plurality of intersections between the mesh lines based on the measured voltages for the conductive electrodes between which the intersecting mesh lines extend; and estimating the pressure map over the sensing surface based at least on part on the plurality of voltage values corresponding to the plurality of intersections.

113. A method according to aspect 112 or any other aspect herein wherein determining voltage values for the plurality of intersections comprises: for each mesh line, assuming a model of the change of voltage between the conductive electrodes between which the mesh line extends; and for each intersection between a pair of mesh lines, combining values predicted by the models for each of the intersecting pair of mesh lines to obtain the voltage value for the intersection.

114. A method according to aspect 113 or any other aspect herein wherein assuming the model of the change of voltage between the conductive electrodes between which the mesh line extends comprises assuming that the voltage changes linearly between the conductive electrodes between which the mesh line extends.

115. A method according to any one of aspects 113 to 114 or any other aspect herein wherein combining values predicted by the models for each of the intersecting pair of mesh lines comprises at least one of: determining a sum of the values predicted by the models for each of the intersecting pair of mesh lines to be the voltage value for the intersection; and determine an average of the values predicted by the models for each of the intersecting pair of mesh lines to be the voltage value for the intersection; and 116. A method according to any one of aspects 112 to 115 or any other aspect herein comprising: determining a fine mesh between intersecting mesh lines based on the voltage values for the plurality of intersections of the mesh lines; determining fine mesh voltage values for fine mesh intersections between fine mesh lines; and determining the pressure map based at least in part on the fine mesh voltage values.

117. A method according to any one of aspects 112 to 116 or any other aspect herein comprising any of the features, combinations of features and/or sub-combinations of features of any one or aspects 2 to 30.

118. A flexible sensor array for detecting pressure at one or more locations over a sensing surface, the sensor array comprising:

a piezoionic ionically conductive element distributed over a working region adjacent the sensing surface;

a plurality of three or more conductive electrodes in conductive contact with the piezoionic ionically conductive element at spaced apart locations;

wherein a voltage between any pair of the plurality of conductive electrodes or at any one of the conductive electrodes relative to some voltage reference depends on a state of deformation of the piezoionic ionically conductive element.

119. A sensor array according to aspect 118 or any other aspect herein comprising any of the features, combinations of features and/or sub-combinations of features of any one or aspects 2 to 30.

Other aspects of the invention provide sensor arrays comprising any feature, combination of features, or sub-combinations of features of any of the embodiments described herein and/or in the accompanying drawings.

Other aspects of the invention provide methods for detecting pressure, pressure maps of sensing surfaces, moisture and/or moisture maps of sensing surfaces comprising any feature, combination of features, or sub-combinations of features of any of the embodiments described herein and/or in the accompanying drawings In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

DESCRIPTION

Figure 1A:
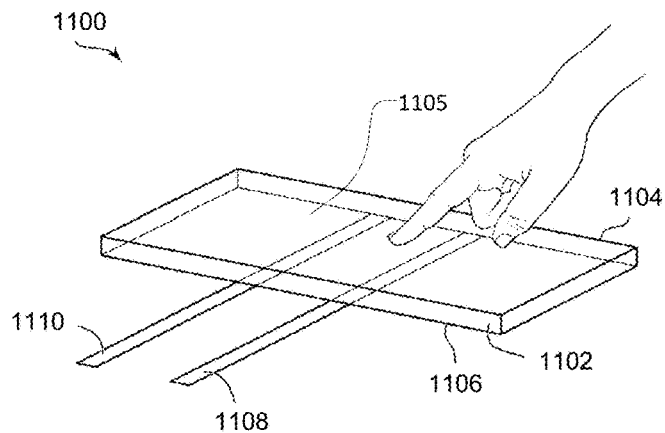
FIG. 1A is a schematic cross-sectional view of a pressure sensor comprising piezoionic ionically conductive material according to one embodiment of the invention.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Pressure sensors according to particular embodiments comprise ionically conductive material. Ionically conductive materials can be used to transmit or otherwise impact electrical signals based on ion movement within the ionically conductive material. Advantageously, ionically conductive materials can be made from materials that are transparent, deformable, biocompatible and inexpensive.

There is a general desire to estimate, or otherwise detect, characteristics (e.g. presence, location and magnitude) of the pressure applied at one or more regions on a sensing surface—e.g. to provide a "pressure map" over the sensing surface. By way of non-limiting example, it may be desirable to implement a sensor array on a sensing surface located in or on a mattress of a bed (e.g. in a bed sheet), to detect a pressure map associated with anyone located on top of the bed. As another non-limiting example, it may be desirable to implement a sensor array on a sensing surface corresponding to the display surface of an electronic device, so that the electronic device may be configured to respond to "gestures" incorporating pressures at one or more locations on the sensing surface and possibly to differential pressures at different locations on the surface.

A number of different types of pressure sensors incorporating ionically conductive materials are disclosed in:

Patent Cooperation Treaty (PCT) application No. PCT/CA2015/051265 (the '265 application) filed 3 Dec. 2015 and entitled FLEXIBLE TRANSPARENT SENSOR WITH IONICALLY-CONDUCTIVE MATERIAL, which is hereby incorporated herein by reference; and PCT application No. PCT/CA2016/050238 (the '238 application) filed 4 Mar. 2016 and entitled METHOD AND SENSOR FOR PRESSURE SENSING BASED ON ELECTRICAL SIGNAL GENERATED BY REDISTRIBUTION OF MOBILE IONS IN PIEZOIONIC LAYER, which is hereby incorporated herein by reference.

Pressure sensors incorporating ionically conductive materials may estimate pressure based on electrical characteristics of the sensors and/or their ionically conductive materials which vary with applied pressure, corresponding deformation and/or the like. Such pressure-dependent electrical characteristics may include capacitance, resistance, voltage, current and/or the like. Sensors according to particular example embodiments and/or aspects of the invention may comprise piezoresistive components comprising ionically conducting materials, whose resistance varies with applied pressure, corresponding deformation and/or the like. Sensors according to particular example embodiments and/or aspects of the invention may comprise components comprising ionically conductive materials, whose capacitance varies with applied pressure, corresponding deformation and/or the like. Sensors according to particular example embodiments and/or aspects of the invention may comprise piezoionic components which generate voltages and/or currents in response to applied pressure, corresponding deformation and/or the like. Some embodiments and aspects of the invention comprise methods of operating and/or fabricating any such sensors.

One aspect of the invention provides a method for sensing one or more characteristics (e.g. presence, location, magnitude and/or the like) of pressure applied to a sensing surface. The method comprises: monitoring an electrical signal generated by redistribution of mobile ions in a piezoionic layer comprising, or in force-transmitting contact with, the sensing surface, wherein the redistribution of mobile ions in the piezoionic layer is induced by an externally applied local pressure at a portion of the layer; and determining one or more characteristics (e.g. presence, location, magnitude or the like) of pressure being applied to the sensing surface based on the monitored electrical signal. The redistribution of mobile ions in the piezoionic layer may be induced by an externally applied local pressure without application of an external electrical signal to the piezoionic layer, although an external electrical signal could be applied in some embodiments. It may be determined that pressure is being applied to the sensing surface at a location proximate to the portion of the piezoionic layer. The electrical signal may be monitored through at least two electrodes in conductive contact with the piezoionic layer at different locations. The electrodes may be conductively connected to the piezoionic layer on a side of the piezoionic layer opposite to a side of the sensing surface, although this is not necessary. The electrical signal generated by redistribution of mobile ions may comprise a voltage or current, or both, between a first electrode at a first one of the locations and a second electrode at a second one of the locations.

Another aspect of the invention provides a piezoionic sensor array. The sensor array senses the pressure on a sensing surface. The sensor comprises a piezoionic layer comprising, or disposed in force-transmitting contact with, the sensing surface such that an externally applied local pressure on a portion of the sensing surface causes detectable redistribution of mobile ions in the piezoionic layer; and a plurality of electrodes in conductive contact with the piezoionic layer, the plurality of electrodes outputting an electrical signal generated by the redistribution of mobile ions in the piezoionic layer. The redistribution of mobile ions in the piezoionic layer may be induced by an externally applied local pressure and detectable without application of an external electrical signal to the piezoionic layer, although an external electrical signal could be applied in some embodiments. The electrodes may be in conductive contact with the piezoionic layer at different (e.g. spaced apart) locations. The electrodes may be conductively connected to the piezoionic layer on a side of the piezoionic layer opposite to a side of the sensing surface.

Another aspect of the invention provides a piezoresistive ionically conductive sensor array. The sensor array senses the pressure on a two dimensional sensing surface. The sensor array comprises one or more piezoresistive ionically conductive elements that are distributed over the sensing surface. In some embodiments, the sensor array comprises, or is disposed in force-transmitting contact with, the sensing surface such that an externally applied local pressure on a portion of the sensing surface causes changes in resistance to the piezoresistive ionically conductive elements. A plurality of electrodes are in conductive contact with the piezoresistive ionically conductive elements at different (e.g. spaced apart) locations for measuring resistance(s) of the piezoresistive ionically conductive elements.

Another aspect of the invention provides a method for sensing one or more characteristics (e.g. presence, location, magnitude and/or the like) of pressure applied to a two dimensional sensing surface. The method comprises monitoring resistances of one or more piezoresistive ionically conductive elements that comprise or are in force-transmitting contact with, the sensing surface. Pressure applied to the sensing surface changes the resistance(s) of the one or more piezoresistive ionically conductive elements and these resistances are used to estimate pressure over the two-dimensional sensing surface.

Another aspect of the invention provides a capacitive ionically conductive sensor array. The sensor array senses the pressure on a two dimensional sensing surface. The sensor array comprises a plurality of capacitive ionically conductive sensor elements distributed in a working region adjacent to the sensor surface. Each capacitive ionically conductive sensor element may comprise a pair of electrodes fabricated from ionically conductive materials and may have a dielectric material therebetween. In some embodiments, the sensor array comprises, or is disposed in force-transmitting contact with, the sensing surface such that an externally applied local pressure on a portion of the sensing surface causes changes in capacitance to the capacitive ionically conductive sensor elements. The capacitive ionically conductive sensor array may additionally or alternative detect moisture over the sensing surface.

Another aspect of the invention provides a method for sensing one or more characteristics (e.g. presence, location, magnitude and/or the like) of pressure applied to a two dimensional sensing surface. The method comprises monitoring capacitances of a plurality of capacitive ionically conductive sensor elements that comprise or are in force-transmitting contact with, the sensing surface. Pressure applied to the sensing surface changes the capacitances of the plurality of capacitive ionically conductive sensor elements and these capacitances are used to estimate pressure over the two-dimensional sensing surface.

Another aspect of the invention provides a method for sensing one or more characteristics (e.g. presence, location, magnitude and/or the like) of moisture over a two dimensional sensing surface. The method comprises monitoring impedances of a plurality of ionically conductive sensor elements that comprise or are in moisture-transmitting contact with, the sensing surface. Moisture present on the sensing surface changes the impedances of the ionically conductive sensor elements and these impedances are used to estimate moisture over the two-dimensional sensing surface.

Ionically conductive materials used in sensors described herein may include gels such as hydrogels, ionic polymers, porous polymers, membranes such as cationic membranes or anionic membranes, IPNs, polyethylene oxides, and the like. Cellulose or paper materials may also be used, which can be transparent. The ionically conductive material may be flexible, stretchable and transparent. For example, the ionically conductive material may be a polymer, such as an ionically conductive hydrogel, which may be formed from a polyacrylamide or a polyurethane. The hydrogel may include an electrolyte for providing conducting ions. In some applications, a salt such as NaCl or KCl, may be included in the hydrogel for providing conducting ions. The electrolyte may be dissolved in a solvent such as water. Depending on the polymer used for the hydrogel, other solvents including propylene carbonate, acetonitrile and other organic solvents may also be suitable. In some applications, a pure ionic liquid may be used to provide the electrolyte, in which case a solvent may not be necessary. Suitable ionic liquids may include 1-ethyl-3-methylimidazolium bis(trifluoromethylsulfonyl)imide (EMI TFSI). Suitable ionically conductive materials also include Nafion (asulfonated tetrafluoroethylene based fluoropolymer-copolymer), Flemion (perfluorinated carboxylic acid membrane), agar, cationic and anionic membranes, and gels including natural gels based on chitosan. Suitable cationic ion exchange membranes include Aciplex k-192, Selemion CMV, Nafion, FKS, Flemion, FKD, CR61-CMP, Ralex CM-PES, PC-SK, Morgane CDS, Neosepta CM1, TWCED or the like. Suitable anionic ion exchange membranes include Aciplex A-192, Selemion AMV, FAS, FAB, Ralex MH-PES, Morgane ADP, Neosepta AM1, TWEDG, or the like.

Some aspects of the invention provide sensors incorporating piezoionic pressure sensors and methods of operating and fabrication of same. FIG. 1A schematically illustrates a piezoionic pressure sensor 1100 according to an example embodiment. Sensor 1100 includes a piezoionic layer 1102 (made up of ionically conductive material), having a first side 1104 and an opposite second side 1106. For ease of description it is assumed that first side 1104 of piezoionic layer 1102 is itself the sensing surface 1105; however, in some embodiments, sensing surface 1105 may be in force-transmitting contact with first side 1104 of piezoionic layer 1102. Two electrodes 1108 and 1110 are in conductive contact with piezoionic layer 1102 (e.g. on second side 1106).

Piezoionic layer 1102 may be fabricated using any suitable piezoionic material that provides mobile ions that are capable of being displaced within the material as a result of local stress or compression, where different types of mobile ions have different mobility. The piezoionic material may be selected so that the expected external pressure to be detected will generate a detectable electrical potential difference over the distance between electrodes 1108 and 1110. The piezoionic material may include a suitable polymer or hydrogel material. Electrodes 1108 and 1110 may be fabricated using any suitable conductive materials, such as metals, metal alloys, other electronic conductors or ionic conductors. Other materials that are known to be suitable for use as electrodes or conductors may also be used. Further details of possible piezoionic materials, electrode materials and characteristics thereof are described, for example, in the '238 application.

Touch sensor 1100 may be fabricated any suitable process which can include conventional processing techniques for preparing the component materials including piezoionic layer 1102 and electrodes 1108, 1110, and for attaching electrodes 1108, 1110 to piezoionic layer 1102.

Figure 1B:
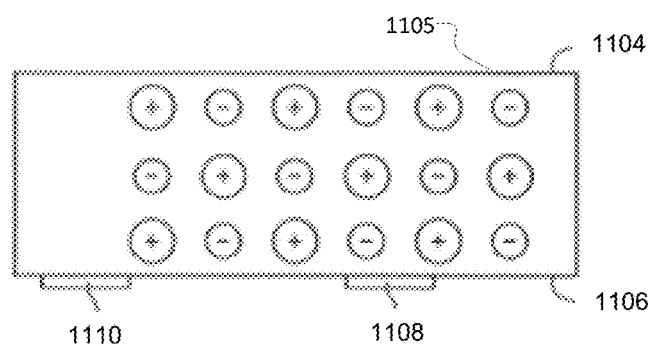
FIGS. 1B and 1C are schematic illustrative cross-sectional views of the FIG. 1A sensor during use.
Figure 1C:
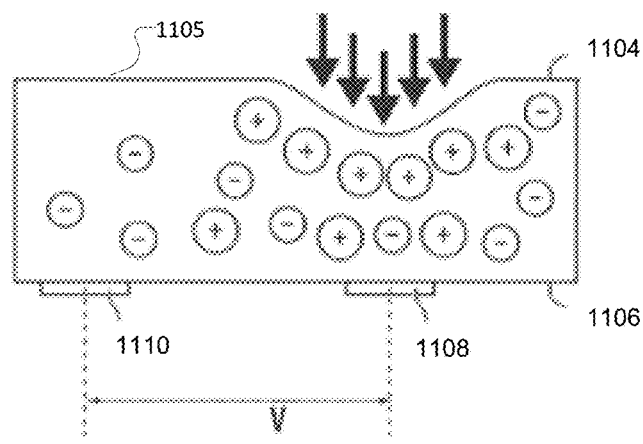

For illustration purposes only, the expected movements and distribution of the ions before and during an application of pressure to first side 1104 of sensor 1100 are schematically illustrated in FIG. 1B and FIG. 10. It should be understood that the depiction in FIGS. 1B and 10 is schematic and illustrative and does not represent actual movement or distribution of the ions in practice.

As shown in FIG. 1B, it can be expected that before sensing surface 1105 of first side 1104 is touched, or otherwise depressed or disturbed, the ions in the region proximate to electrode 1108 are evenly distributed and balanced. The potential difference between electrodes 1108 and 1110 is zero or minimal. When sensing surface 1105 is touched and depressed as shown in FIG. 10, the changes in the material framework/backbone cause a charge re-distribution. It is assumed, for illustration purposes, that in this example the cations in the material are less mobile and largely remain in the region near the touch location, and more anions are displaced away from the region above electrode 1108. It is possible that some cations will also move away from the applied pressure, but their movement is assumed to be slower than that of the anions in the FIG. 10 example. It is possible that an individual mobile ion will not travel the full distance between electrodes 1108, 1110, but it is assumed that the collective movement of the mobile ions caused by the touch will result in redistribution of ionic charges and detectable changes of ionic charge concentrations at regions proximate to electrodes 1108 and 1110. As can be appreciated, the mobility of different ions may depend on a number of factors such as charge polarity, ion size, concentration, solvation sphere, backbone structure and charge property, and other factors. For example, in a polar solvent such as water, the solvent molecule is electrostatically attracted to both the cation and the anion of the salt, resulting in a solvation shell/sphere surrounding the ion. This makes the ion effectively larger in diameter and hence less mobile due to increased drag. Thus, it is possible to select the piezoionic material with a suitable combination of the backbone or gel material and the electrolyte material to provide mobile ions with different mobility. The selective displacement of mobile ions and charge redistribution generates a non-zero potential difference between electrodes 1108, 1110, which can be detected as an electrical signal using a readout circuit (not shown in FIGS. 1B and 10).

Figure 1D:
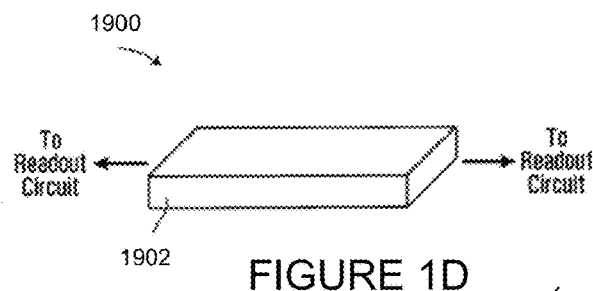
FIG. 1D is a schematic depiction of a pressure sensor comprising piezoresistive ionically conductive material according to an example embodiment of the invention.

Some aspects of the invention provide sensors incorporating piezoresistive pressure sensors and methods of operating and fabrication of same. Piezoresistive sensors may exhibit a change in resistance due to application of pressure to and/or corresponding deformation of the ionically conductive piezoresistive sensor material. Accordingly, a local change in resistance can be used to detect touch or other pressure. FIG. 1D schematically illustrates a piezoresistive sensor 1900 according to an example embodiment. Sensor 1900 includes a piezoresistive element 1902 comprising ionically conductive material. Piezoresistive element 1902 may be fabricated from any of the ionically conductive (and have any of the properties of the ionically conductive materials) described in connection with piezoresistive sensors herein, in the '265 application or in the '238 application. Sensor 1900 may be configured and connected to detect a change in resistivity in ionically conductive piezoresistive element 1902. Suitable electrodes (not shown in FIG. 1D) may be conductively coupled to piezoresistive element 1902.

An alternating-current (AC) may be passed through conductive element 1902, and its resistivity can be measured. When pressure is applied to conductive element 1902 and conductive element 1902 is deformed by an external object such as a human finger, the resistance of conductive element 1902 changes. This change in resistance may be detected by detecting a change in either the current through conductive element 1902, or the voltage drop across a load resistor, by a signal processing circuit (not shown) connected to an amplifier (not shown).

Figure 1E:
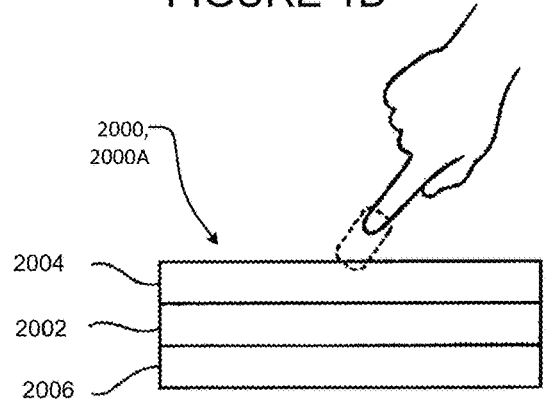
FIG. 1E is a schematic cross-sectional depiction of a capacitive pressure sensor comprising ionically conductive material according to an example embodiment of the invention.

Some aspects of the invention provide sensors incorporating capacitive pressure sensors incorporating ionically conductive materials and methods of operating and fabrication of same. Such capacitive pressure sensors exhibit a change in capacitance due to the application of pressure to and/or corresponding deformation of ionically conductive material used to provide the capacitors. FIG. 1E schematically depicts a capacitive sensor 2000 incorporating ionically conductive material according to an example embodiment. Sensor 2000 comprises a pair of ionically conductive elements 2004, 2006 disposed on either side of a dielectric layer 2002 to form a capacitor 2000A. Electric contacts, electrodes, or wires (not shown in FIG. 1E) may be provided to apply an electrical voltage and transmit electric signals from sensor 2000 to a readout circuit.

Ionically conductive elements 2004, 2006 may be fabricated from any of the ionically conductive materials (and may have any of the properties of ionically conductive materials) described herein or described in connection with any of the capacitive sensors in the '265 application or the '238 application. Dielectric layer 2002 may be fabricated using any suitable dielectric material. In selected embodiments, dielectric 2002 is fabricated from a flexible and transparent insulating polymer. By way of non-limiting example, dielectric 2002 may be fabricated from an acrylic elastomer, such as VHB™ 4905 available from 3M™. A polydimethylsiloxane (PDMS) may be used to fabricate dielectric layer 2002. Dielectric 2002 may also be fabricated using an elastomer, such as a transparent dielectric elastomer. Examples of suitable elastomers include elastic polyester materials, silicone-based elastomers, natural or synthetic rubbers, or the like. Dielectric 2002 may also be formed of a fabric material such as one based on nylon, wool, cotton, or polyester, or other fibrous materials.

Sensor 2000 may be configured and connected to a readout circuit (not shown) configured to detect both increase and decrease in capacitance of capacitor 2000A. If pressure is applied to sensor 2000 which physically deforms ionically conductive elements 2004, 2006 and/or dielectric layer 2002 of sensor 2000, the thickness of dielectric layer 2002 decreases under compression. As a result, the capacitance of sensor 2000 increases. Thus, when an increase in capacitance is detected, it can be determined that pressure has been applied to sensor 2000.

Sensors, such as the sensors illustrated in FIGS. 1A-1E may be provided in arrays comprising pluralities of individual sensing elements (or taxels) that span a sensing surface for which a pressure map is desired. In some embodiments, these pressure sensors may be distributed over a working region adjacent to (e.g. in force-transmitting contact with) the sensing surface for which a pressure map is desired.

Figure 1F:
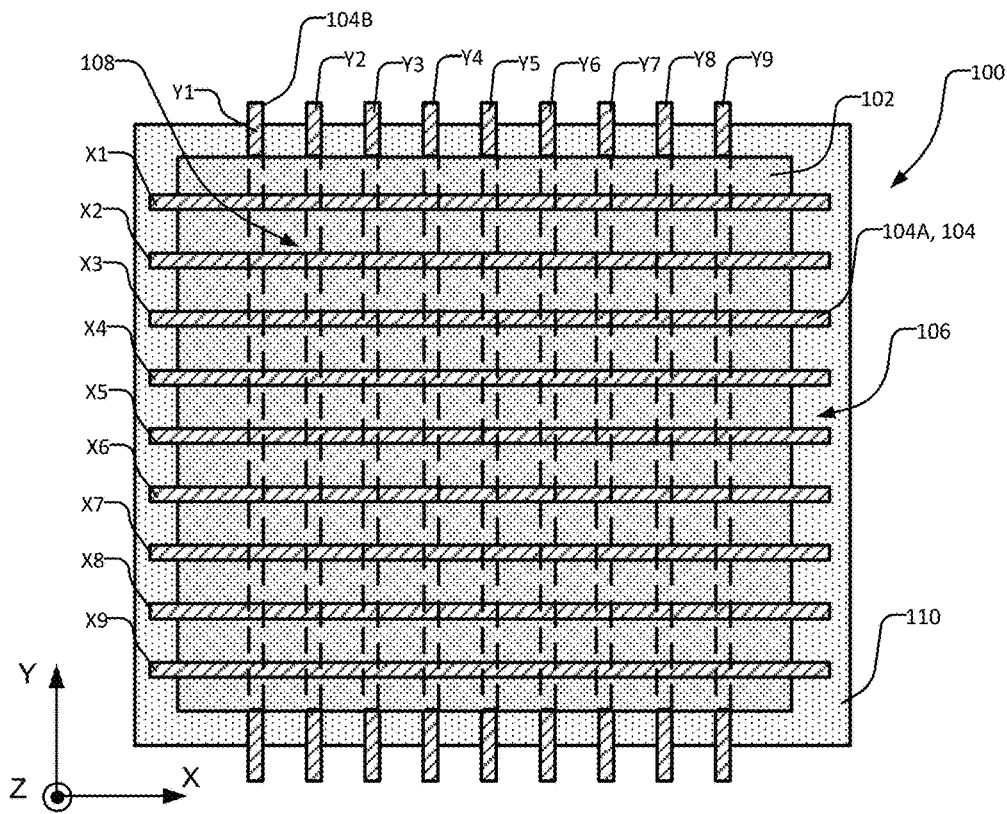
FIG. 1F is a schematic top plan view of a sensor array according to one embodiment of the invention.

FIG. 1F depicts a sensor array 100 for sensing the pressure over a sensing surface 110 according to a particular embodiment. By way of non-limiting example, sensing surface 110 may comprise or be provided on or adjacent to the surface of a bed sheet or mattress on which a person may be located (e.g. the surface of a hospital bed). The FIG. 1F sensor array 100 comprises an array of piezoionic sensing elements comprising ionically conductive material. In the illustrated FIG. 1F embodiment, sensing surface 110 (e.g. the surface being mapped) is shown as being generally planar for ease of explanation, but this is not necessary and sensing surface 110 may generally have any shape to suit a corresponding application. In the FIG. 1F embodiment, sensor array 100 is distributed over a working region 106 that is adjacent to (e.g. in force transmitting contact with) surface 110. Because sensor array 100 has some depth (shown as being in the z direction in the illustrated view of FIG. 1F), sensor array 100 is not technically distributed over a surface. However, in this description and any accompanying claims and/or aspects, references to sensors arrays and/or elements of sensor arrays being distributed over, on, relative to or otherwise in relation to a sensing surface or a surface to be mapped should be understood to refer to a working region adjacent to (e.g. in force transmitting contact with) the sensing surface (e.g. working region 106 adjacent to sensing surface 110), unless the context clearly dictates otherwise.

Sensor array 100 of the FIG. 1F embodiment comprises a piezoionic layer 102 with an array of row electrodes 104A attached to the top (positive Z) side of piezoionic layer 102 and an array of column electrodes 104B attached to the bottom (negative Z) side of piezoionic layer 102. In some embodiments, the electrodes (collectively, electrodes 104) on the same side of piezoionic layer 102 are not paired. Electrodes 104 on each (positive Z and negative Z) side of the piezoionic layer may be uniformly spaced. During use, the voltage between each row electrode 104A and each column electrode 104B may be monitored without applying any external electrical signal, such as voltage. A reference electrode is not necessary for the use of sensor 100. When sensor array 100 is touched at a location that is proximate to a particular top (positive Z) electrode 104A and a particular bottom (negative Z) electrode 104B, the voltage between these two particular electrodes 104 is expected to be larger than the voltages between other pairs of top and bottom electrodes 104.

In the illustrated embodiment, sensor array 100 comprises a first plurality of electrically conductive electrodes 104A and a second plurality of electrodes 104B (collectively, electrodes 104) which are distributed over working region 106. Electrodes 104 may be fabricated from suitable metals or other electrically conductive materials. Electrodes 104A of the FIG. 1F embodiment have an elongated shape which extends in an x-direction. Because of this elongated shape, electrodes 104A may be referred to herein as x-electrodes. Similarly, electrodes 104B of the FIG. 1E embodiment are elongated in a y-direction and may be referred to herein as y-electrodes. To help with the explanation, x-electrodes 104A are also labelled x1, x2, x3 . . . $x_n$ and y-electrodes 104B are also labelled and referred to herein as y1, 2, y3 . . . $y_m$, where n and m are any suitable positive integers, it being appreciated that the number of n of x-electrodes 104A and the number m of y-electrodes 104B may vary for particular sensing surfaces 110 and/or particular applications.

In the particular case of the FIG. 1F illustration, where sensing surface 110 is shown as being planar, the x and y directions may be considered to have generally constant spatial orientations which are the Cartesian x and y orientations shown in FIG. 1F. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 1F illustration, where sensing surface 110 is shown as being planar, the z direction shown in FIG. 1F may be considered to have generally constant spatial orientation which corresponds to the Cartesian z orientations shown in FIG. 1F. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

Sensor array 100 comprises a layer of deformable ionically conductive polymer 102 which is interposed between the array of x-electrodes 104A and the array of y-electrodes 104B and acts as a piezoionic layer as described herein. Piezoionic ionically conductive polymer layer 102 may be fabricated from suitable piezoionic ionically conductive materials, such as, by way of non-limiting example, any suitable piezoionic ionically conductive materials disclosed herein, in the '265 application or in the '238 application. Each of x-electrodes 104A overlaps a corresponding region of piezoionic (ionically conductive) layer 102 and each of y-electrodes 104B in the z-direction. In this description and any accompanying claims and/or aspects, two objects or portions of objects may be said to be overlapping in a particular direction or to overlap one another in a particular direction, when a line oriented in the particular direction (at least locally) could be drawn to intersect the two objects or portions of objects. Accordingly, it can be seen from FIG. 1F, that each of x-electrodes 104A overlaps a corresponding region of piezoionic (ionically conductive) polymer layer 102 and each of y-electrodes 104B in the z-direction. The region in which particular pair of electrodes 104A and 104B overlap one another in the z-direction may be referred to herein as an overlap region 108 and the corresponding region of piezoionic (ionically conductive) polymer layer 102 which overlaps with the pair of electrodes 104A and 104B in the z-direction may be referred to herein as the corresponding overlap region of piezoionic (ionically conductive) polymer layer 102. For ease of reference, the overlap region 108 between a particular pair of electrodes 104A and 104B may be referred to herein by the indices of the electrodes. For example, the overlap region between the x2 and y3 electrodes may be referred to as overlap region x2, y3. While sensor 100 may typically be operated by probing pairs comprising one x-electrode 104A and one y-electrode 104B, this is not necessary and pairs of electrodes 104 on the same side of piezoionic layer 102 may also be sensed in some embodiments.

Figure 7:
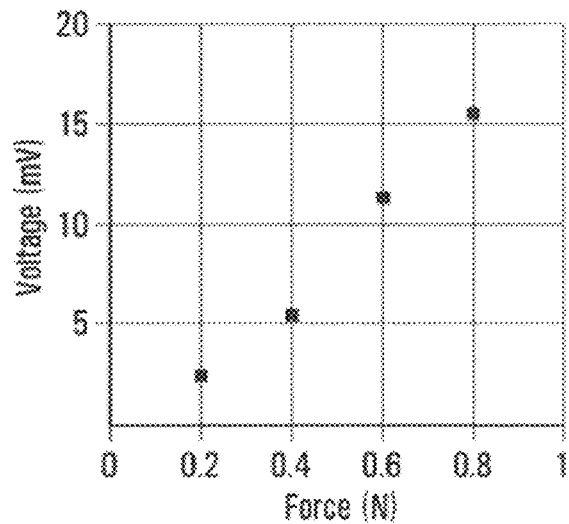
FIG. 7 is an example data graph showing representative voltage responses to pressure in a sample sensor material according to one embodiment of the invention.

A pressure sensing element may be implemented by a pair of electrodes arranged to detect electrical characteristics (e.g. a voltage between the electrodes and/or a current through the electrodes) wherein the electrical characteristics are associated with the deformation of ionically conductive polymer to which the electrodes are connected. See, for example, FIG. 7. FIG. 7 shows representative measured voltage data (amplitude response) for a pair of electrodes 104 during an application of pressure (varying at 0.1 Hz) in an overlap region corresponding to the two electrodes 104. The FIG. 7 data indicates that the test sensor response (detected voltage) was substantially linear with input force amplitude.

Figure 1G:
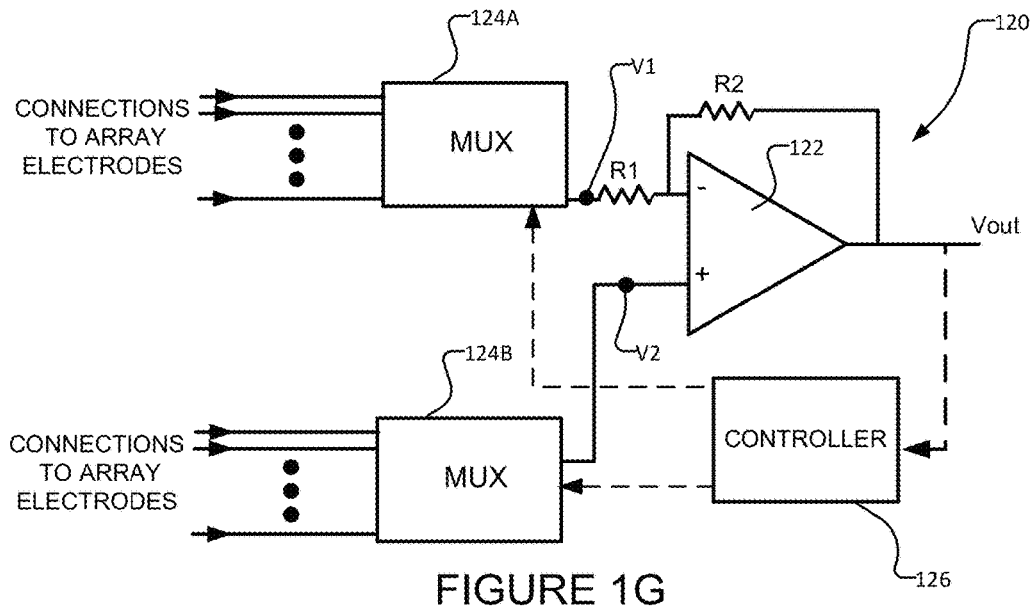
FIG. 1G is a schematic electrical circuit which may be used to detect the voltage difference between a pair of electrodes and to thereby probe the FIG. 1F sensor array according to one embodiment of the invention.

FIG. 1G shows an example electrical circuit 120 which may be used to detect the voltage difference between a pair of electrodes 104 of sensor 100. As will be appreciated by those skilled in the art, circuit 120 is a voltage amplification circuit comprising an operational amplifier 122, where the voltage $V_{out}$ is proportional the ratio of resistors R2 and R1 multiplied by the voltage difference (V2−V1) between the input connections to the sensor array (e.g. a pair of electrodes 104 of sensor array 100)—i.e.

$$V_{out} \propto \frac{R_2}{R_1}(V_2 - V_1).$$

The output voltage $V_{out}$ from circuit 120 may be provided to controller 126. It will be appreciated by those skilled in the art that circuit 120 may comprise a variety of signal conditioning elements and/or circuitry (not shown) between output voltage $V_{out}$ and controller 126. By way of non-limiting example, such signal conditioning circuitry may comprise buffers, amplifiers, filtering elements, inverters, analog to digital converters and/or the like. Controller 126 may incorporate or otherwise have access to memory in which the output values of $V_{out}$ may be stored. In some embodiments, the input nodes V1 and V2 shown in the FIG. 1G circuit 120 may be connected to any pair of electrodes 104 in the FIG. 1F sensor array 100. In some embodiments one of the input nodes V1 or V2 shown in the FIG. 1G circuit 120 may be connected to one of the electrodes 104 and the other one of the input nodes V1 and V2 may be connected to any suitable voltage reference (e.g. a ground reference or a DC voltage reference). Such connections may be effected by one or more suitable time division multiplexing (TDM) switching multiplexers (MUX) 124A, 124B which may be controlled by a suitable controller 126. In the illustrated embodiment, MUX 124A makes connections between sensor array 100 (e.g. any electrode 104 of sensor array 100 or any suitable reference voltage) and node V1 and MUX 124B makes connections between sensor array 100 (e.g. any electrode 104 of sensor array 100 or any suitable reference voltage) and node V2. The operation of MUXs 124A, 124B will be understood to those skilled in the art. In some embodiments, MUXs 124A, 124B may be implemented by a single MUX. Electrical circuit 120 is merely one example of a voltage amplification circuit suitable for determining a voltage difference between a pair of electrodes 104 in sensor array 100 or between an electrode 104 in array 100 and a suitable voltage reference. In some embodiments, other voltage amplifying circuits may be used to detect the voltage difference between a pair of electrodes 104 in array 100 or between an electrode 104 in array 100 and a suitable voltage reference.

Figure 1H:
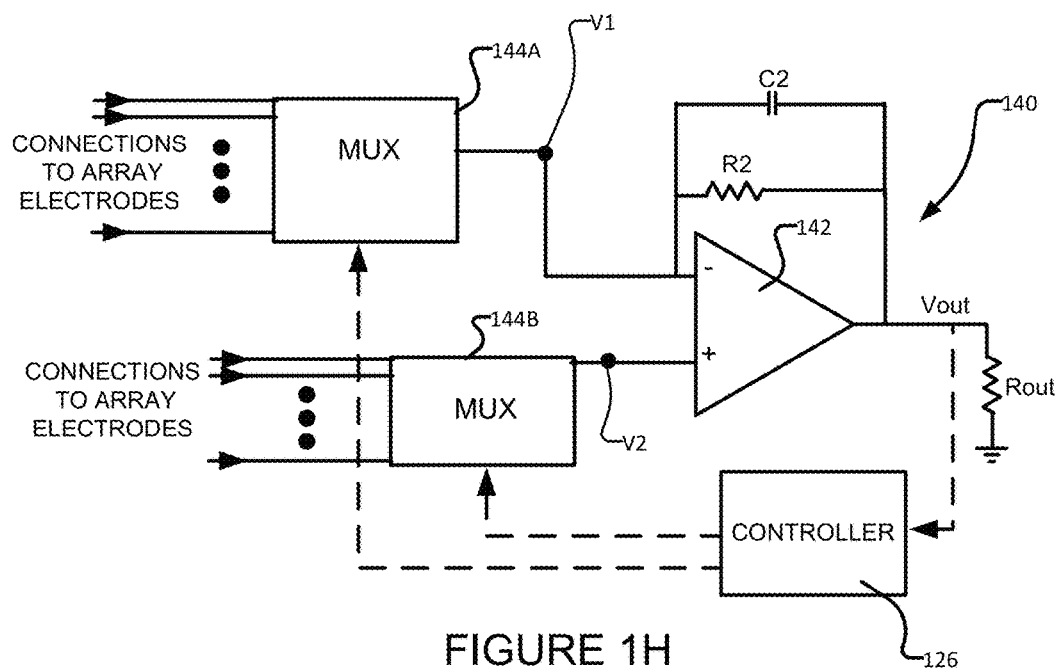
FIG. 1H is a schematic electrical circuit which may be used to detect a voltage that is representative of the current between a pair of electrodes and to thereby probe the FIG. 1F a sensor array according to one embodiment of the invention.

FIG. 1H shows an example electrical circuit 140 which may be used to detect a voltage $V_{out}$ that is representative of the current between a pair of electrodes 104 in array 100. As will be appreciated by those skilled in the art, circuit 140 is a type of charge amplification circuit comprising an operational amplifier 142. Resistor R2 may be selected to be suitably large, such that the current through feedback loop (comprising capacitor C2 and resistor R2) is principally attributed to a ratio between C2 and the impedance between the positive and negative input leads to amplifier 142. Consequently, the voltage output signal $V_{out}$ is proportional to this current multiplied by output resistor Rout. The output voltage $V_{out}$ from circuit 140 may be provided to controller 126. It will be appreciated by those skilled in the art that circuit 140 may comprise a variety of signal conditioning elements and/or circuitry (not shown) between output voltage $V_{out}$ and controller 126. By way of non-limiting example, such signal conditioning circuitry may comprise buffers, amplifiers, filtering elements, inverters, analog to digital converters and/or the like. Controller 126 may incorporate or otherwise have access to memory in which the output values of $V_{out}$ may be stored. For the current amplifier circuit 140 of FIG. 1H, it may be shown that the Laplace domain transfer function may be given by:

$$H(s) = \frac{V_{out}(s)}{V_{in}(s)} = \frac{sR_2 C_{in}}{1 + sR_2 C_2} \quad (1)$$

where $V_{in}(s)$ and $C_{in}$ are respectively the voltage and capacitance between a pair of electrodes 104 in sensor array 100 (or between an electrode in array 100 and a voltage reference) which may be connected to nodes V1 and V2. $C_{in}$ will be relatively constant (and is experimentally determinable or calibratable) for various pairs of electrodes 104 in sensor array 100. Accordingly, the equation (1) transfer function may be used to determine $V_{in}$ (i.e. the voltage between a pair of electrodes 104 in sensor array 100) by measuring $V_{out}$. In some embodiments, the input nodes V1 and V2 shown in the FIG. 1H circuit 140 may be connected to any pair of electrodes 104 in the FIG. 1F sensor array 100. In some embodiments one of the input nodes V1 or V2 shown in the FIG. 1H circuit 140 may be connected to one of the electrodes 104 and the other one of the input nodes V1 and V2 may be connected to any suitable voltage reference (e.g. a ground reference or a DC voltage reference). Such connections may be effected by one or more suitable time division multiplexing (TDM) switching multiplexers (MUX) 144A, 144B which may be controlled by a suitable controller 126. In the illustrated embodiment, MUX 144A makes connections between sensor array 100 (e.g. any electrode 104 of sensor array 100 or any suitable reference voltage) and node V1 and MUX 144B makes connections between sensor array 100 (e.g. any electrode 104 of sensor array 100 or any suitable reference voltage) and node V2. The operation of MUXs 144A, 144B will be understood to those skilled in the art. In some embodiments, MUXs 144A, 144B may be implemented by a single MUX. Electrical circuit 140 is merely one example of a charge amplification circuit suitable for determining a current flow between a pair of electrodes 104 in sensor array 100 or between an electrode 104 in array 100 and a suitable voltage reference (and an output voltage $V_{out}$ corresponding to this current flow). In some embodiments, other charge amplifying circuits may be used to detect current flow between a pair of electrodes 104 in sensor array 100 or between an electrode 104 in array 100 and a suitable voltage reference (and an output voltage $V_{out}$ corresponding to this current flow).

Figure 2A:
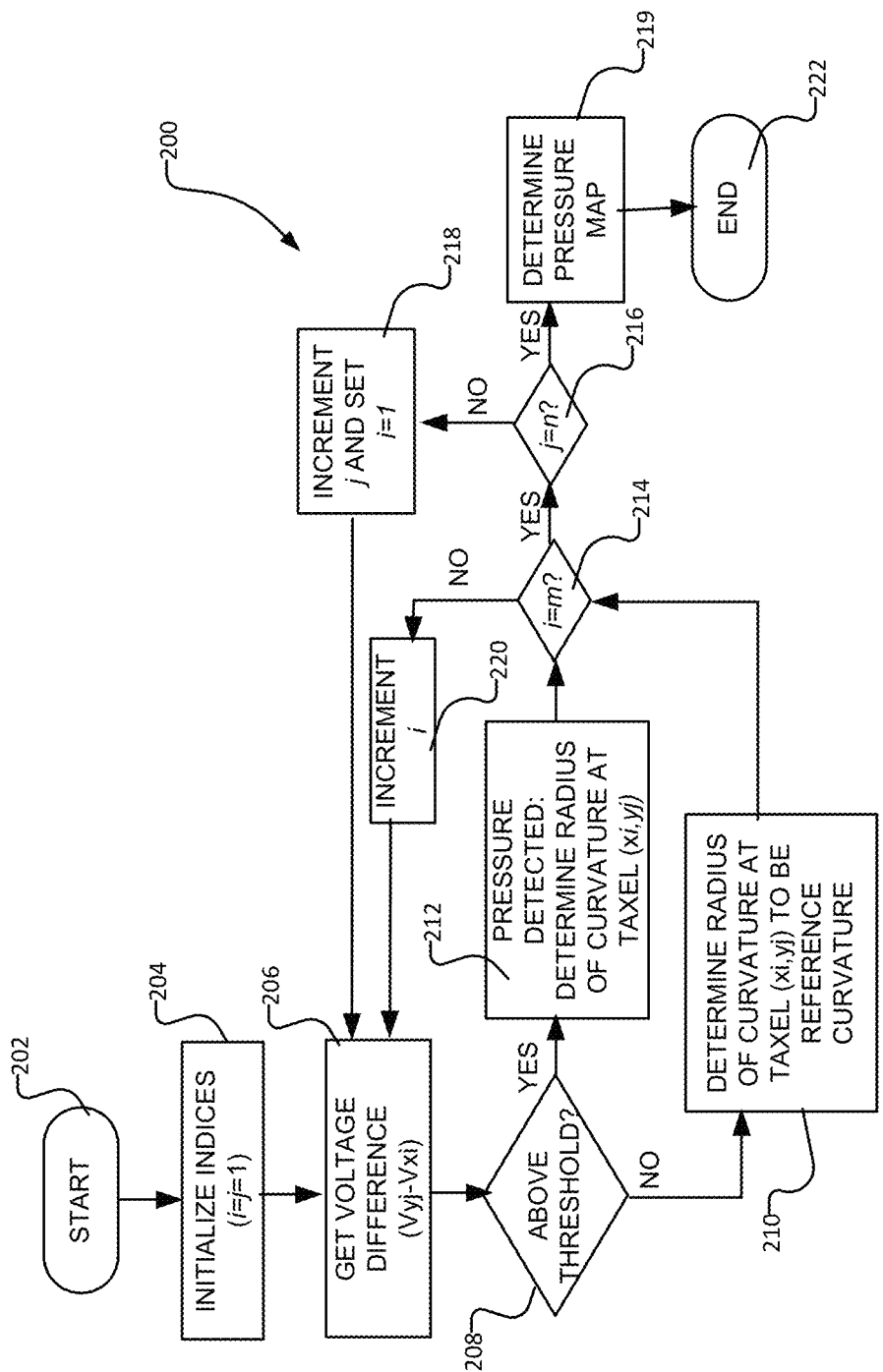
FIG. 2A is a block diagram of a method for creating a pressure map over a sensing surface according to one embodiment of the invention.

FIG. 2A is a schematic illustration of a method 200 for reading out the electrical characteristics from pairs of individual electrodes 104 in the FIG. 1F sensor array 100 to obtain a pressure map over sensing surface 110 according to a particular embodiment. Method 200 may be implemented (or at least controlled) by controller 126 (see FIGS. 1G and 1H). Method 200 involves detecting voltages between pairs of electrodes 104 that overlap one another in the z-direction. More particularly, in method 200 of the FIG. 2A embodiment, a pressure is obtained for each overlap region $(x_i,y_j)$ corresponding to the overlap region between an x-electrode $x_i$ and a y-electrode $y_j$. It will be appreciated that when a force is applied to surface 110 in a vicinity of overlap region $(x_i,y_j)$, the deformations of the corresponding electrodes $x_i$ and $y_j$ may be different from one another. For example, if a curvature is applied to the array in a vicinity of an overlap region $(x_i,y_j)$, then, because of the thickness of the array structure, the two surfaces of the array structure will have different radii of curvature. Typically, piezoionic (ionically conductive) layer 102 will be bonded or otherwise adhered to electrodes 104, such that piezoionic (ionically conductive) layer 102 and electrodes 104 may experience the same local strain. Accordingly, the differential deformation between the corresponding surfaces of piezoionic (ionically conductive) layer 102 may also be different, thereby altering the ion distribution in the overlap region $(x_i,y_j)$ of piezoionic (ionically conductive) layer 102 and generating detectable voltage and/or current characteristics as described above in relation to FIGS. 1C and 1D. The Applicant has demonstrated that these electrical characteristics are at least approximately linearly related to the applied force (and/or the applied pressure), at least under certain conditions—see, for example, FIG. 7. Without wishing to be bound by theory, the voltage between an x-electrode $x_i$ and a y-electrode $y_j$ in an overlap region $(x_i,y_j)$ may be demonstrated to be at least approximately linearly related to the difference in radius of curvature between the x-electrode $x_i$ and a y-electrode $y_j$. If the x-y area of the taxel (overlap region $(x_i,y_j)$) is sufficiently small then this difference in radius of curvature may be approximately linearly related to the strain of the corresponding region of piezoionic layer 102, which may be in turn linearly related to the stress (force) on the region of piezoionic layer 102 (assuming that the material is at least approximately elastic) and this stress force may be linearly related to the pressure in the overlap region $(x_i,y_j)$ in dependence on the area of the overlap region $(x_i,y_j)$. Note that the totality of this relationship (between voltage between an x-electrode $x_i$ and a y-electrode $y_j$ in an overlap region $(x_i,y_j)$ and the pressure on the overlap region $(x_i,y_j)$) need not be linear and this relationship may, in general, be empirically or experimentally determined.

After commencing in block 202, method 200 of FIG. 2A proceeds to block 204 which involves initializing the loop indices i and j, which correspond respectively to the x-electrode and y-electrode indices, to i=j=1. In the FIG. 2A embodiment, it is assumed that the total number of x-electrodes 104A is m and the total number of y-electrodes is n. It will be appreciated as discussed above, that m and n are arbitrary positive integers which may vary for particular sensing surfaces 110 and/or particular applications. Method 200 then proceeds to block 206 which involves obtaining a voltage difference between the x and y electrodes 104 corresponding to the current overlap region $(x_i,y_j)$—i.e. between the x-electrode $x_i$ and y-electrode $y_j$. Block 206 may be effected (using voltage amplification circuit 120 of FIG. 1G or some other suitable voltage amplification circuit) by causing MUX 124 to effect connections to x-electrode $x_i$ and y-electrode $y_j$ and measuring $V_{out}=(v_{yj}-v_{xi})$. Additionally or alternatively, as discussed above, block 206 may be effected (using voltage amplification circuit 120 of FIG. 1G or some other suitable voltage amplification circuit) by causing MUX 124 to effect connections which measure the voltage on x-electrode $x_i$ relative to a known or common reference and the voltage on y-electrode $y_j$ relative to a known or common reference and then removing the reference voltage from each signal and subtracting the difference to arrive at $(v_{yj}-v_{xi})$. Block 206 may additionally or alternatively involve current measurements in respect of the current overlap region (xi,yi) using charge amplification circuit 120 of FIG. 1H or some other suitable charge amplification circuit.

Method then proceeds to block 208 which involves an inquiry as to whether the measured voltage difference $(v_{yj}-v_{xi})$ is above some suitable cut-off threshold, which may be configurable and/or calibratable for particular embodiments and/or applications. The block 208 threshold may be a threshold designed to eliminate false positive readings due to noise, variations in atmospheric pressure, variations in temperature and/or the like. If the block 206 measured voltage difference $(v_{yj}-v_{xi})$ is less than this threshold (block 208 NO result), then method 200 proceeds to block 210. In block 210, method 200 assigns a nominal differential radius of curvature to the current overlapping x and y electrodes $(x_i,y_j)$. This nominal differential curvature may be zero. If the block 206 measured voltage difference $(v_{yj}-v_{xi})$ is greater than the threshold (block 208 YES result), then method 200 proceeds to block 212 which involves estimating a difference in radii of curvature between the current x and y electrodes corresponding to the current overlap region $(x_i,y_j)$. As discussed above, the voltage difference $(v_{yj}-v_{xi})$ may be at least approximately related to this difference in radii of curvature. Determining the difference in radii of curvature in bock 212 may comprise applying a suitable scaling factor α to the block 206 current measured voltage difference $(v_{yj}-v_{xi})$. The scaling factor α may be experimentally determined for particular embodiments or otherwise calibrated for particular embodiments and/or applications. It is not strictly necessary that determining the difference in radii of curvature in bock 212 involve only scaling. Other relationships, between the block 206 measured voltage difference ($v_{yj}-v_{xi}$) and the radii of curvature, the applied force and/or the applied pressure at the current overlap region ($x_i,y_j$), may be experimentally determined and then used in block 212 to determine the radii of curvature, the applied force and/or the applied pressure at the current overlap region ($x_i,y_j$).

Whether via block 210 or block 212, method 200 proceeds to block 214 which involves an inquiry as to whether the current x-electrode index i is equal to the maximum number m of x-electrodes. If the block 214 inquiry is negative, the x-electrode index i is incremented in block 220 before looping back to block 206 with a new x-index. If the block 214 inquiry is positive, the y-electrode index j is incremented in block 218 before looping back to block 206 with a new y-index, unless the current y-electrode index j is equal to the maximum number n of y-electrodes (block 216 NO branch) in which case method 200 ends in block 222. It will be appreciated from the logic of method 200 that method 200 involves looping through the x-electrodes $x_1$, $x_2, x_3 \ldots x_n$ for a given y-electrode $y_j$ and then incrementing the y-electrode and repeating the x-electrode loop, until all of the overlap regions ($x_i,y_j$) have been assigned an estimated difference in radii of curvature a map for sensing surface 110 of this radii of curvature difference is obtained. Method 200 then proceeds to block 219, where the map of radii of curvature over sensing surface 110 is converted into a map of strain (e.g. depression) over sensing surface 110 which is then correlated to the applied pressure to obtain a pressure map corresponding to sensing surface 110. Method 200 then proceeds to block 222 which may involve saving the pressure map to a memory accessible to controller 126 or otherwise further processing the pressure map obtained by method 200.

Method 200 may be repeated with any suitable frequency for determining pressure maps of interest. For example, in one particular embodiment, where sensing surface 110 may comprise or be provided on or adjacent to the surface of a bed sheet or mattress on which a person may be located (e.g. the surface of a hospital bed), it may be desirable to detect pressure fluctuation corresponding to a heart rate and/or a respiratory rate of a person located on the mattress. In such cases, it may be desirable to repeat method 200 with a frequency that is suitably fast to detect a maximum desired heart rate. For example, a suitable sampling frequency may be on the order of 10-20 Hz. As another example, in one particular embodiment, where sensing surface 110 may comprise the surface of electronic device where pressure may be used to interact with a graphical user interface, it may be desirable to detect pressure changes at higher rates corresponding to rates at which a person may move their fingers relative to surface 110. For example, a suitable sampling frequency may be on the order of 60-120 Hz.

Figure 2B:
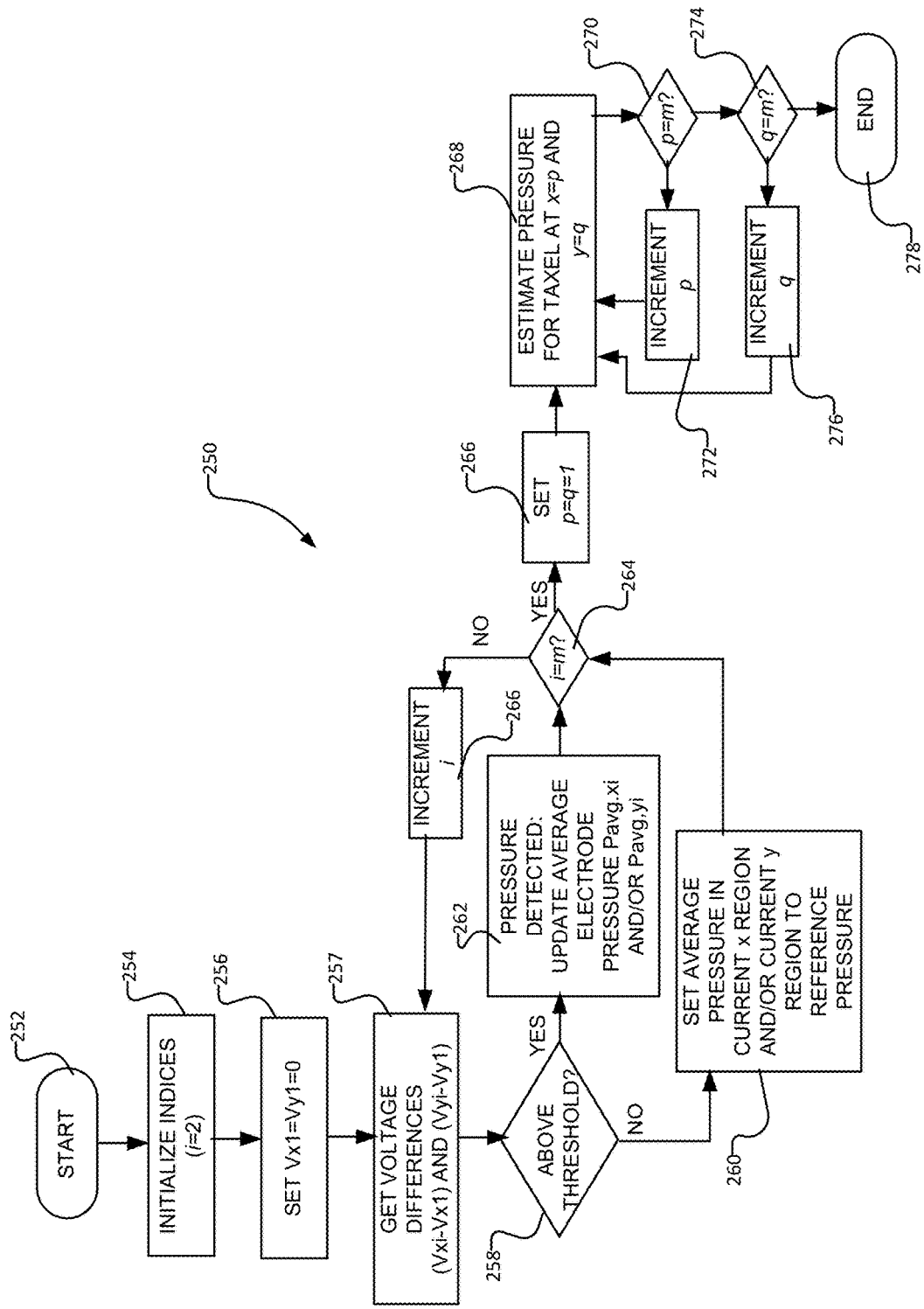
FIG. 2B is a block diagram of a method for creating a pressure map over a sensing surface according to another embodiment of the invention.

FIG. 2B is a schematic illustration of another method 250 for reading out the electrical characteristics from individual electrodes 104 in the FIG. 1F sensor array 100 to obtain a pressure map over sensing surface 110 according to another particular embodiment. Method 250 may be implemented (or at least controlled) by controller 126 (see FIGS. 1G and 1H). As will be described in more detail below, method 250 involves: detecting voltages between individual x and y electrodes 104 and reference x and y electrodes and then using those voltages to determine a pressure estimate or for each overlap region ($x_i,y_j$) corresponding to the overlap region between an x-electrode $x_i$ and a y-electrode $y_j$. Without wishing to be bound by theory, the inventors have determined that the voltage between an x-electrode $x_i$ or a y-electrode $y_j$ is related to the total force applied in a vicinity of the x-electrode $x_i$ or the y-electrode $y_j$—see the discussion of FIG. 7 herein.

Method 250 of FIG. 2B is now explained. After commencing in block 252, method 250 of FIG. 2B proceeds to block 254 which involves initializing the loop index i to i=2. In the FIG. 2B embodiment, it is assumed (for ease of explanation and without loss of generality) that the number x-electrodes and y-electrodes is the same and is equal to m. In the first portion of method 250, the index i may be used to index both the x and y electrodes. Method 200 then proceeds to block 256 which involves setting a reference x-electrode (e.g. $x_1$) and a reference y-electrode (e.g. $y_i$) to be at a reference (e.g. zero) potential—e.g. setting $v_{x1}=v_{x2}=0$ or to some other suitable reference. This may be done, by way of non-limiting example, by ensuring that for a particular application or geometry, the pressures applied at the reference electrodes are likely to be at, or close to, atmospheric or to some other reference pressure (e.g. the reference electrodes are located in some location (relative to the desired sensing region of sensing surface 110, where they are unlikely to experience, and/or are physically isolated from, varying external pressure). Additionally or alternatively, this may involve connecting the reference electrodes to a ground of the sensing circuitry or to some other reference voltage source at a particular reference potential.

Method 250 then proceeds to block 257 which involves obtaining two voltage differences—a first voltage difference $v_{xi}-v_{x1}$ between the current x-electrode $x_i$ and the reference x-electrode $x_1$; and a second voltage difference $v_{yi}-v_{y1}$ between the current y-electrode $y_i$ and the reference y-electrode $y_1$. Block 257 may be effected (using voltage amplification circuit 120 of FIG. 1G or some other suitable voltage amplification circuit) by: causing MUX 124 to effect connections to x-electrodes $x_i$, $x_1$ and measuring $V_{out}=(v_{xi}-v_{x1})$; and causing MUX 124 to effect connections to y-electrodes $y_i$, $y_1$ and measuring $V_{out}=(v_{yi}-v_{y1})$. Block 257 may additionally or alternatively involve current measurements in respect of the current between the current x-electrode $x_i$ and the reference x-electrode $x_1$; and the current between the current y-electrode $y_i$ and the reference y-electrode $y_1$ using charge amplification circuit 120 of FIG. 1H or some other suitable charge amplification circuit.

Method 250 then proceeds to block 258 which involves an inquiry as to whether the measured voltage differences ($v_{xi}-v_{x1}$) and/or ($v_{yi}-v_{y1}$) are above some suitable cut-off threshold, which may be configurable and/or calibratable for particular embodiments and/or applications. The block 258 threshold may be a threshold designed to eliminate false positive readings due to noise, variations in atmospheric pressure, variations in temperature and/or the like. If the block 257 measured voltage differences ($v_{xi}-v_{x1}$) and/or ($v_{yi}-v_{y1}$) are less than this threshold (block 258 NO result), then method 250 proceeds to block 260 for that electrode. In the illustrated embodiment, block 260 involves the assumption that there is no average external pressure above the reference pressure associated with electrodes $x_1$, $y_1$ (e.g. no average pressure above atmospheric) in a region corresponding to the current x-electrode $x_i$ and/or in a region of the current y-electrode $y_i$. If the block 257 measured voltage differences ($v_{xi}-v_{x1}$) and/or ($v_{yi}-v_{y1}$) are greater than the threshold (block 258 YES result), then method 250 proceeds to block 262 for that electrode. Block 262 involves determining the average pressure in the region between the current x-electrode $x_i$ and the reference x-electrode $x_1$ (which may be referred to herein as $P_{avg,xi}$) and/or determining the average pressure in the region between the current y-electrode $y_i$ and the reference y-electrode $y_1$ (which may be referred to herein as $P_{avg,yi}$). As discussed elsewhere herein, the inventors have determined that the voltage between an x-electrode $x_i$ or a y-electrode $y_i$ is related to the total force applied in a vicinity of the x-electrode $x_i$ or the y-electrode $y_j$—see above discussion of FIG. 2A. The total force divided by the total cross-sectional area yields the average pressure $P_{avg,xi}$, $P_{avg,yi}$. Using this relationship, the average pressures in a vicinity of the current x-electrode $x_i$ or a y-electrode $y_i$ may be determined from the voltage differences $(v_{xi}-v_{x1})$ and $(v_{yi}-v_{y1})$. The relationships, between the block 257 measured voltage differences $(v_{xi}-v_{x1})$ and $(v_{yi}-v_{y1})$ and the applied force (and/or the average applied pressures $P_{avg,xi}$ and $P_{avg,yi}$) in the current x-region $(x_i-x_1)$ and the current y-region $(y_i-y_1)$, may be experimentally or empirically determined and then used in block 262 to determine the average pressures $P_{avg,xi}$ and $P_{avg,yi}$. The procedures of blocks 258, 260 and 262 are shown in FIG. 2B as occurring for both the current x-electrode $x_i$ and the current y-electrode $y_i$ at the same time. However, in practice, these blocks may be performed separately for the current x-electrode $x_i$ and the current y-electrode $y_i$. For example, the current x-electrode $x_i$ may end up in block 260, whereas the y-electrode $y_i$ may end up in block 262.

Whether via block 260 or block 262, method 250 proceeds to block 264 which involves an inquiry as to whether the current electrode index i is equal to the maximum number m of electrodes 104. If the block 264 inquiry is negative, the electrode index i is incremented in block 266 before looping back to block 257 with a new electrode index. If the block 264 inquiry is positive, then method 250 proceeds to block 266 which involves initializing another pair of loop indices p, q to be p=q=1 before proceeding to block 268. Block 268 involves determining a pressure estimate $P_{p,q}$ for a taxel (region) corresponding to the current x index (x=p) and current y index (y=q) based at least in part on the average row and column pressures determined in blocks 260, 262. The details of one particular, non-limiting implementation of block 268 are described in more detail below. It will be appreciated, however, from the logic of blocks 270, 272, 274, 276, that method 250 loops through the regions (e.g. taxels) corresponding to each overlapping pair of electrodes 104 and determines a pressure $P_{p,q}$ for p=1, 2 . . . m and q=1, 2 . . . m. When each such pressure estimate $P_{p,q}$ is determined and a pressure map for sensing surface 110 is obtained, method 250 concludes in block 278. Block 278 may involve saving the pressure to a memory accessible to controller 126 or otherwise further processing the pressure map obtained by method 250. Like method 200 described above, method 250 may repeated with any suitable frequency for determining pressure maps of interest.

Figure 2C:
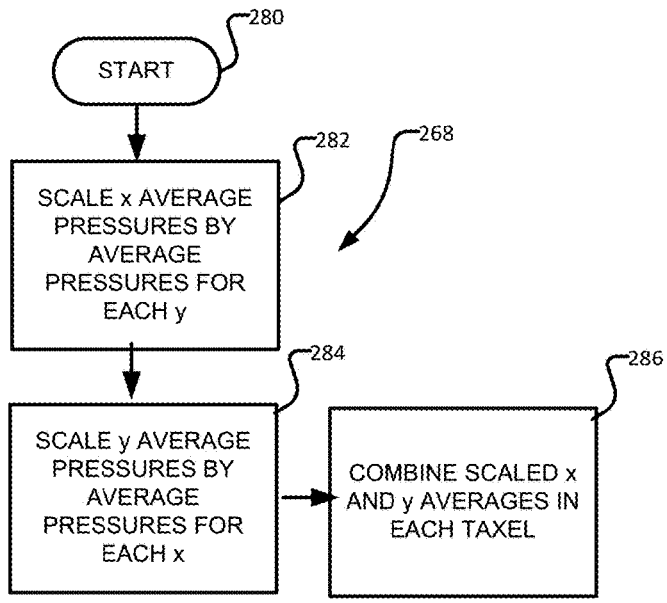
FIG. 2C is a block diagram of a method for scaling average pressure values according to one embodiment of the invention.
Figure 2D:
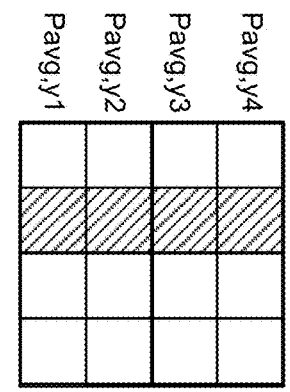
FIG. 2D is a schematic depiction of an example scaling/contouring process for a particular row of a sensor array according to one embodiment of the invention.

One particular, non-limiting implementation of block 268 is now explained in more detail. FIG. 2C illustrates a method for implementing block 268 according to a particular embodiment. After commencing in block 280, method 268 proceeds to block 282 which involves using the average y-electrode pressures ($P_{avg,yq}$ for q=1, 2 . . . m) to scale (e.g. contour) the average x-electrode pressures ($P_{avg,xp}$ for p=1, 2 . . . m). FIG. 2D illustrates an example of this block 282 scaling/contouring process for a particular row x=2. As discussed above, the average pressure in row x=2 ($P_{avg,x2}$) is determined in block 262 (or to be atmospheric in block 260). In block 282, this average pressure in row x=2 is contoured for each taxel (x=2, y=q for q=1, 2 . . . m) by scaling the average pressure in row x=2 ($P_{avg,x2}$) by a scaling factor which depends on the average pressure in a corresponding column y=q ($P_{avg,yq}$) for q=1, 2 . . . m. In some embodiments, this scaling factor is a ratio of the average pressure in a corresponding column y=q ($P_{avg,yq}$) for q=1, 2 . . . m over sum of the average pressures over all columns ($\Sigma_{q=1}^{m} P_{avg,yq}$)—i.e. the scaling factor for column y=q is given by $$\frac{P_{avg,yq}}{\sum_{q=1}^{m} P_{avg,yq}}.$$

In block 282, this procedure is implemented for each row x=p for p=1, 2 . . . m. Method 268 then proceeds to block 284 which involves using the average x-electrode pressures ($P_{avg,xp}$ for p=1, 2 . . . m) to scale (e.g. contour) the average y-electrode pressures ($P_{avg,yq}$ for q=1, 2 . . . m). This block 284 may be similar to the block 282 procedure, except the rows are used to scale the column values in block 284 (whereas the column values were used to scale the row values in block 282).

Figure 2E:
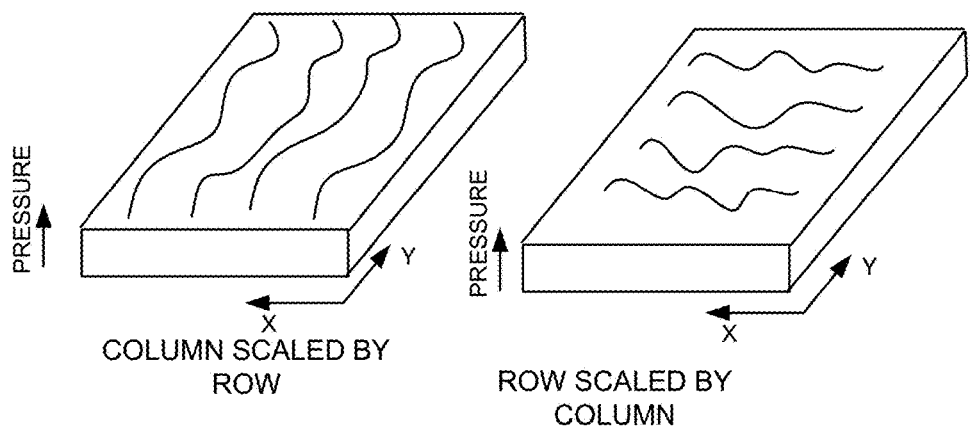
FIG. 2E is a schematic depiction of an example of the scaling process used in the method of FIG. 2C.

The output of blocks 282 and 284 is shown in FIG. 2E. In particular, blocks 282 and 284 result in two pressure values for each taxel corresponding to x=p,y=q: one value that results from the block 282 scaling of each row by each column (shown in the right hand side of FIG. 2E); and one value that results from the block 284 scaling of each column by each row (shown in the left hand side of FIG. 2E). Method 268 may then proceed to block 286 which involves estimating the pressure for a particular taxel corresponding to x=p,y=q to be the average of the value determined in block 282 and the value determined in block 284—i.e. the average of the two maps shown in FIG. 2E.

Method 248 (and block 248) may be summarized by the equation:

$$P_{final(x=p,y=q)} = \frac{P_{avg,xp}\left(\frac{P_{avg,yq}}{\sum Pavg, y}\right) + P_{avg,yq}\left(\frac{P_{avg,xp}}{\sum Pavg, x}\right)}{2} \quad (9)$$

where: $P_{final(x=p,y=q)}$ is the final output of block 248 (and method 250) for the taxel (x=p,y=q); $P_{avg,xp}$ and $P_{avg,yq}$ have the meanings discussed above; and the sums are taken over all rows and columns. In some embodiments, the pressures $P_{p,q}$ for particular taxels (regions) determined according to the FIG. 2C embodiment may be further processed (e.g. scaled, offset and/or otherwise calibrated) to obtain modified pressures $P_{p,q}$ for particular taxels which more closely represent actual pressure values. Such further processing techniques can be determined experimentally.

The above-described implementation of block 268 is not necessary. In other embodiments, other techniques may be used to estimate the local pressures $P_{p,q}$ for taxels (regions) corresponding to the current x index (x=p) and current y index (y=q) based at least in part on the average row and column pressures (e.g. those average pressure determined in blocks 260, 262).

Figure 3A:
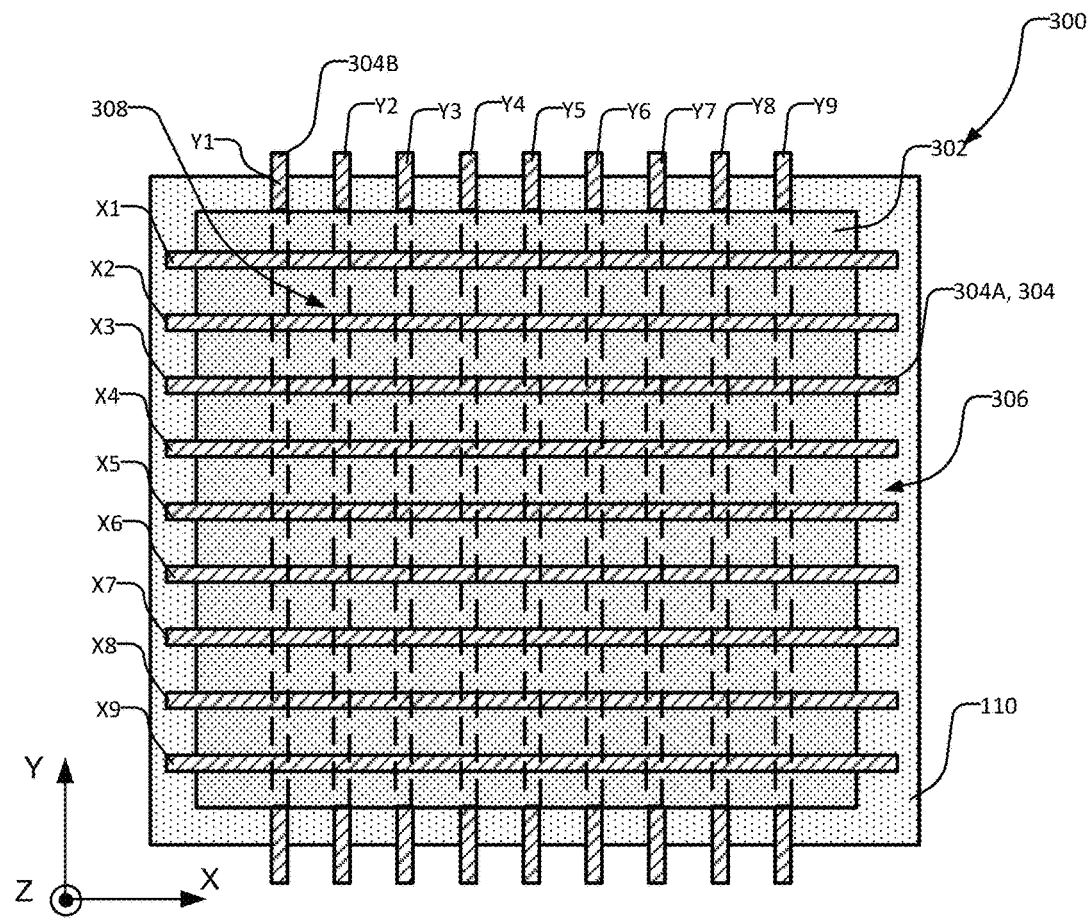
FIG. 3A is a schematic top plan view of a sensor array according to another embodiment of the invention.

FIG. 3A depicts a sensor array 300 for sensing the pressure over a sensing surface 110 according to another particular embodiment. By way of non-limiting example, sensing surface 110 may comprise or be provided on or adjacent to the surface of a bed sheet or mattress on which a person may be located (e.g. the surface of a hospital bed). The FIG. 3A sensor array 300 comprises an array of capacitive sensing elements comprising ionically conductive material. In the illustrated FIG. 3A embodiment, sensing surface 110 being mapped is shown as being generally planar for ease of explanation, but this is not necessary and sensing surface 110 may generally have any shape to suit a corresponding application. In the FIG. 3A embodiment, sensor array 300 is distributed over a working region 306 that is adjacent to (e.g. in force-transmitting contact with) sensing surface 110. Because sensor array 300 has some depth (shown as being in the z direction in the illustrated view of FIG. 3A), sensor array 300 is not technically distributed over a surface. However, in this description and any accompanying claims and/or aspects, references to sensors arrays and/or elements of sensor arrays being distributed over, on, relative to or otherwise in relation to the surface to be mapped should be understood to refer to a working region adjacent to (e.g. in force-transmitting contact with) the surface (e.g. working region 306 adjacent to sensing surface 110), unless the context clearly dictates otherwise.

Sensor array 300 comprises a first plurality of ionically conductive electrodes 304A and a second plurality of ionically conductive electrodes 304B (collectively, electrodes 304) which are distributed over working region 306. Electrodes 304 may be fabricated from suitable ionically conductive materials, such as, by way of non-limiting example, any suitable ionically conductive materials disclosed herein, in the '265 application or in the '238 application. Electrodes 304A of the FIG. 3A embodiment have an elongated shape which extends in an x-direction. Because of this elongated shape, electrodes 304A may be referred to herein as x-electrodes. Similarly, electrodes 304B of the FIG. 3A embodiment are elongated in a y-direction and may be referred to herein as y-electrodes. To help with the explanation, x-electrodes 304A are also labelled x1, x2, x3 . . . $x_n$ and y-electrodes 304B are also labelled and referred to herein as y1, 2, y3 . . . $y_m$, where n and m are any suitable positive integers, it being appreciated that the number of n of x-electrodes 304A and the number m of y-electrodes 304B may vary for particular sensing surfaces 110 and/or particular applications.

In the particular case of the FIG. 3A illustration, where sensing surface 110 is shown as being planar, the x and y directions may be considered to have generally constant spatial orientations which are the Cartesian x and y orientations shown in FIG. 3A. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 3A illustration, where sensing surface 110 is shown as being planar, the z direction shown in FIG. 3A may be considered to have generally constant spatial orientation which corresponds to the Cartesian z orientations shown in FIG. 3A. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

Sensor array 300 of the FIG. 3A embodiment comprises a contiguous dielectric layer 302 which is interposed between the array of ionically conductive x-electrodes 304A and the array of ionically conductive y-electrodes 304B. Dielectric layer 302 may be fabricated from suitable materials, such as, by way of non-limiting example, any suitable deformable dielectric materials disclosed herein, in the '265 application or in the '238 application. Each of x-electrodes 304A overlaps a corresponding region of dielectric layer 302 and each of y-electrodes 304B in the z-direction. The region in which particular pair of electrodes 304A and 304B overlap one another in the z-direction may be referred to herein as an overlap region 308 and the corresponding region of dielectric layer 302 which overlaps with the pair of electrodes 304A and 304B in the z-direction may be referred to herein as the corresponding overlap region of dielectric layer 302. For ease of reference, the overlap region 308 between a particular pair of electrodes 304A and 304B may be referred to herein by the indices of the electrodes. For example, the overlap region between the x2 and y3 electrodes may be referred to as overlap region x2, y3.

Figure 3B:
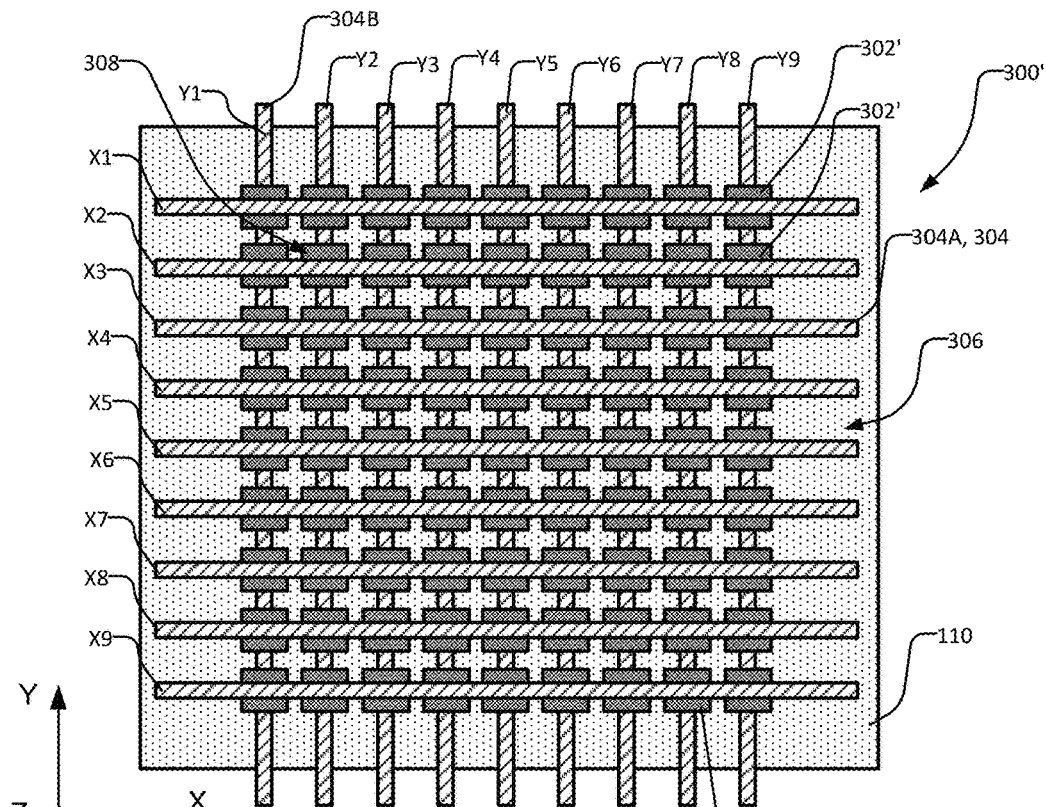
FIG. 3B is a schematic top plan view of a sensor array according to another embodiment of the invention.

FIG. 3B depicts a sensor array 300' for sensing the pressure over a sensing surface 110 according to another particular embodiment. Sensor array 300' is similar to sensor array 300 in many respects and similar reference numerals are used to describe features of sensor array 300' which are similar to those of sensor array 300. Like sensor array 300, the FIG. 3B sensor array 300' comprises an array of capacitive sensing elements comprising ionically conductive material. Sensor array 300' of FIG. 3B differs from sensor array 300 of FIG. 3A primarily in that the dielectric layer of sensor array 300' is spatially divided into a plurality of spaced apart dielectric layer elements 302'. Each dielectric layer element 302' is located in a vicinity of a corresponding overlap region and is interposed between a corresponding ionically conductive x-electrode 304A and a corresponding ionically conductive y-electrode 304B, such that an x-electrode 304A, a y-electrode 304B and a dielectric layer element 302' overlap each other in the z-direction in each overlap region. In other respects, sensor array 300' is similar to sensor array 300 and, unless the context dictates otherwise, the portion of this description applicable to sensor array 300 should be considered to be applicable to sensor array 300'.

As discussed above in connection with FIG. 1E, a capacitive pressure sensing element may be implemented by a capacitor comprising a pair of ionically conductive electrodes, wherein there is an estimatable relationship between the capacitance of the capacitive sensing element and the deformation of the capacitor (e.g. deformation of the ionically conductive polymer layers and/or the deformable dielectric) and a corresponding relationship between the capacitance of the capacitive sensing element and the pressure in a vicinity of the capacitive sensing element. Without wishing to be bound by theory, a derivation is presented to demonstrate that, under certain assumptions, the capacitance between an x-electrode $x_i$ and a y-electrode $y_j$ of sensor array 300 is a function of (e.g. inversely correlated with) the pressure in a vicinity of the overlap region between x-electrode $x_i$ and y-electrode $y_j$ (i.e. overlap region $(x_i, y_j)$). Consider an overlap region $(x_i, y_j)$ having a dielectric region with a nominal thickness $t_0$ (in the z-direction) and a cross-sectional area A (in the x and y directions). The pressure P on the overlap region is given by P=F/A where F is the external force. The Young's modulus Y associated with a change in thickness Δt of the dielectric region is given by:

$$Y = \frac{P}{\frac{\Delta t}{t_0}} \qquad (10)$$

The capacitance of a capacitor generally is given by:

$$C = \frac{\epsilon A}{t} \quad (11)$$

where $\epsilon$ is the dielectric constant of the dielectric material and t is the time varying thickness of the dielectric layer. Recognizing that $t = t_o - \Delta t$, equations (10) and (11) may be combined to obtain:

$$C = \frac{\epsilon A}{\left(t_0 - \frac{P}{Y} \cdot t_0\right)} \quad (12)$$

Equation (12) demonstrates that in this example, the capacitance is inversely correlated with the pressure applied in a vicinity of the overlap region $(x_i, y_j)$ by a first order linear equation. In general, however, the relationship between the capacitance and pressure in an overlap region is not limited to this exemplary derivation and this relationship may be determined (e.g. experimentally) for any particular applications.

Figure 3C:
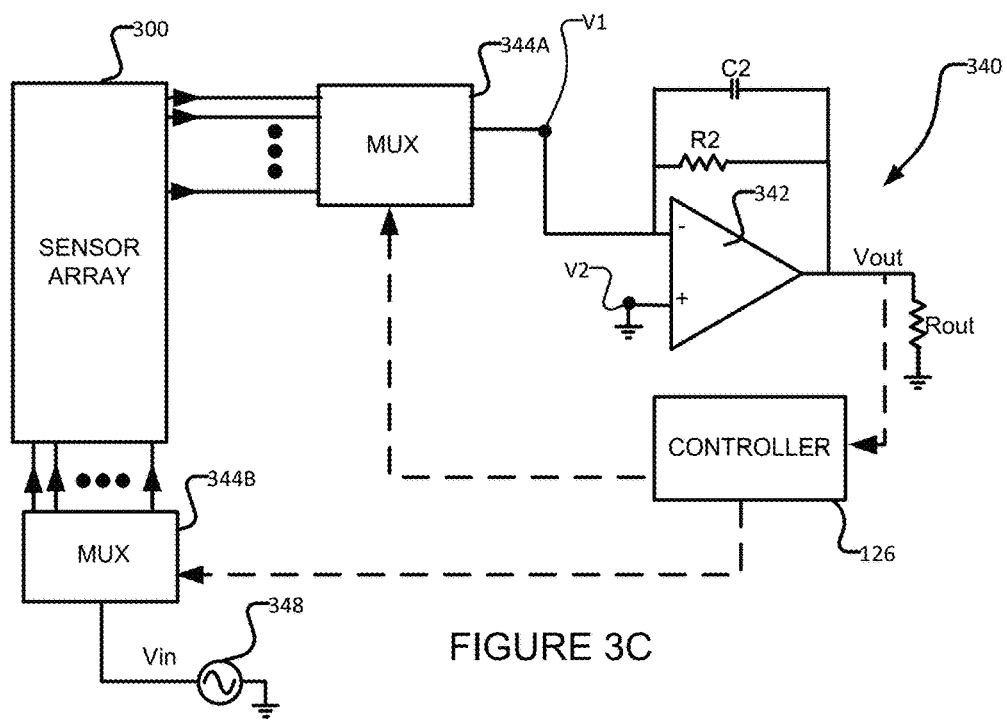
FIG. 3C is a schematic electrical circuit which may be used to detect the voltage difference between a pair of electrodes and to thereby probe the FIG. 3A or FIG. 3B sensor arrays according to another embodiment of the invention.

FIG. 3C shows an example electrical circuit 340 which may be used to detect a voltage $V_{out}$ that is representative of a capacitance between an overlapping pair of electrodes $(x_i, y_j)$ in array 300 (FIG. 3A) or array 300' (FIG. 3B). Like circuit 140 described above, circuit 340 is a type of charge amplification circuit comprising an operational amplifier 342. Circuit 340 is driven by AC power supply 348 which drive a signal onto the electrodes of sensor array 300, 300'. Resistor R2 may be selected to be suitably large, such that the current through feedback loop (comprising capacitor C2 and resistor R2) is principally attributed to a ratio between C2 and the impedance between the positive and negative input leads to amplifier 342. Consequently, the voltage output signal $V_{out}$ is proportional to this current multiplied by output resistor $R_{out}$. The output voltage $V_{out}$ from circuit 340 may be provided to controller 126. It will be appreciated by those skilled in the art that circuit 340 may comprise a variety of signal conditioning elements and/or circuitry (not shown) between output voltage $V_{out}$ and controller 126. By way of non-limiting example, such signal conditioning circuitry may comprise buffers, amplifiers, filtering elements, inverters, analog to digital converters and/or the like. Controller 126 may incorporate or otherwise have access to memory in which the output values of $V_{out}$ may be stored. For the current amplifier circuit 340 of FIG. 3C, it may be shown that the Laplace domain transfer function may be given by:

$$H(s) = \frac{V_{out}(s)}{V_{in}(s)} = \frac{sR_2 C_{in}}{1 + sR_2 C_2} \quad (13)$$

where $C_{in}$ is the capacitance between a pair of electrodes in sensor array 300 which may be connected to AC signal source 348 by MUX 344B and $V_{in}$ is the voltage from AC signal source 348. Knowing this transfer function and the characteristics of the signal $V_{in}$ provided by AC signal source 348, it will be appreciated that it is possible to determine $C_{in}$ (i.e. the capacitance between a pair of electrodes in sensor array 300, 300') by measuring $V_{out}$.

In some embodiments, AC signal source 348 and node V1 may be connected to any pair of electrodes 304 in sensor array 300, 300'. In some embodiments one of AC signal source 348 and node V1 shown in the FIG. 3C circuit 340 may be connected to an x-electrode $x_i$ and the other one of AC signal source 348 and node V1 may be connected to a y-electrode $y_j$. Such connections may be effected by one or more suitable time division multiplexing (TDM) switching multiplexers (MUX) 344A, 344B which may be controlled by a suitable controller 126. In the illustrated embodiment, MUX 344A makes connections between sensor array 300, 300' (e.g. any electrode 304 of sensor array 300, 300') and node V1 and MUX 344B makes connections between sensor array 300, 300' (e.g. any electrode 304 of sensor array 300, 300') and AC signal source 348. The operation of MUXs 344A, 344B will be understood to those skilled in the art. Electrical circuit 340 is merely one example of a charge amplification circuit suitable for determining a current flow between a pair of electrodes 304 in sensor array 300, 300' (and an output voltage $V_{out}$ corresponding to this current flow). In some embodiments, other charge amplifying circuits may be used to detect current flow between a pair of electrodes 304 in sensor array 300, 300' (and an output voltage $V_{out}$ corresponding to this current flow).

Figure 3D:
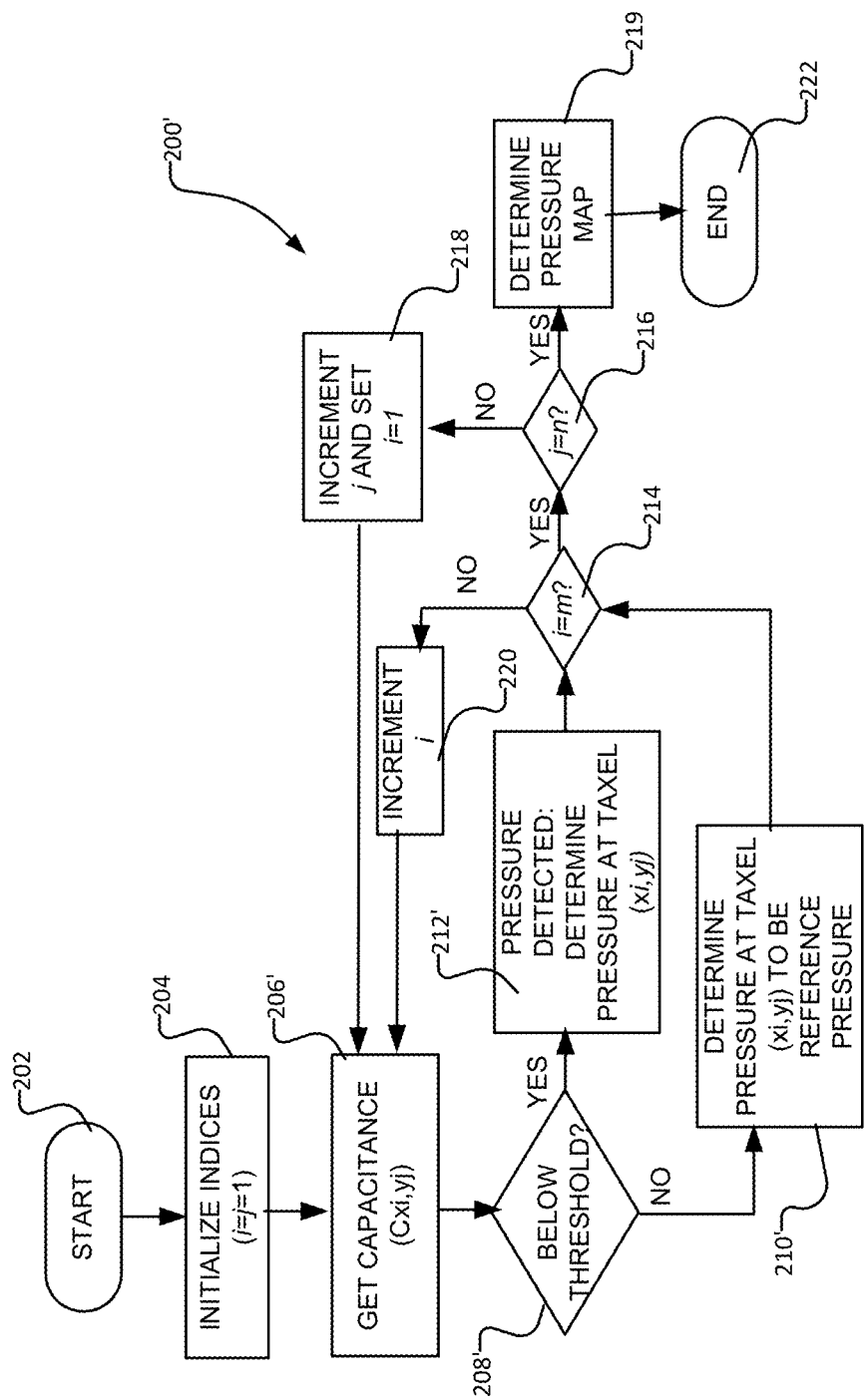
FIG. 3D is a block diagram of a method for creating a pressure map over a sensing surface according to another embodiment of the invention.

FIG. 3D is a schematic illustration of a method 200' for reading out the electrical characteristics from pairs of individual electrodes 304 in sensor array 300 of FIG. 3A (and/or sensor array 300' of FIG. 3B) to obtain a pressure map over sensing surface 110 according to a particular embodiment. Method 200' may be implemented (or at least controlled) by controller 126 (see FIG. 3C). Method 200' is similar in many respects to method 200 (FIG. 2A) described above and similar reference numerals are used to describe similar operational blocks). Method 200' differs from method 200 primarily in that method 200' involves determining capacitances in block 206' (rather than voltages in block 206) between pairs of electrodes 304 that overlap one another in the z-direction. This detection of capacitances performed in block 206' of method 200' may be determined in accordance with the equation (13) of charge amplifying circuit 340 or the transfer function of any other suitable sensing circuit which may be used in addition to or in the alternative to circuit 340. More particularly, in block 206' of the FIG. 3D embodiment, a capacitance and corresponding pressure are obtained for each overlap region $(x_i, y_j)$ corresponding to the overlap region between an x-electrode $x_i$ and a y-electrode $y_j$.

Method 200' of FIG. 3D also differs from method 200 in the block 208' thresholding process. Although the purpose of this thresholding step is similar in both method 200 and method 200', in method 200' this thresholding process involves comparing the block 206' capacitance to a suitable capacitance threshold. Further, the capacitance actually decreases with increased pressure. Consequently, the block 206' inquiry involves determining whether the block 206' capacitance is less than a suitable threshold. If the block 206' capacitance is above this threshold (block 208' NO output), then method 200' proceeds to block 210', where the pressure is determined to be a reference pressure (e.g. atmospheric). If the block 206' capacitance is below this threshold (block 208' YES output), then method 200' proceeds to block 212'. Block 212' of method 200' also differs from block 212 of method 200 in the sense that block 212' involves using the block 206' capacitance (rather than the block 206 voltage) between x-electrode $x_i$ and y-electrode $y_j$ to determine the pressure at overlap region $(x_i, y_j)$ and there is no additive or integrative use of previous iterations. It will be appreciated from the discussion above that when a pressure is applied to surface 110 in a vicinity of overlap region $(x_i,y_j)$, the deformations of the capacitive sensor element changes its capacitance and that this change in capacitance is correlated in an at least approximately predictable way with the change in pressure. In some embodiments, bock 212' may use the equation (12) relationship to determine the pressure from the block 206' capacitance. In some embodiments, block 212' may involve using a different relationship (e.g. an experimentally or empirically determined relationship) between measured capacitance and estimated pressure for a particular overlap region $(x_i,y_j)$. Method 200' also differs from method 200 in that the pressure map is determined directly from the various iterations of block 210' and 212'—i.e. there is no need in method 200' for converting radii of curvature to pressure and so there is no equivalent to block 219 in method 200'.

It will be appreciated from the logic of method 200' that method 200' involves looping through the x-electrodes $x_1$, $x_2, x_3 \ldots x_n$ for a given y-electrode $y_j$ and then incrementing the y-electrode and repeating the x-electrode loop, until all of the overlap regions $(x_i,y_j)$ have been assigned an estimated pressure and a pressure map for surface 110 is obtained. Block 219 or block 222 may involve saving the pressure map to a memory accessible to controller 126 or otherwise further processing the pressure map obtained by method 200'. Like method 200 described above, method 200' may repeated with any suitable frequency for determining pressure maps of interest.

In other respects, method 200' of FIG. 3D may be similar to method 200 of FIG. 2A and method 200' may incorporate any features of and modifications to method 200 which are described herein.

Figure 4A:
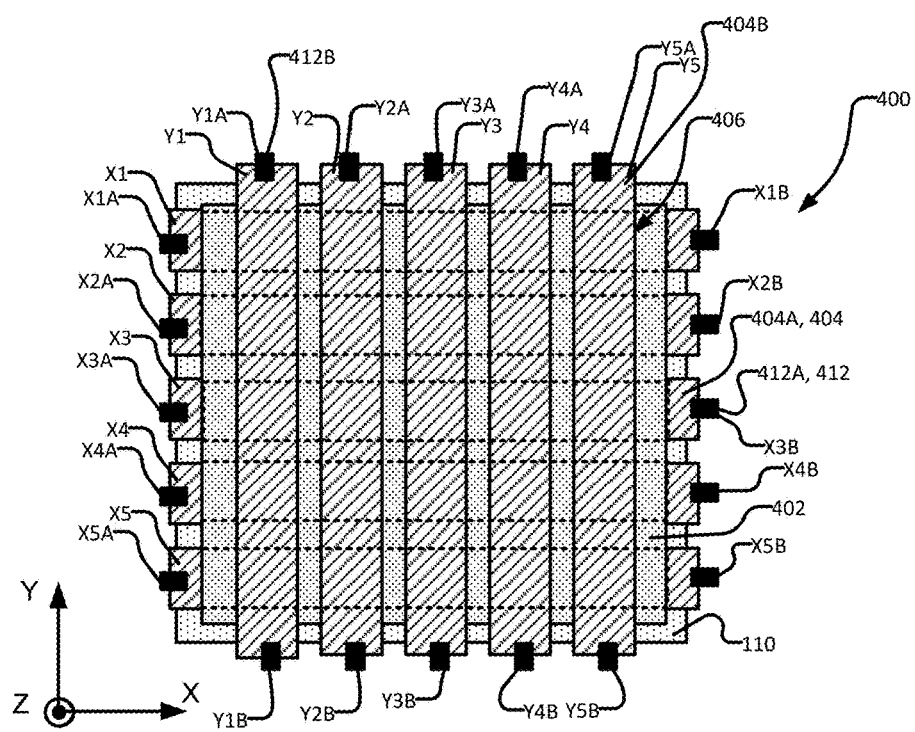
FIG. 4A is a schematic top plan view of a sensor array according to one embodiment of the invention.

FIG. 4A depicts a sensor array 400 for sensing the pressure over a surface 110 according to another particular embodiment. By way of non-limiting example, sensing surface 110 may comprise or be provided on or adjacent to the surface of a bed sheet or mattress on which a person may be located (e.g. the surface of a hospital bed). The FIG. 4A sensor array 400 comprises an array of piezoresistive sensing elements comprising piezoresistive ionically conductive material. In the illustrated FIG. 4A embodiment, sensing surface 110 being mapped is shown as being generally planar for ease of explanation, but this is not necessary and sensing surface 110 may generally have any shape to suit a corresponding application. In the FIG. 4A embodiment, sensor array 400 is distributed over a working region 406 that is adjacent to (e.g. in force transmitting contact with) sensing surface 110. Because sensor array 400 has some depth (shown as being in the z direction in the illustrated view of FIG. 4A), sensor array 400 is not technically distributed over a surface. However, in this description and any accompanying claims and/or aspects, references to sensors arrays and/or elements of sensor arrays being distributed over, on, relative to or otherwise in relation to the surface to be mapped should be understood to refer to a working region adjacent to (e.g. in force transmitting contact with) the surface (e.g. working region 406 adjacent to sensing surface 110), unless the context clearly dictates otherwise.

Sensor array 400 comprises a first plurality of ionically conductive elements 404A and a second plurality of ionically conductive elements 404B (collectively, ionically conductive elements 404) which are distributed over working region 406 and which are connected for use in a piezoresistive sensing mode. Ionically conductive elements 404 may be fabricated from suitable ionically conductive materials, such as, by way of non-limiting example, any suitable materials disclosed herein, in the '265 application or in the '238 application. Ionically conductive elements 404B of the FIG. 4A embodiment have an elongated shape which extends in a y-direction. Because of this elongated shape, ionically conductive elements 404B may be referred to herein as y-elements. Similarly, ionically conductive elements 404A of the FIG. 4A embodiment are elongated in a x-direction and may be referred to herein as x-elements. To help with the explanation, x-elements 404A are also labelled $x1, x2, x3 \ldots x_n$ and y-elements 404B are also labelled and referred to herein as $y1, 2, y3 \ldots y_m$, where n and m are any suitable positive integers, it being appreciated that the number of n of x-elements 404A and the number m of y-elements 404B may vary for particular surfaces 110 and/or particular applications. The ends of ionically conductive x-elements 404A may be provided with electrically conductive electrodes 412A and the ends of ionically conductive y-elements 404B may be provided with electrically conductive electrodes 412B. Electrodes 412A, 412B (collectively, electrodes 412) may be fabricated from suitable metals, alloys of metals and/or the like. Electrodes 412A are located at opposing (in the x-direction) edges of ionically conductive x-elements 404A and may be referred to herein as x-electrodes 412A and electrodes 412B are located at opposing (in the y-direction) edges of ionically conductive y-elements 404B and may be referred to herein as y-electrodes 412B. To help with the explanation, opposed x-electrodes 412A are also labelled $x_{1A}, x_{1B}; x_{2A}, x_{2B}; x_{3A}, x_{3B} \ldots x_{nA}, x_{nB}$ and opposed y-electrodes 412B are also labelled and referred to herein as $y_{1A}, y_{1B}; y_{2A}, y_{2B}; y_{3A}, y_{3B} \ldots y_{mA}, y_{mB}$, where n and m are any suitable positive integers, it being appreciated that the number of n of x-electrodes 412A and the number m of y-electrodes 412B may vary for particular surfaces 110 and/or particular applications.

In the particular case of the FIG. 4A illustration, where sensing surface 110 is shown as being planar, the x and y directions may be considered to have generally constant spatial orientations which are the Cartesian x and y orientations shown in FIG. 4A. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 4A illustration, where sensing surface 110 is shown as being planar, the z direction shown in FIG. 4A may be considered to have generally constant spatial orientation which corresponds to the Cartesian z orientations shown in FIG. 4A. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

Sensor array 400 comprises an insulating layer 402 which is interposed between the array of ionically conductive x-elements 404A and the array of ionically conductive y-elements 404B. Insulating layer 402 may be fabricated from suitable materials, such as, by way of non-limiting example, any suitable dielectric materials described herein, in the '265 application or in the '238 application. A piezoresistive pressure sensing element may be implemented by the ionically conductive elements 404, wherein there is an estimatable relationship between the pressure experienced by the piezoresistive pressure sensing element 404 and the resistance of the piezoresistive pressure sensing element 404. Without wishing to be bound by theory, a derivation is presented to demonstrate that, under certain assumptions, there is a relationship between the resistance of ionically conductive elements and the pressure exerted in a region of such ionically conductive elements. If we assume an ionically conductive x-element 404A, a change in resistance ΔR relative to a nominal resistance $R_0$ may be assumed to be given by:

$$\frac{\Delta R}{R_0} = \frac{\Delta x}{x_o} - \frac{\Delta A}{A_0} = \epsilon_x - (\epsilon_y + \epsilon_z + \epsilon_y \cdot \epsilon_z) \quad (14)$$

where A is the area (having dimensions y,z) that is cross-sectional to the x-extension of x-element 404A, Δx is a change in the x dimension, $x_0$ is a nominal x dimension, ΔA is a change in the x dimension, $A_o$ is a nominal cross-sectional area and $$\epsilon_\alpha = \frac{\Delta \alpha}{\alpha_o}$$

is a strain for any dimension α. For a pressure $P_z$ in the z-direction:

$$Y = \frac{P_z}{\epsilon_z} \quad (15)$$

If we assume that the Poisson's ration u=0.5, then $\epsilon_x = \epsilon_y = 0.5 \epsilon_z$. Using this assumption, we may combine equations (14) and (15) to obtain a relationship between the equation (14) change in resistance $\Delta R/R_0$ and the equation (15) pressure $P_z$. This derivation demonstrates that under these example conditions and assumptions, there is a relationship between the resistance of ionically conductive elements 404 and the pressure exerted in a region of such ionically conductive elements 404. In general, however, this relationship between the resistance of ionically conductive elements 404 and the pressure exerted in a region of such ionically conductive elements 404 is not limited to this exemplary derivation and this relationship may be determined (e.g. experimentally) for any particular applications.

Figure 4C:
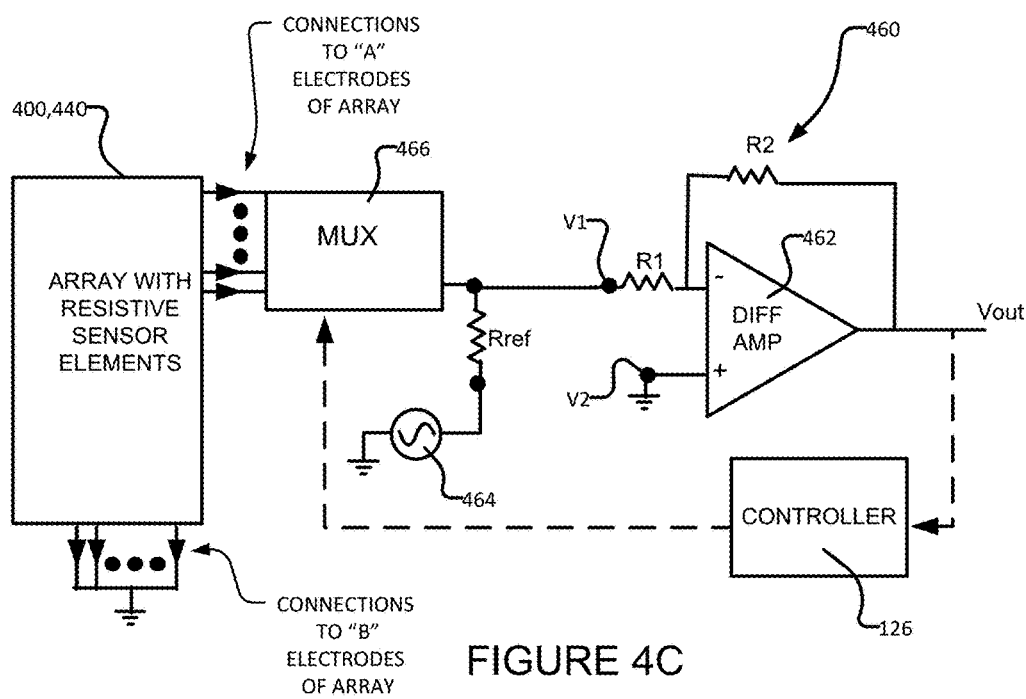
FIG. 4C is a schematic electrical circuit which may be used to detect the voltage difference between a pair of electrodes and to thereby probe the FIG. 4A or 4B sensor arrays according to another embodiment of the invention.
Figure 4B:
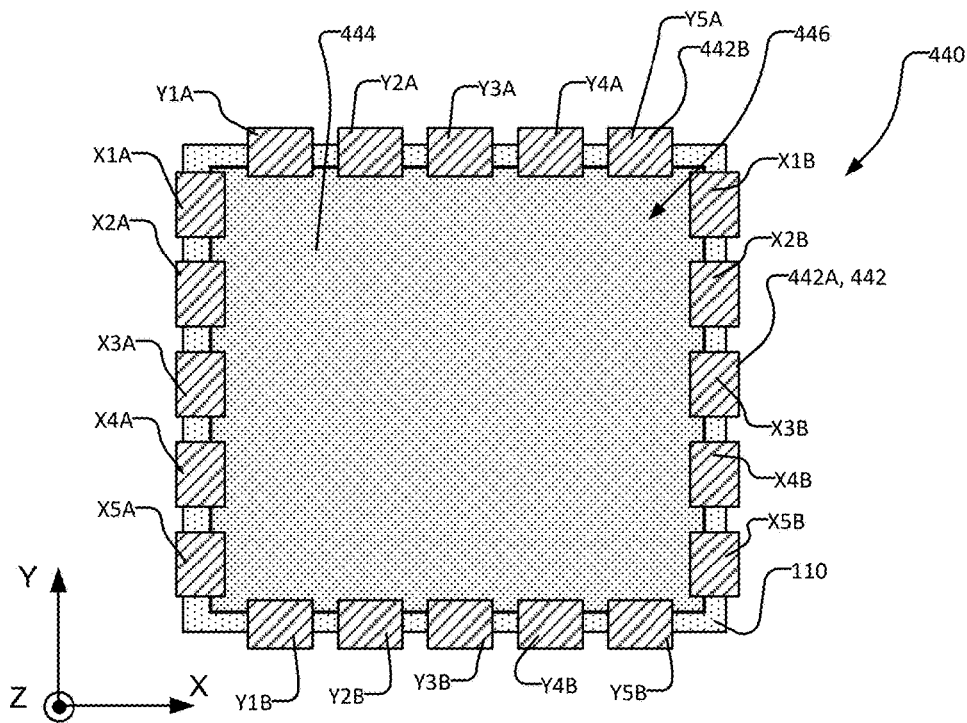
FIG. 4B is a schematic top plan view of a sensor array according to one embodiment of the invention.

FIG. 4B depicts a sensor array 440 for sensing the pressure over a sensing surface 110 according to another particular embodiment. By way of non-limiting example, sensing surface 110 may comprise or be provided on or adjacent to the surface of a bed sheet or mattress on which a person may be located (e.g. the surface of a hospital bed). Like FIG. 4A sensor array 400 described above, the FIG. 4B sensor array 440 operates using a piezoresistive principle using piezoresistive ionically conductive material. In the illustrated FIG. 4B embodiment, sensing surface 110 being mapped is shown as being generally planar for ease of explanation, but this is not necessary and sensing surface 110 may generally have any shape to suit a corresponding application. In the FIG. 4B embodiment, sensor array 440 is distributed over a working region 446 that is adjacent to (e.g. in force transmitting contact with) sensing surface 110. Because sensor array 440 has some depth (shown as being in the z direction in the illustrated view of FIG. 4B), sensor array 440 is not technically distributed over a surface. However, in this description and any accompanying claims and/or aspects, references to sensors arrays and/or elements of sensor arrays being distributed over, on, relative to or otherwise in relation to the surface to be mapped should be understood to refer to a working region adjacent to (e.g. in force transmitting contact with) the surface (e.g. working region 446 adjacent to sensing surface 110), unless the context clearly dictates otherwise.

Sensor array 440 comprises a piezoresistive ionically conductive layer 444 which spans at least a majority of working region 446. Piezoresistive ionically conductive layer 444 may be fabricated from suitable ionically conductive materials, such as, by way of non-limiting example, any suitable materials disclosed herein, in the '265 application or in the '238 application. Sensor array 440 comprises a number of electrodes 442A, 442B (collectively electrodes 442) distributed about the edges of piezoresistive ionically conductive layer 444. Electrodes 442 are electrically conducting and may be fabricated from suitable metals, metal alloys or the like. Electrodes 442A are located at opposing (in the x-direction) edges of ionically piezoresistive conductive layer 444 and may be referred to herein as x-electrodes 442A and electrodes 442B are located at opposing (in the y-direction) edges of piezoresistive ionically conductive layer 444 and may be referred to herein as y-electrodes 442B. To help with the explanation, opposed x-electrodes 442A are also labelled $x_{1A}$, $x_{1B}$; $x_{2A}$, $x_{2B}$; $x_{3A}$, $x_{3B}$ ... $x_{nA}$, $x_{nB}$ and opposed y-electrodes 442B are also labelled and referred to herein as $y_{1A}$, $y_{1B}$; $y_{2A}$, $y_{2B}$; $y_{3A}$, $y_{3B}$ ... $y_{mA}$, $y_{mB}$, where n and m are any suitable positive integers, it being appreciated that the number of n of x-electrodes 442A and the number m of y-electrodes 442B may vary for particular sensing surfaces 110 and/or particular applications.

In the particular case of the FIG. 4B illustration, where sensing surface 110 is shown as being planar, the x and y directions may be considered to have generally constant spatial orientations which are the Cartesian x and y orientations shown in FIG. 4B. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 4B illustration, where sensing surface 110 is shown as being planar, the z direction shown in FIG. 4B may be considered to have generally constant spatial orientation which corresponds to the Cartesian z orientations shown in FIG. 4B. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

A piezoresistive pressure sensing array may be implemented by piezoresistive ionically conductive layer 444. For example, a resistance may be measured between opposing x-electrodes 442A of sensor array 440 (e.g. between electrodes $x_{1A}$, $x_{1B}$; or $x_{3A}$, $x_{3B}$) and may be responsive to pressure exerted on sensing surface 110 and corresponding deformation of piezoresistive ionically conductive layer 444 in a region between the opposing x-electrodes 442A that is analogous to the resistive change of an ionically conductive x-element 404A of the FIG. 4A sensor array 400. Similarly, a resistance may be measured between opposing y-electrodes 442B of sensor array 440 (e.g. between electrodes $y_{1A}, y_{1B}$; or $y_{3A}, y_{3B}$) and may be responsive to pressure exerted on sensing surface 110 and corresponding deformation of piezoresistive ionically conductive layer 444 in a region between the opposing y-electrodes 442B that is analogous to the resistive change of an ionically conductive y-element 404B of the FIG. 4A sensor array 400. Measuring resistance between pairs of electrodes 442 in the FIG. 4B embodiment is not limited to opposing x-electrodes 442A or opposing y-electrodes 442B. In some embodiments, a resistance may be measured between any pair of electrodes 442 in sensor array 440 (e.g. a pair of electrodes 442 comprising any pair of x-electrodes 442A and y-electrodes 442B) to detect pressure exerted on sensing surface 110 and corresponding deformation of piezoresistive ionically conductive layer 444 in a region between the pair of electrodes 442.

FIG. 4C shows an example electrical circuit 460 which may be used to detect the resistance between a pair of opposed x-electrodes $x_{1A}, x_{1B}$; $x_{2A}, x_{2B}$; $x_{3A}, x_{3B}$ ... $x_{nA}, x_{nB}$ and/or opposed y-electrodes $y_{1A}, y_{1B}$; $y_{2A}, y_{2B}$; $y_{3A}, y_{3B}$ ... $y_{mA}, y_{mB}$ from either of sensor arrays 400, 440 of FIGS. 4A and 4B (e.g. for any pair of electrodes 412 of sensor array 400 of FIG. 4A or any pair of electrodes 442 of sensor array 440 of FIG. 4B) according to a particular embodiment. Circuit 460 is a voltage amplification circuit comprising an operational amplifier 462 and a voltage source 464 (which is shown as being an AC source 464, but which is not limited to being an AC source). The voltage $V_{out}$ is proportional the ratio of resistors R2 and R1 multiplied by the voltage difference (V2−V1) between the input connections to the sensor array (e.g. sensor array 100)—i.e.

$$(e.g. \text{ sensor array } 100) - i.e. \ V_{out} \propto \frac{R_2}{R_1}(V_2 - V_1).$$

Where V2 is tied to ground, as is the case with the illustrated embodiment, $V_{out}$ $$\propto -\frac{R_2}{R_1}V_1.$$

The output voltage $V_{out}$ from circuit 460 may be provided to controller 126. It will be appreciated by those skilled in the art that circuit 460 may comprise a variety of signal conditioning elements and/or circuitry (not shown) between output voltage $V_{out}$ and controller 126. By way of non-limiting example, such signal conditioning circuitry may comprise buffers, amplifiers, filtering elements, inverters, analog to digital converters and/or the like. Controller 126 may incorporate or otherwise have access to memory in which the output values of $V_{out}$ may be stored. As shown in FIG. 4C, the "B" electrodes of the sensor array (e.g. x-electrodes $x_{1B}, x_{2B}, x_{3B} \ldots x_{nB}$ and y-electrodes $y_{1B}, y_{2B}, y_{3B} \ldots, y_{mB}$ of array 400 or array 440) may be tied to ground and the "A" electrodes of the sensor array (e.g. x-electrodes $x_{1A}, x_{2A}, x_{3A} \ldots x_{nA}$ and y-electrodes $y_{1A}, y_{2A}, y_{3A} \ldots, y_{mA}$ of array 400 or array 440) may be switched by MUX 466 (under the control of controller 126) to connect to node V1. In this manner, the voltage from source 464 at node V1 is a voltage divider between $R_{ref}$ and $R_{sens}$, where $R_{sens}$ is the resistance between a particular pair of opposing electrodes (e.g. opposed x-electrodes $x_{1A}, x_{1B}$; $x_{2A}, x_{2B}$; $x_{3A}, x_{3B} \ldots x_{nA}, x_{nB}$ or opposed y-electrodes $y_{1A}, y_{1B}$; $y_{2A}, y_{2B}$; $y_{3A}, y_{3B} \ldots y_{mA}, y_{mB}$). Accordingly, since the relationship between $R_{sens}$ and V1 is known and the relationship between V1 and $V_{out}$ is known, $R_{sens}$ can be determined by controller 126 based on the voltage $V_{out}$. It will be appreciated that electrical circuit 460 is merely one example of a voltage amplification circuit suitable for determining a resistance between a pair of opposed x-electrodes $x_{1A}, x_{1B}$; $x_{2A}, x_{2B}$; $x_{3A}, x_{3B} \ldots x_{nA}, x_{nB}$ and/or opposed y-electrodes $y_{1A}, y_{1B}$; $y_{2A}, y_{2B}$; $y_{3A}, y_{3B} \ldots y_{mA}, y_{mB}$ from either of sensor arrays 400, 440. In some embodiments, other voltage amplifying circuits may be used to detect these parameters. As discussed above, the pairs of electrodes 442 for which the resistance is measured in sensor array 440 (FIG. 4B) is not limited to opposing pairs of electrodes 442.

Figure 4D:
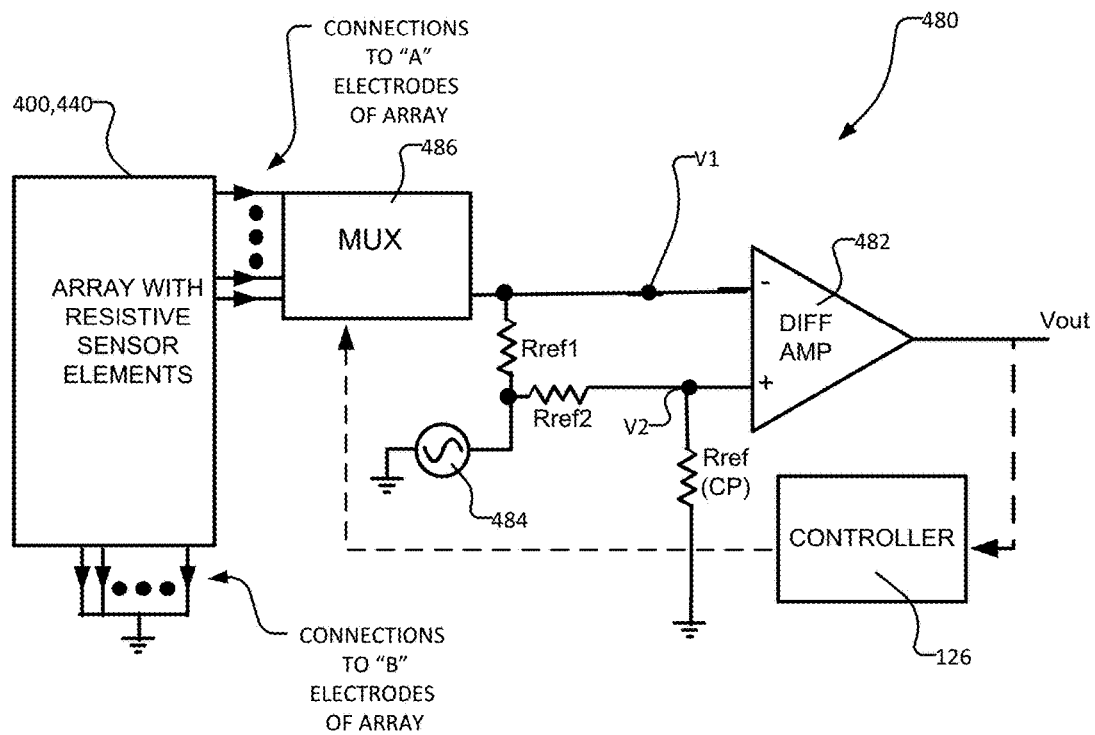
FIG. 4D is a schematic electrical circuit which may be used to detect the voltage difference between a pair of electrodes and to thereby probe the FIG. 4A or 4B sensor arrays according to another embodiment of the invention.

FIG. 4D shows an example another electrical circuit 480 which may be used to detect the resistance between a pair of opposed x-electrodes $x_{1A}, x_{1B}$; $x_{2A}, x_{2B}$; $x_{3A}, x_{3B} \ldots x_{nA}$, $x_{nB}$ B and/or opposed y-electrodes $y_{1A}, y_{1B}$; $y_{2A}, y_{2B}$; $y_{3A}, y_{3B} \ldots y_{mA}, y_{mB}$ from either of sensor arrays 400, 440 of FIGS. 4A and 4B (e.g. for any pair of electrodes 412 of sensor array 400 of FIG. 4A or any pair of electrodes 442 of sensor array 440 of FIG. 4B) according to a particular embodiment. Circuit 480 is a wheatstone bridge amplification circuit comprising a differential amplifier (also known as an instrumentation amplifier) 482 and a voltage source 484 (which is shown as being an AC source 484, but which is not limited to being an AC source). The voltage $V_{out}$ is proportional the difference between the voltages at nodes V1 and V2 (e.g. $V_{out} \propto (V_2 - V_1)$). The output voltage $V_{out}$ from circuit 480 may be provided to controller 126. It will be appreciated by those skilled in the art that circuit 480 may comprise a variety of signal conditioning elements and/or circuitry (not shown) between output voltage $V_{out}$ and controller 126. By way of non-limiting example, such signal conditioning circuitry may comprise buffers, amplifiers, filtering elements, inverters, analog to digital converters and/or the like. Controller 126 may incorporate or otherwise have access to memory in which the output values of $V_{out}$ may be stored. As shown in FIG. 4D, the "B" electrodes of the sensor array (e.g. x-electrodes $x_{1B}, x_{2B}, x_{3B} \ldots x_{nB}$ and y-electrodes $y_{1B}, y_{2B}, y_{3B} \ldots, y_{mB}$ of array 400 or array 440) may be tied to ground and the "A" electrodes of the sensor array (e.g. x-electrodes $x_{1A}, x_{2A}, x_{3A} \ldots x_{nA}$ and y-electrodes $y_{1A}, y_{2A}, y_{2A} \ldots, y_{mA}$ of array 400 or array 440) may be switched by MUX 486 (under the control of controller 126) to connect to node V1. In this manner, the voltage from voltage source 484 at node V1 is a voltage divider between $R_{ref1}$ and $R_{sens}$, where $R_{sens}$ is the resistance between a particular pair of opposing electrodes (e.g. opposed x-electrodes $x_{1A}, x_{1B}$; $x_{2A}, x_{2B}$; $x_{3A}, x_{3B} \ldots x_{nA}, x_{nB}$ or opposed y-electrodes $y_{1A}, y_{1B}$; $y_{2A}, y_{2B}$; $y_{3A}, y_{3B} \ldots y_{mA}, y_{mB}$). Similarly, the voltage from voltage source 484 at node V2 is a voltage divider between $R_{ref2}$ and $R_{ref(CP)}$, where $R_{ref(CP)}$ is an ionically conductive polymer resistance reference which may be continually subjected only to atmospheric pressure. $R_{ref(CP)}$ may be implemented as part of sensor array 400 or 440, but may be located in a location where it will not experience pressure (other than atmospheric) in use. Other than being subjected only to atmospheric pressure, $R_{ref(CP)}$ may have characteristics similar to the resistive elements between any opposed pair of electrodes in sensor arrays 440, 440 (e.g. opposed x-electrodes $x_{1A}, x_{1B}$; $x_{2A}, x_{2B}$; $x_{3A}, x_{3B} \ldots x_{nA}, x_{nB}$ or opposed y-electrodes $y_{1A}, y_{1B}$; $y_{2A}, y_{2B}$; $y_{3A}, y_{3B} \ldots y_{mA}, y_{mB}$). Since the relationship between $R_{sens}$ and V1 is known and the relationship between $R_{ref(CP)}$ and V2 is known, any difference between $R_{sens}$ and $R_{ref(CP)}$ resulting from pressure applied to the resistive element between the electrodes corresponding to $R_{sens}$, will result in a corresponding difference between V1 and V2 and a corresponding difference at $V_{out}$. Accordingly, $R_{sens}$ (or the difference between $R_{ref(CP)}$ and $R_{sens}$) can be determined from $V_{out}$. It will be appreciated that electrical circuit 480 is merely one example of a bridge circuit suitable for determining a resistance between a pair of opposed x-electrodes $x_{1A}$, $x_{1B}$; $x_{2A}$, $x_{2B}$; $x_{3A}$, $x_{3B}$ ... $x_{nA}$, $x_{nB}$ and/or opposed y-electrodes $y_{1A}$, $y_{1B}$; $y_{2A}$, $y_{2B}$; $y_{3A}$, $y_{3B}$ ... $y_{mA}$, $y_{mB}$ from either of sensor arrays 400, 440. In some embodiments, other bridge circuits may be used to detect these parameters. As discussed above, the pairs of electrodes 442 for which the resistance is measured in sensor array 440 (FIG. 4B) is not limited to opposing pairs of electrodes 442.

Figure 4E:
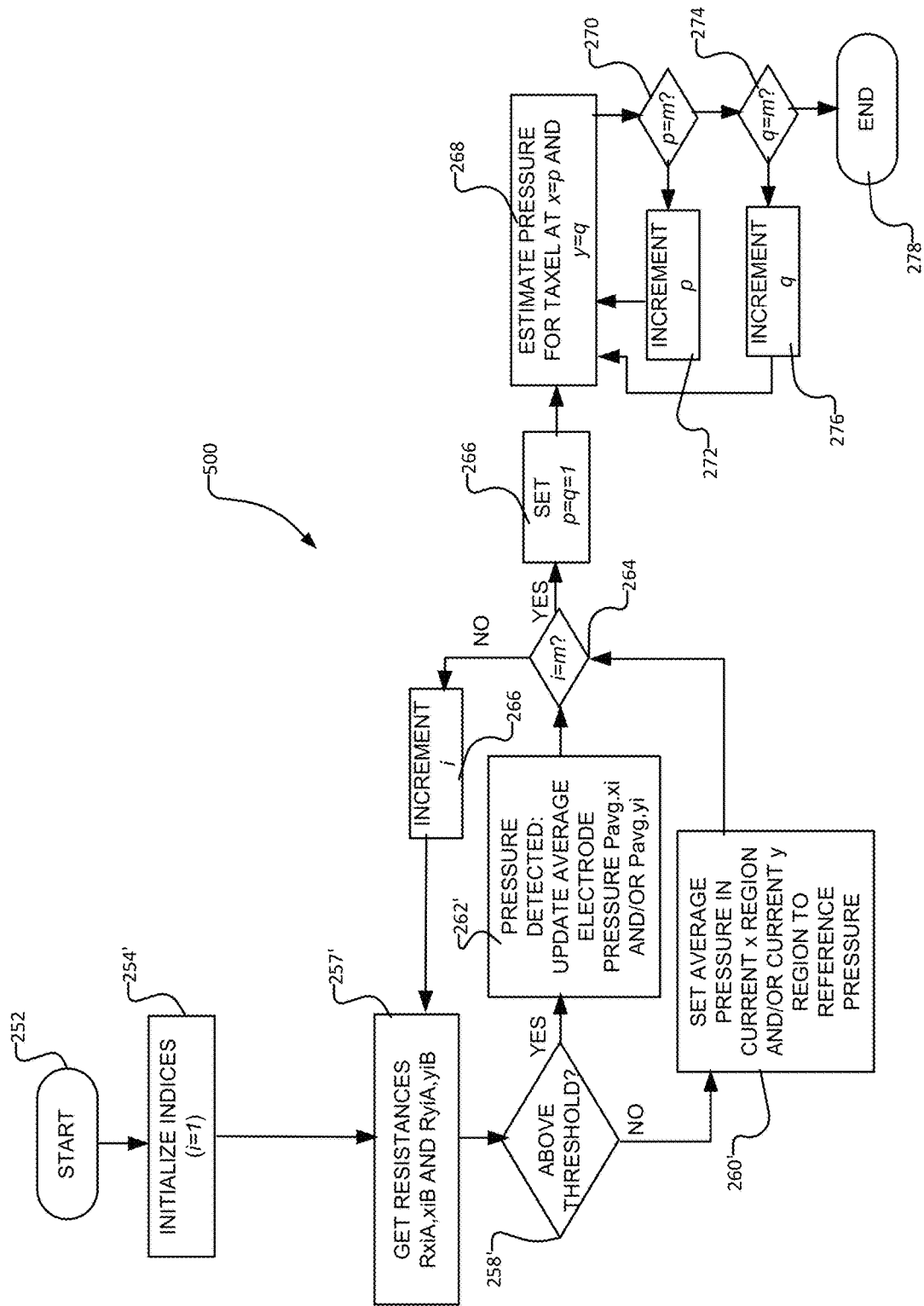
FIG. 4E is a block diagram of a method for creating a pressure map over a sensing surface according to another embodiment of the invention.

FIG. 4E is a schematic illustration of a method 500 for using the resistive elements of either sensor array 400 or sensor array 440 and reading out the resistances of individual resistive elements using the voltage amplification circuit 460 of FIG. 4C to obtain a pressure map over sensing surface 110 according to another particular embodiment. Method 500 may be implemented (or at least controlled) by controller 126 (see FIG. 4C). As will be described in more detail below, method 500 involves: detecting resistances between pairs of electrodes 412, 442 in sensor arrays 400, 440 (e.g. opposed x-electrodes $x_{1A}$, $x_{1B}$; $x_{2A}$, $x_{2B}$; $x_{3A}$, $x_{3B}$ ... $x_{nA}$, $x_{nB}$ or opposed y-electrodes $y_{1A}$, $y_{1B}$; $y_{2A}$, $y_{2B}$; $y_{3A}$, $y_{3B}$ ... $y_{mA}$, $y_{mB}$) and then using those resistances to determine a pressure estimate for corresponding regions or taxels $(x_i, y_j)$. Method 500 is similar in many respects to method 250 (FIG. 2B) described above and similar reference numerals are used to describe similar functional blocks or steps.

After commencing in block 252, method 500 of FIG. 4E proceeds to block 254' which differs from block 254 in that block 254' involves initializing the loop index i to i=1. In the FIG. 4E embodiment, it is assumed (for ease of explanation and without loss of generality) that the number opposed x-electrodes and opposed y-electrodes is the same and is equal to m (e.g. opposed x-electrodes $x_{1A}$, $x_{1B}$; $x_{2A}$, $x_{2B}$; $x_{3A}$, $x_{3B}$ ... $x_{mA}$, $x_{mB}$ and opposed y-electrodes $y_{1A}$, $y_{1B}$; $y_{2A}$, $y_{2B}$; $y_{3A}$, $y_{3B}$ ... $y_{mA}$, $y_{mB}$). In the first portion of method 500, the index i may be used to index both the opposed pairs of x and y electrodes. Method 500 then proceeds to block 257' which differs from block 257 in that block 257' involves determining the resistances ($R_{xiA,xiB}$ from the pair of opposed x-electrodes and $R_{yiA,yiB}$ from the i$^{th}$ pair of opposed y-electrodes) rather than voltage differences. Block 257' may be effected (using voltage amplification circuit 460 of FIG. 4C or some other suitable voltage amplification circuit) by causing MUX 466 to effect connections to particular "A" x-electrodes and "A" y-electrodes (e.g. x-electrodes $x_{1A}$, $x_{2A}$, $x_{3A}$ ... $x_{nA}$ and y-electrodes $y_{1A}$, $y_{2A}$, $y_{3A}$ ..., $y_{mA}$ of array 400 or array 440).

Method 500 then proceeds to block 258' which involves a thresholding inquiry similar to block 258 described above, except that the block 258' thresholding inquiry may be conducted in the resistance domain. The purpose and effect of the block 258' thresholding process may be similar to the purpose and effect of the above-discussed block 258 thresholding process. If either of the x or y resistances determined in block 257' is less than some suitable cut-off resistance threshold, which may be configurable and/or calibratable for particular embodiments and/or applications (block 258' NO output), then method 500 proceeds to block 260'. Block 260' is analogous to block 260 described above and involves the assumption that there is no average external pressure above a pressure reference (e.g. above atmospheric pressure) in the region between the current opposed x-electrodes $x_{iA}$, $x_{iB}$ and/or in the region between the current opposed y-electrodes $y_{iA}$, $y_{iB}$. If either of the x or y resistances determined in block 257' is greater than the resistance threshold (block 258'YES output), then method 500 proceeds to block 262' which involves determining the average pressure in the region between the current opposed x-electrodes $x_{iA}$, $x_{iB}$ and/or in the region between the current opposed y-electrodes $y_{iA}$, $y_{iB}$ (which may be referred to herein as $P_{avg,xi}$ and/or $P_{avg,yi}$). The relationship between the resistance in the region between the current opposed x-electrodes $x_{iA}$, $x_{iB}$ and/or in the region between the current opposed y-electrodes $y_{iA}$, $y_{iB}$ and the corresponding pressures ($P_{avg,xi}$ and $P_{avg,yi}$) may be determined and or calibrated experimentally for given geometries and/or conditions (e.g. temperature). The procedures of blocks 258', 260' and 262' are shown in FIG. 4E as occurring for both the current opposed x-electrodes $x_{iA}$, $x_{iB}$ and the current opposed y-electrodes $y_{iA}$, $y_{iB}$ at the same time. However, in practice, these blocks may be performed separately for the current opposed x-electrodes $x_{iA}$, $x_{iB}$ and the current opposed y-electrodes $y_{iA}$, $y_{iB}$. For example, the current opposed x-electrodes $x_{iA}$, $x_{iB}$ may end up in block 260', whereas the opposed y-electrodes $y_{iA}$, $y_{iB}$ may end up in block 262'.

Whether via block 260' or block 262', method 500 proceeds to block 264. From block 264 through the remainder of method 500, method 500 is analogous to method 250 described above, with the exception that the overlapping (in the z-direction) electrodes 104 and interposed piezoionic ionically conductive material 102 of sensor array 100 are replaced with opposed pairs of x-electrodes $x_{iA}$, $x_{iB}$ and/or opposed pairs of y-electrodes $y_{iA}$, $y_{iB}$ and corresponding regions of piezoresistive ionically conductive polymer 404, 444 arranged between the opposed electrodes in sensors 400, 440.

Figure 4F:
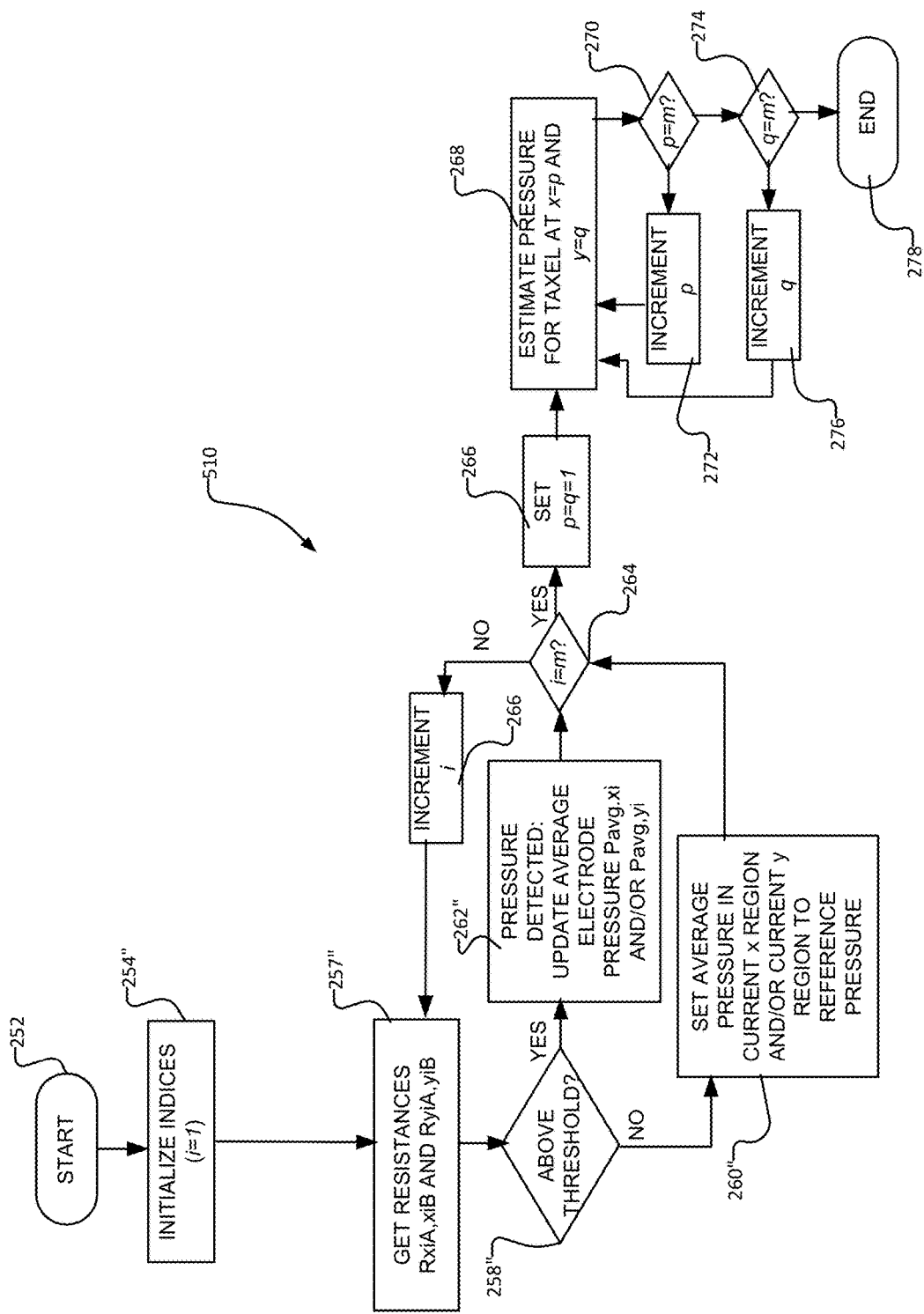
FIG. 4F is a block diagram of a method for creating a pressure map according to another embodiment of the invention.

FIG. 4F is a schematic illustration of a method 510 for using the resistive elements of either sensor array 400 or sensor array 440 and reading out the resistances of individual resistive elements using the bridge circuit 480 of FIG. 4D to obtain a pressure map over sensing surface 110 according to another particular embodiment. Method 510 may be implemented (or at least controlled) by controller 126 (see FIG. 4D). As will be described in more detail below, method 510 involves: detecting resistances between pairs of electrodes 412, 442 in sensor arrays 400, 440 (e.g. opposed x-electrodes $x_{1A}$, $x_{1B}$; $x_{2A}$, $x_{2B}$; $x_{3A}$, $x_{3B}$ ... $x_{nA}$, $x_{nB}$ or opposed y-electrodes $y_{1A}$, $y_{1B}$; $y_{2A}$, $y_{2B}$; $y_{3A}$, $y_{3B}$ ... $y_{mA}$, $y_{mB}$) and then using those resistances to determine a pressure estimate for corresponding regions or taxels $(x_i, y_j)$. Method 510 is similar in many respects to method 250 (FIG. 2B) and method 500 described above and similar reference numerals are used to describe similar functional blocks or steps.

After commencing in block 252, method 510 of FIG. 4F proceeds to block 254" which differs from block 254 in that block 254" involves initializing the loop index i to i=1. In the FIG. 4F embodiment, it is assumed (for ease of explanation and without loss of generality) that the number opposed x-electrodes and opposed y-electrodes is the same and is equal to m (e.g. opposed x-electrodes $x_{1A}$, $x_{1B}$; $x_{2A}$, $x_{2B}$; $x_{3A}$, $x_{3B}$ ... $x_{mA}$, $x_{mB}$ and opposed y-electrodes $y_{1A}$, $y_{1B}$; $y_{2A}$, $y_{2B}$; $y_{3A}$, $y_{3B}$ ... $y_{mA}$, $y_{mB}$). In the first portion of method 510, the index i may be used to index both the opposed pairs of x and y electrodes. Method 510 then proceeds to block 257" which differs from block 257 in that block 257" involves determining the resistances ($R_{xiA,xiB}$ from the i$^{th}$ pair of opposed x-electrodes and $R_{yiA,yiB}$ from the i$^{th}$ pair of opposed y-electrodes) rather than voltage differences. These resistances ($R_{xiA,xiB}$ from the i$^{th}$ pair of opposed x-electrodes and $R_{yiA,yiB}$ from the i$^{th}$ pair of opposed y-electrodes) are referred to as $R_{sens}$ in the description of circuit 480 of FIG. 4D above. Block 257" may be effected (using bridge circuit 480 of FIG. 4D or some other suitable voltage amplification circuit) by causing MUX 486 to effect connections to particular "A" x-electrodes and "A" y-electrodes (e.g. x-electrodes $x_{1A}, x_{2A}, x_{3A} \ldots x_{nA}$ and y-electrodes $y_{1A}, y_{2A}, y_{3A}, \ldots, y_{mA}$ of array 400 or array 440).

Method 510 then proceeds to block 258" which involves a thresholding inquiry similar to block 258 described above, except that the block 258" thresholding inquiry may be conducted in the resistance domain. The purpose and effect of the block 258" thresholding process may be similar to the purpose and effect of the above-discussed block 258 thresholding process. If either of the x or y resistances determined in block 257" is less than some suitable cut-off resistance threshold, which may be configurable and/or calibratable for particular embodiments and/or applications (block 258" NO output), then method 500 proceeds to block 260". Block 260" is analogous to block 260 described above and involves the assumption that there is no average external pressure above a pressure reference (e.g. above atmospheric pressure) in the region between the current opposed x-electrodes $x_{iA}, x_{iB}$ and/or in the region between the current opposed y-electrodes $y_{iA}, y_{iB}$. If either of the x or y resistances determined in block 257" is greater than the resistance threshold (block 258" YES output), then method 500 proceeds to block 262" which involves determining the average pressure in the region between the current opposed x-electrodes $x_{iA}, x_{iB}$ and/or in the region between the current opposed y-electrodes $y_{iA}, y_{iB}$ (which may be referred to herein as $P_{avg,xi}$ and/or $P_{avg,yi}$). The relationship between the resistance in the region between the current opposed x-electrodes $x_{iA}, x_{iB}$ and/or in the region between the current opposed y-electrodes $y_{iA}, y_{iB}$ and the corresponding pressures ($P_{avg,xi}$ and $P_{avg,yi}$) may be determined and or calibrated experimentally for given geometries and/or conditions (e.g. temperature). The procedures of blocks 258", 260" and 262" are shown in FIG. 4F as occurring for both the current opposed x-electrodes $x_{iA}, x_{iB}$ and the current opposed y-electrodes $y_{iA}, y_{iB}$ at the same time. However, in practice, these blocks may be performed separately for the current opposed x-electrodes $x_{iA}, x_{iB}$ and the current opposed y-electrodes $y_{iA}, y_{iB}$. For example, the current opposed x-electrodes $x_{iA}, x_{iB}$ may end up in block 260", whereas the opposed y-electrodes $y_{iA}, y_{iB}$ may end up in block 262".

Whether via block 260" or block 262", method 510 proceeds to block 264. From block 264 through the remainder of method 510, method 510 is analogous to method 250 described above, with the exception that: overlapping (in the z-direction) electrodes 104 and interposed piezoionic ionically conductive material 102 are replaced with opposed pairs of x-electrodes $x_{iA}, x_{iB}$ and/or opposed pairs of y-electrodes $y_{iA}, y_{iB}$ and corresponding regions of piezoresistive ionically conductive polymer 404, 444 arranged between the opposed electrodes in sensors 400, 440.

Figures 5A, 5B, 6A:
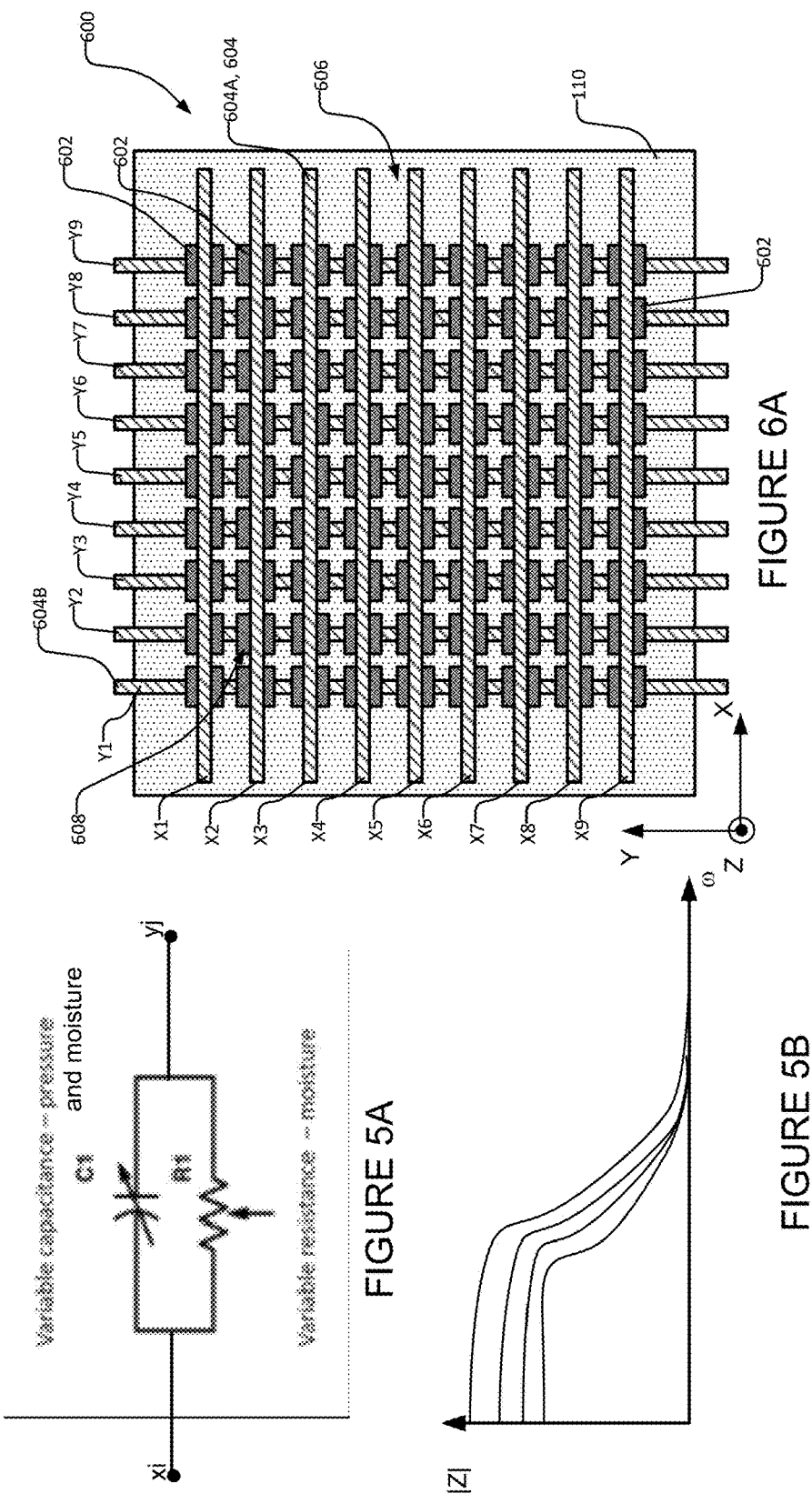
FIG. 5A shows a schematic view of a model circuit illustrating the impedance between a pair of overlapping electrodes in the sensor arrays of FIGS. 3A and 3B according to one embodiment of the invention.
FIG. 5B is a graphical representation of the amplitude component of a variety of typical exemplary frequency response curves for a pair of overlapping electrodes in the sensor arrays of FIGS. 3A and 3B.
FIG. 6A is a schematic top plan view of a sensor array according to one embodiment of the invention.

FIG. 6A depicts a sensor array 600 for sensing the pressure over a sensing surface 110 according to another particular embodiment. By way of non-limiting example, sensing surface 110 may comprise or be provided on or adjacent to the surface of a bed sheet or mattress on which a person may be located (e.g. the surface of a hospital bed). The FIG. 6A sensor array 600 comprises an array of resistive sensing elements comprising ionically conductive material. In the illustrated FIG. 6A embodiment, sensing surface 110 being mapped is shown as being generally planar for ease of explanation, but this is not necessary and sensing surface 110 may generally have any shape to suit a corresponding application. In the FIG. 6A embodiment, sensor array 600 is distributed over a working region 606 that is adjacent to (e.g. in force transmitting contact with) sensing surface 110. Because sensor array 600 has some depth (shown as being in the z direction in the illustrated view of FIG. 6A), sensor array 600 is not technically distributed over a surface. However, in this description and any accompanying claims and/or aspects, references to sensors arrays and/or elements of sensor arrays being distributed over, on, relative to or otherwise in relation to the surface to be mapped should be understood to refer to a working region adjacent to (e.g. in force transmitting contact with) the surface (e.g. working region 606 adjacent to sensing surface 110), unless the context clearly dictates otherwise.

Sensor array 600 comprises a first plurality of electrically conductive electrodes 604A and a second plurality of electrically conductive electrodes 604B (collectively, electrodes 604) which are distributed over working region 606. Electrodes 604 may be fabricated from suitable metals, metal alloys or other electrically conductive materials. Electrodes 604A of the FIG. 6A embodiment have an elongated shape which extends in an x-direction. Because of this elongated shape, electrodes 604A may be referred to herein as x-electrodes. Similarly, electrodes 604B of the FIG. 6A embodiment are elongated in a y-direction and may be referred to herein as y-electrodes. To help with the explanation, x-electrodes 604A are also labelled x1, x2, x3 . . . $x_n$ and y-electrodes 604B are also labelled and referred to herein as y1, 2, y3 . . . $y_m$, where n and m are any suitable positive integers, it being appreciated that the number of n of x-electrodes 604A and the number m of y-electrodes 604B may vary for particular sensing surfaces 110 and/or particular applications. The region in which particular pair of electrodes 604A and 604B overlap one another in the z-direction may be referred to herein as an overlap region 608. For ease of reference, the overlap region 608 between a particular pair of electrodes 604A and 604B may be referred to herein by the indices of the electrodes. For example, the overlap region between the x2 and y3 electrodes may be referred to as overlap region x2, y3.

In the particular case of the FIG. 6A illustration, where sensing surface 110 is shown as being planar, the x and y directions may be considered to have generally constant spatial orientations which are the Cartesian x and y orientations shown in FIG. 6A. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 6A illustration, where sensing surface 110 is shown as being planar, the z direction shown in FIG. 6A may be considered to have generally constant spatial orientation which corresponds to the Cartesian z orientations shown in FIG. 6A. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

Sensor array 600 comprises a plurality of ionically conductive piezoresistive elements 602. Each ionically conductive piezoresistive element 602 is located in a vicinity of, and interposed between, a corresponding overlap region (between an x-electrode 604A and a y-electrode 604B), such that an x-electrode 604A, a y-electrode 604B and ionically conductive piezoresistive element 602 overlap each other in the z-direction in each overlap region.

Sensor array 600 comprises piezoresistive elements 602 between the overlapping x and y electrodes in an overlap region $(x_i, y_j)$. For example, where the pressure on surface 110 in a vicinity of overlap region $(x_i, y_j)$ increases, then the resistance $R_{xi,yj}$ between the corresponding electrodes ought to decrease. Sensor array 600 may be read out using circuits similar to the circuits described above for reading out other sensor arrays comprising piezoresistive ionically conductive materials. For example, a slightly modified version of circuit 460 (FIG. 4C) can be used to probe sensor 600. To enable the FIG. 4C circuit 460 to read out from sensor array 600, the modification would be that MUX 466 would be connected to the x-electrodes 604A (rather than to the "A" electrodes) and the y-electrodes 604B (rather than the "B" electrodes) would be tied to ground. As another example, a slightly modified version of the circuit 480 (FIG. 4D) can be used to probe sensor 600. To enable the FIG. 4D circuit 480 to read out from sensor array 600, the modification would be that MUX 486 would be connected to the x-electrodes 604A (rather than to the "A" electrodes) and the y-electrodes 604B (rather than the "B" electrodes) would be tied to ground.

A method for generating a pressure map using sensor array 600 could be based on a slightly modified version of method 200' (FIG. 3D). In such a modified version of the FIG. 3D method 200', block 206' would be modified to obtain resistance measurements $R_{xi,yj}$ (rather than voltage differences) from the current overlap region $(x_i, y_j)$. Block 208' would also be modified to be an inquiry as to whether the measured resistance $R_{xi,yj}$ for the current overlap region $(x_i, y_j)$ was less than a suitable threshold. Block 212' of method 200' would also be modified for use on sensor array 600 by determining the pressure at the current overlap region $(x_i, y_j)$ based on the measured resistance $R_{xi,yj}$ (rather than based on the measure voltage). In some embodiments, suitable cross-talk mitigation techniques may be used to minimize cross-talk between sensor elements of sensor array 600.

Figure 8A:
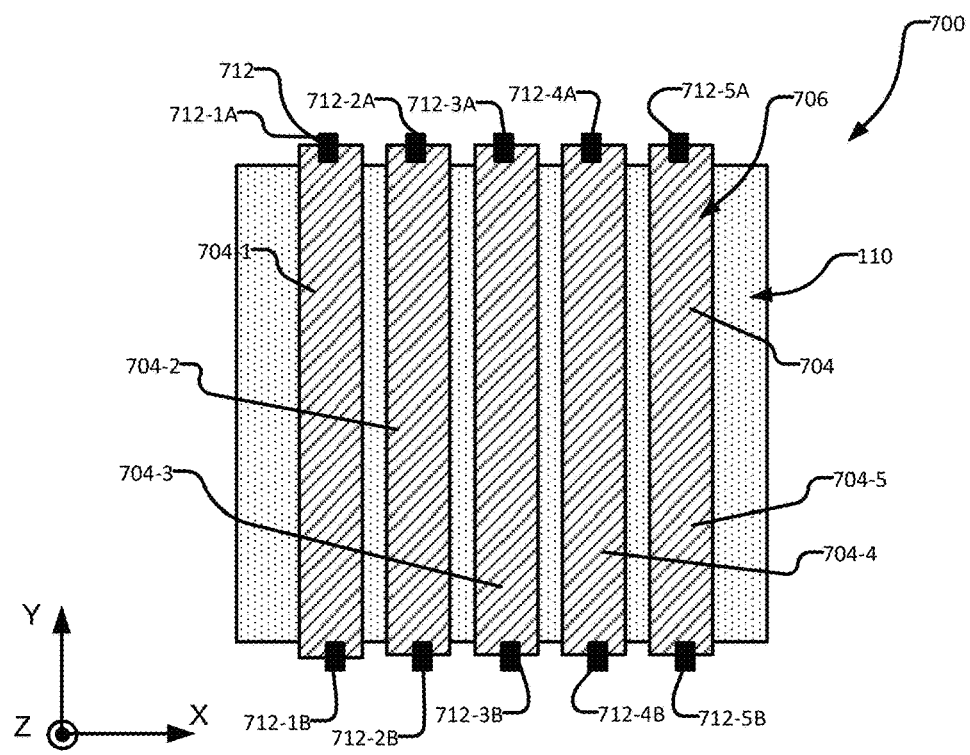
FIG. 8A is a schematic top plan view of a sensor array according to one embodiment of the invention.

FIG. 8A depicts a sensor array 700 for sensing the pressure over a sensing surface 110 according to another particular embodiment. By way of non-limiting example, sensing surface 110 may comprise or be provided on or adjacent to the surface of a bed sheet or mattress on which a person may be located (e.g. the surface of a hospital bed). The FIG. 8A sensor array 700 comprises an array of piezoionic sensing elements comprising ionically conductive material. In the illustrated FIG. 8A embodiment, sensing surface 110 being mapped is shown as being generally planar for ease of explanation, but this is not necessary and sensing surface 110 may generally have any shape to suit a corresponding application. In the FIG. 8A embodiment, sensor array 700 is distributed over a working region 706 that is adjacent to (e.g. in force transmitting contact with) sensing surface 110. Because sensor array 700 has some depth (shown as being in the z direction in the illustrated view of FIG. 8A), sensor array 700 is not technically distributed over a surface. However, in this description and any accompanying claims and/or aspects, references to sensors arrays and/or elements of sensor arrays being distributed over, on, relative to or otherwise in relation to the surface to be mapped should be understood to refer to a working region adjacent to (e.g. in force transmitting contact with) the surface (e.g. working region 706 adjacent to sensing surface 110), unless the context clearly dictates otherwise.

Sensor array 700 comprises a plurality of piezoionic ionically conductive elements 704 which are distributed over working region 706 and which are connected for measuring changes in voltage. Piezoionic ionically conductive elements 704 may be fabricated from suitable ionically conductive materials, such as, by way of non-limiting example, any suitable piezoionic materials disclosed herein, in the '265 application or in the '238 application. Piezoionic ionically conductive elements 704 of the FIG. 8A embodiment have an elongated shape which extends in a y-direction. To help with the explanation, piezoionic ionically conductive elements 704 are labelled and referred to herein as 704-1, 704-2, 704-3, 704-4, 704-5 . . . 704-m, where m is any suitable positive integer, it being appreciated that the number m of y piezoionic ionically conductive elements 704 may vary for particular surfaces 710 and/or particular applications. The ends of piezoionic ionically conductive elements 704 may be provided with electrically conductive electrodes 712. Electrodes 712 may be fabricated from suitable metals, metal alloys or the like. Electrodes 712 are located at opposing (in the y-direction) edges of piezoionic ionically conductive elements 704. To help with the explanation, electrodes 712 are labelled and referred to herein as 712-1A, 712-1B; 712-2A, 712-2B; 712-3A, 712-3B; 712-4A, 712-4B; 712-5A, 712-5B; . . . 712-mA, 712-mB, where m is any suitable positive integers, it being appreciated that the number m of electrodes 712 may vary for particular surfaces 710 and/or particular applications.

In the particular case of the FIG. 8A illustration, where second surface 110 is shown as being planar, the x and y directions may be considered to have generally constant spatial orientations which are the Cartesian x and y orientations shown in FIG. 8A. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 8A illustration, where sensing surface 110 is shown as being planar, the z direction shown in FIG. 8A may be considered to have generally constant spatial orientation which corresponds to the Cartesian z orientations shown in FIG. 8A. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

Figure 8B:
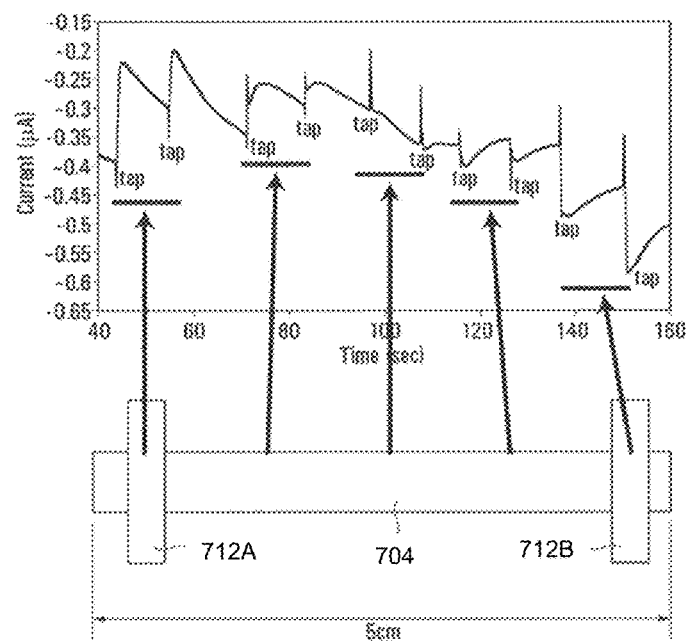
FIG. 8B is a graphical representation depicting current responses of a sample sensor of the FIG. 8A sensor array according to one embodiment of the invention.

During use, each electrode 712 is connected (e.g. through a MUX) to a suitable voltage readout circuit (not shown in FIG. 8A) for measuring the electrical signal between pairs of electrodes 712 at opposing ends of piezoionic ionically conductive elements 704 (e.g. electrode pair 712-1A, 712-1B, electrode pair 712-2A, 712-2B . . . ). When a region on sensing surface 110 is touched or otherwise subjected to pressure, mobile ions are redistributed in the affected piezoionic ionically conductive element 704 and the effect of the redistribution spreads from the location of the touch, such that a voltage across the pair of electrodes 712 corresponding to any affected piezoionic ionically conductive element 704 changes. For example, if a portion of sensing surface 110 is touched corresponding to the piezoionic ionically conductive element 704-1, it is expected a electrical signal (e.g. current and/or voltage) would be generated between electrodes 712-1A, 712-1B. It is expected that the amplitude of the current/voltage generated is greater as the touch (pressure) is located further from a location on piezoionic ionically conductive element 704-1 that is equidistant between electrodes 712-1A, 712-1B. Moreover, touches (pressure) located near one electrode (e.g. electrode 712-1A) may cause a positive current/voltage while touches located near the other electrode (e.g. electrode 712-1B) may cause a negative current/voltage. This can be seen from FIG. 8B which depicts a graphical representation of changes in current for touches/pressure located along an exemplary piezoionic ionically conductive element 704 having electrodes 712A and 712B. Thus, the location of the touch/pressure along a particular piezoionic ionically conductive element 704 may be determined based on detecting current changes at electrodes 712. Further, a location of the touch may be determined in two-dimensions by identifying which piezoionically ionically conductive element 704 was touched to achieve a location in the x direction and by detecting voltage/current changes at electrodes 712 of the touched piezoionic ionically conductive element 704 to determine a location in the y direction. It may also be possible, by using a suitable signal processing technique, to separately identify two touches occurring at the same time but at different locations, as the detected signals may be considered a superposition of the separate signals.

In some embodiments, sensor array 700 may be modified to include piezoionic ionically conductive elements 704 extending in the x direction as well as the y direction, similar to the embodiment depicted in FIG. 4A. In such an embodiment, the ionically conductive elements 704 can also provide two dimensional location information of one or more touches on sensing surface 110.

As will be appreciated by those of skill in the art, any suitable circuit may be implemented to detect the voltage difference between electrodes 712 in sensor array 700. As a non-limiting example, the electrical circuits of FIG. 1G or 1H could be used to detect the voltage difference between a pair of electrodes 712.

Figure 11A:
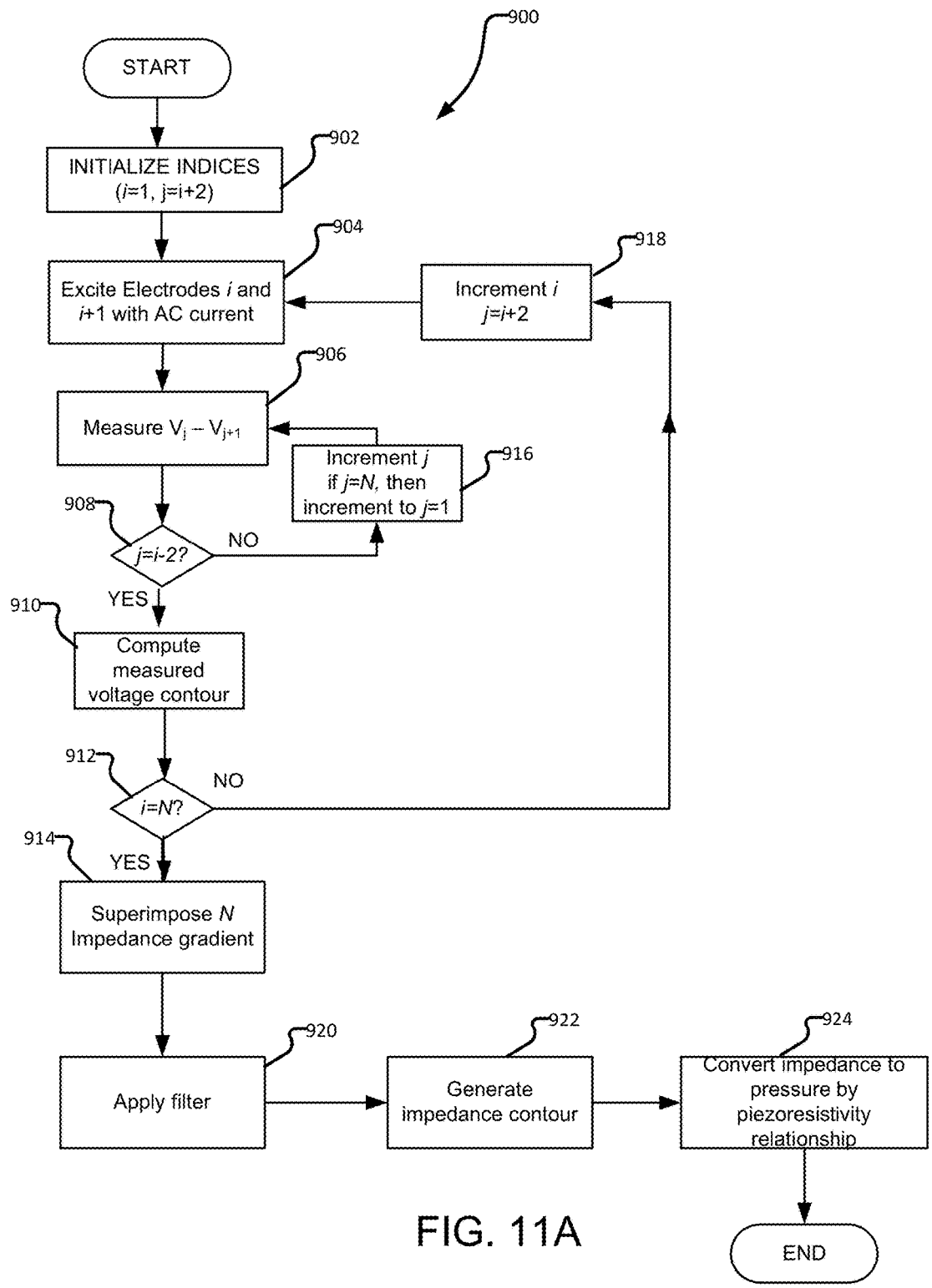
FIG. 11A schematically depicts a superposition (tomography) method for determining a pressure map of a sensing surface using the sensor array of FIG. 4B according to a particular embodiment.
Figure 11B:
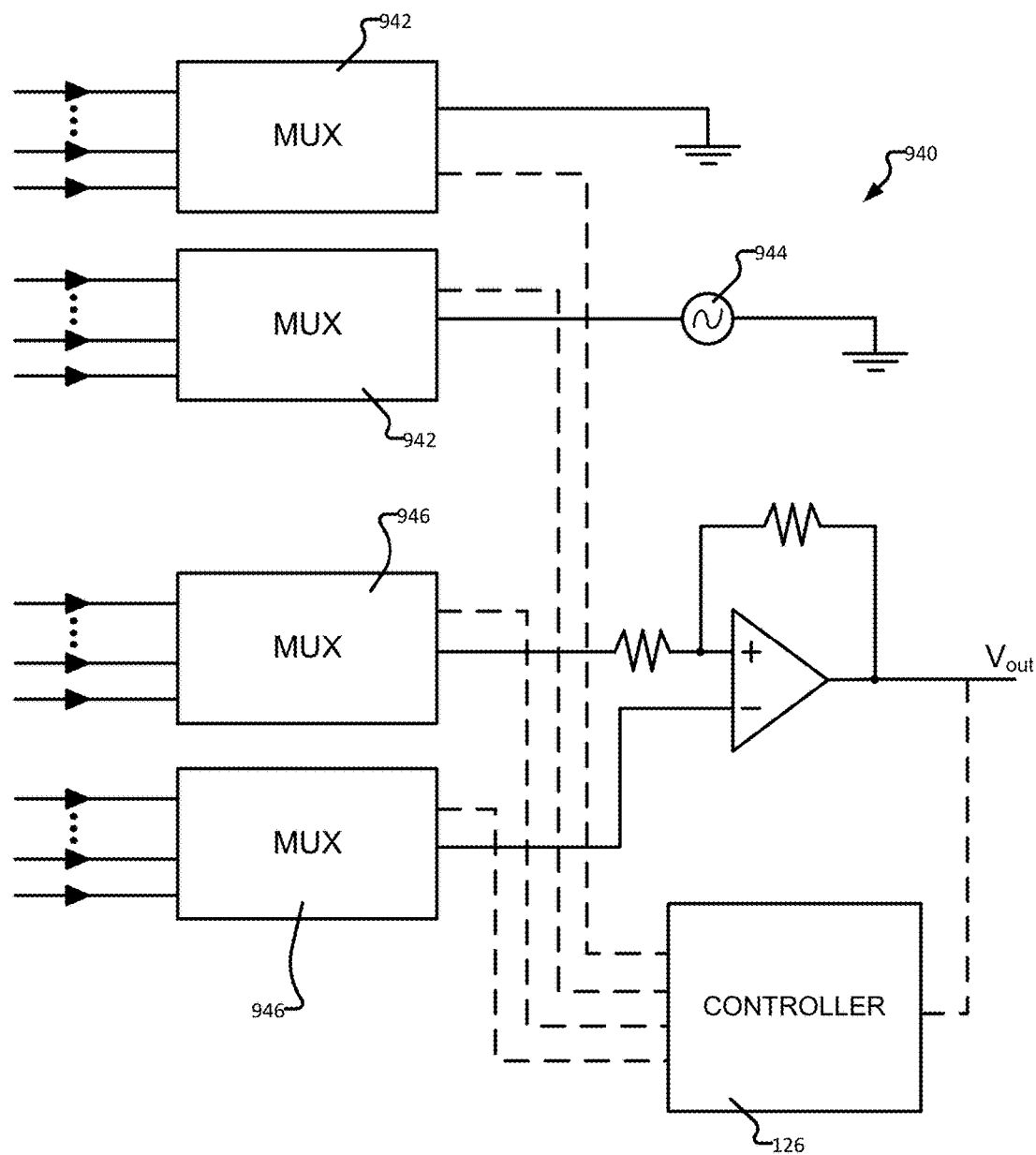
FIG. 11B schematically depicts a probing circuit that may be used for implementing the method of FIG. 11A according to a particular embodiment.
Figure 11C:
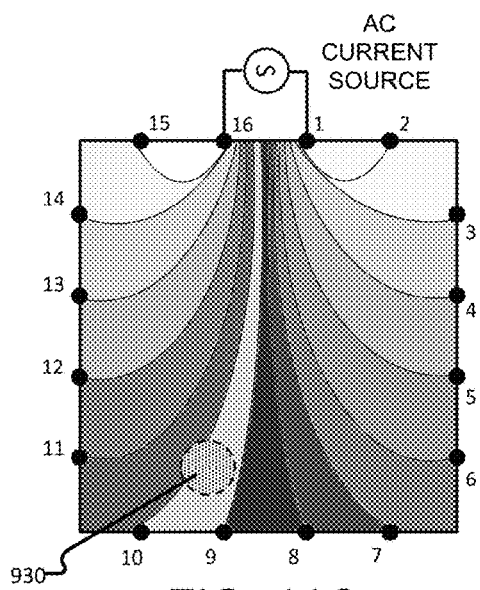
FIGS. 11C-11F show example measure voltage contours obtained in the method of FIG. 11A.
Figure 11D:
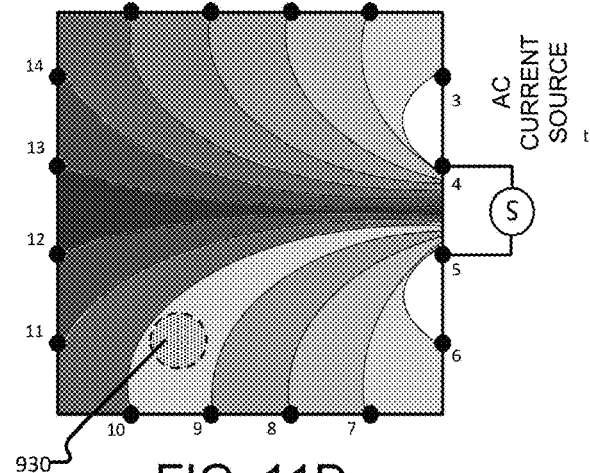

FIG. 11A schematically depicts a superposition (tomography) method 900 for determining a pressure map of a sensing surface 110 using the sensor array 440 of FIG. 4B according to a particular embodiment. Method 900 may be implemented by a suitably configured controller—e.g. controller 126 (FIG. 11B). Method 900 comprises applying a current signal between a first pair of electrodes 442 (e.g. an adjacent pair of electrodes 442 in the case of the illustrated embodiment) and then detecting the output voltage between a plurality of other pairs of electrodes (e.g. a plurality of adjacent electrodes 442 in the case of the illustrated embodiment). Then, the current signal is applied to a different pair of electrodes 442 and the process of detecting the output voltage at a plurality of other electrode pairs is repeated. This process of exciting a first pair of electrodes and measuring the output voltage at a plurality of other electrode pairs repeats several times and the results are superposed to obtain a pressure map. Method 900 shown in FIG. 11A uses the index i to refer to the first excited electrode (i.e. the first electrode on which a current signal is applied) and the index j to refer to the first measured electrode (i.e. the first electrode on which an output voltage is measured).

Method 900 starts in block 902 which initializes the indices. Then, method 900 proceeds to block 904 where AC current is applied between the electrodes 442 indexed by i and i+1. This is an adjacent pair of electrodes 442 in the illustrated embodiment. Method 906 then proceeds to block 906 which involves measure the voltage between electrodes 442 indexed by j and j+1. These are adjacent electrodes 442 in the illustrated embodiment. In the first iteration of block 906, these electrodes 442 will be the electrodes 442 adjacent to the excited electrodes i and i+1. By way of j-incrementing block 916 and inquiry 908, this process of measuring the output voltage between electrodes 442 indexed by j and j+1 is repeated for other pairs of electrodes 442. In the illustrated embodiment, this process measuring the output voltage between electrodes 442 indexed by j and j+1 is repeated for all pairs of adjacent electrodes 442 (except for the excited electrodes i and i+1), although this is not necessary. When this loop reaches the excited electrodes i and i+1, the block 908 inquiry is positive and method 900 proceeds to block 910.

In block 910, method 900 determines a measured voltage contour for the corresponding pair of excited electrodes i and i+1. FIG. 11O schematically depicts an example of a block 910 measured voltage contour, where regions of brighter colors correspond to larger voltage drops and the lines between colors correspond to isopotential lines (i.e. lines having the same potential). Electrodes 442 of FIG. 4B are enumerated 1-16 in the FIG. 11O example, but the principles of FIG. 11O are independent of the actual number of electrodes and could be used with the 20 electrodes shown in the exemplary FIG. 4B sensor array 440. Assuming that piezoresistive layer 444 (FIG. 4B) is uniform and the applied pressure is uniform, then the isopotential lines shown in FIG. 11O can be mathematically modelled based on the geometry of piezoresistive layer 444 and the locations of the electrodes 442. Accordingly, the isopotential lines shown in FIG. 11O can be predetermined for a given sensor array 440. It can be seen from FIG. 11O that the measured voltage is generally larger for pairs of measure electrodes that are closer to the excited electrodes. However, between electrodes 9 and 10 shown in FIG. 11O, pressure 130 has been applied to sensing surface 110 and, consequently, a larger than expected voltage (corresponding to a larger resistance) is measured between electrodes 9 and 10. Such a measurement is suggestive of relatively high pressure 130 being applied to sensing surface 110 in a space between electrodes 9 and 10.

Figure 11E:
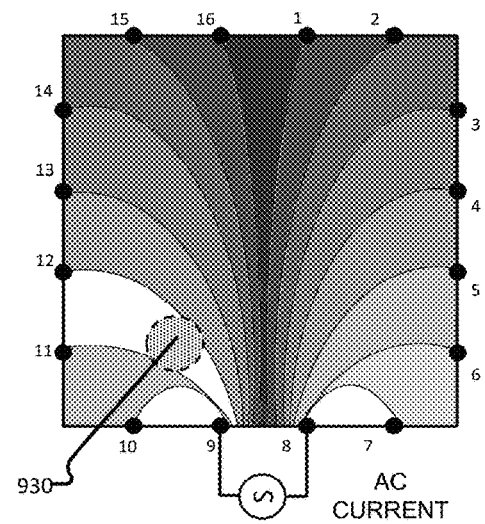

Via inquiry block 912 and incrementing block 918, measured voltage contours are determined in block 910 for a plurality of pairs of excitation electrodes. In the illustrated embodiment of method 900, each adjacent pair of electrodes for the given sensor array is used to generate a corresponding measured voltage contour in block 910. However, this is not strictly necessary and, in some embodiments, a subset of the available electrode pairs could be used to excite the sensor and to generate corresponding measured voltage contours in block 910. FIGS. 11O-11E show a number of representative block 910 measured voltage contours when relatively high pressure 130 is applied in one region of sensing surface 110.

Figure 11F:
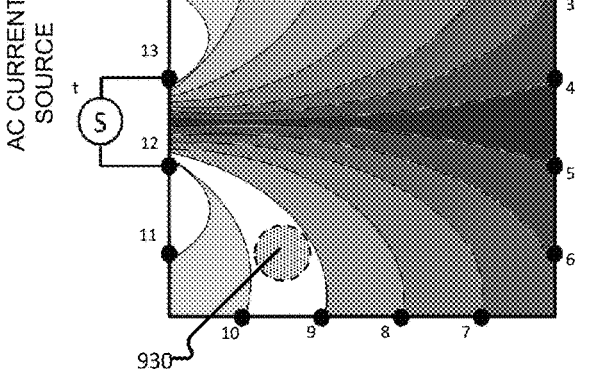
Figure 11G:
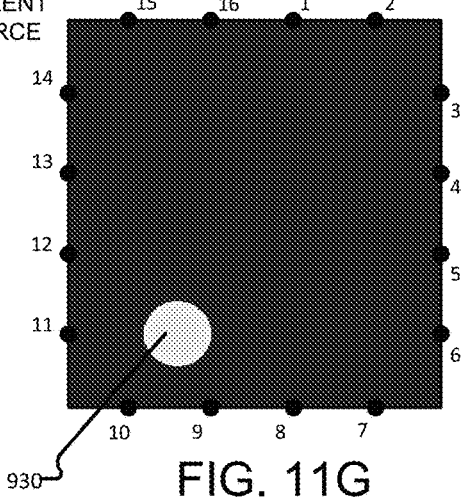
FIG. 11G shows an example impedance contour obtained from the measured voltage contours of FIGS. 11C-11F.

After block 910 measured voltage contours are determined for all of the excitation electrodes 442 of interest, method 900 exits from block 912 to block 914, where all of the previously obtained block 910 voltage contours are superposed to obtain a superposed voltage contour. The block 914 superposed voltage contour can optionally be filtered in 920 to smooth out discontinuities. In block 922, the block 914 superposed voltage contour (optionally filtered in block 920) can be used to generate an impedance contour. This may be done by dividing the superposed voltage contour by the current used to excite the various electrodes in the preceding loop. FIG. 11F schematically depicts the block 922 impedance contour resulting from the superposition of a sensor array having relatively high pressure 930 applied to a particular region of sensing surface 110. The block 922 impedance contour may then be converted to pressure using an empirically determined relationship between pressure and impedance for the particular piezoelectric material 444 used in sensor array 440.

FIG. 11B schematically depicts a circuit 940 which may be used to implement method 900. Circuit 940 comprises a pair of excitation MUXs 942 which may be selectively connected to any pair of electrodes 442 in sensor array 440 to thereby deliver a signal from current source 944. Circuit 940 also comprise a pair of measurement MUXs 946 which may be selectively connected to any pair of electrodes 442 in sensor array 440 to measure a voltage signal $V_{out}$ which may be provided to controller 126. It will be appreciated by those skilled in the art that circuit 940 may comprise a variety of signal conditioning elements and/or circuitry (not shown). By way of non-limiting example, such signal conditioning circuitry may comprise buffers, amplifiers, filtering elements, inverters, analog to digital converters and/or the like. Controller 126 may incorporate or otherwise have access to memory in which various input or output values of may be stored. Electrical circuit 940 is merely one example of a circuit suitable for use with method 900 and sensor array 440. In some embodiments, other circuits may be used.

Figure 9A:
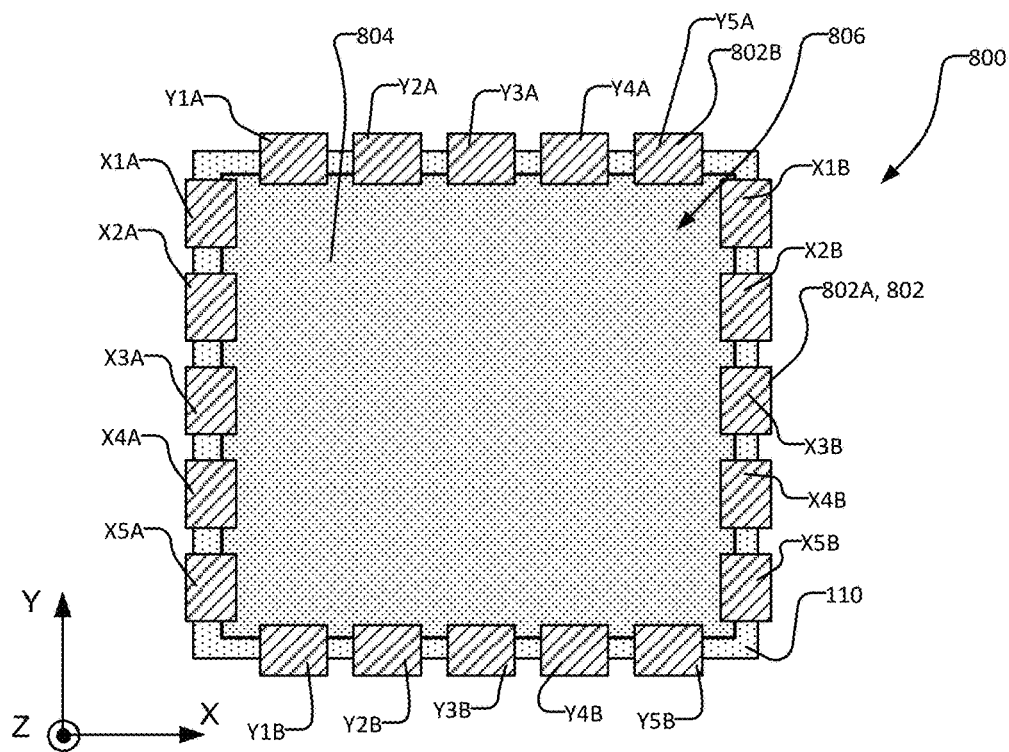
FIG. 9A depicts a sensor array for sensing the pressure over a sensing surface according to another particular embodiment.

FIG. 9A depicts a sensor array 800 for sensing the pressure over a sensing surface 110 according to another particular embodiment. By way of non-limiting example, sensing surface 110 may comprise or be provided on or adjacent to the surface of a bed sheet or mattress on which a person may be located (e.g. the surface of a hospital bed). The FIG. 9A sensor array 800 operates using a piezoionic principle using piezoionic layer 804 comprising ionically conductive material. In the illustrated FIG. 9A embodiment, sensing surface 110 being mapped is shown as being generally planar for ease of explanation, but this is not necessary and sensing surface 110 may generally have any shape to suit a corresponding application. In the FIG. 9A embodiment, sensor array 800 is distributed over a working region 806 that is adjacent to (e.g. in force transmitting contact with) sensing surface 110. Piezoionic layer 804 of the FIG. 9A embodiment spans at least a majority of working region 806. Piezoionic layer 804 may be fabricated from suitable piezoionic materials, such as, by way of non-limiting example, any suitable materials disclosed herein, in the '265 application or in the '238 application. Sensor array 800 comprises a number of electrodes 802A, 802B (collectively electrodes 802) distributed about the edges of piezoionic layer 804. Electrodes 802 are electrically conducting and may be fabricated from suitable metals, metal alloys or the like. Electrodes 802A are located at opposing (in the x-direction) edges of piezoionic layer 804 and may be referred to herein as x-electrodes 802A and electrodes 802B are located at opposing (in the y-direction) edges of piezoionic layer 804 and may be referred to herein as y-electrodes 802B. To help with the explanation, opposed x-electrodes 802A are also labelled x1A, x1B; x2A, x2B; x3A, x3B . . . xnA, xnB and opposed y-electrodes 802B are also labelled and referred to herein as y1A, y1B; y2A, y2B; y3A, y3B . . . ymA, ymB, where n and m are any suitable positive integers, it being appreciated that the number of n of x-electrodes 802A and the number m of y-electrodes 802B may vary for particular sensing surfaces 110 and/or particular applications.

In the particular case of the FIG. 9A illustration, where sensing surface 110 is shown as being planar, the x and y directions may be considered to have generally constant spatial orientations which are the Cartesian x and y orientations shown in FIG. 9A. However, where sensing surface 110 is a general (e.g. non-planar) surface, the orientations of the x and y directions may vary in space and may be understood to be locally tangential to sensing surface 110 and non-parallel to one another so as to span sensing surface 110. In some embodiments, the x and y directions may be mutually orthogonal at any given point on sensing surface 110. Similarly, in the particular case of the FIG. 9A illustration, where sensing surface 110 is shown as being planar, the z direction shown in FIG. 9A may be considered to have generally constant spatial orientation which corresponds to the Cartesian z orientations shown in FIG. 9A. However, where sensing surface 110 is a general (e.g. non-planar) surface, the orientation of the z direction may vary in space and may be understood to be locally normal to sensing surface 110. In some embodiments, the z direction may be orthogonal to the x and y directions at any given point on sensing surface 110.

A piezoionic pressure sensing array may be implemented by piezoionic layer 804. For example, voltages may be measured between opposing x-electrodes 802A of sensor array 800 (e.g. between electrodes x1A, x1B; or x3A, x3B) and may be responsive to pressure exerted on sensing surface 110 and corresponding deformation of piezoionic layer 804 in a region between the opposing x-electrodes 802A. Similarly, voltages may be measured between opposing y-electrodes 802B of sensor array 800 (e.g. between electrodes y1A, y1B; or y3A, y3B) and may be responsive to pressure exerted on sensing surface 110 and corresponding deformation of piezoionic layer 804 in a region between the opposing y-electrodes 802B. Measuring voltages between pairs of electrodes 802 in the FIG. 9A embodiment is not limited to opposing x-electrodes 802A or opposing y-electrodes 802B. In some embodiments, voltages may be measured between any pair of electrodes 802 in sensor array 800 (e.g. a pair of electrodes 802 comprising any pair of x-electrodes 802A and y-electrodes 802B) to detect pressure exerted on sensing surface 110 and corresponding deformation of piezoionic layer 804 in a region between the pair of electrodes 802.

Sensor array 800 of FIG. 9A may be used to generate a pressure map for sensing surface 110 using a superposition (tomography) method similar to that method 900 described in FIG. 11A. Unlike the piezoresistive case described in method 900, piezoionic sensor array 900 does not need to be excited (although it can be in some embodiments). A superposition method implemented on sensor array 800 involves obtaining a plurality of independent voltage measurements corresponding to a plurality of electrodes 802 located around sensor array 800. Such voltage measurements could be measurements of voltages at individual ones of electrodes 802 measured relative to some reference voltage (e.g. ground) or differential voltage measurements between pairs of electrodes 802 (e.g. adjacent pairs of electrodes). In general, using a larger number of independent voltage measurements distributed around piezoionic layer provide finer resolution. A circuit like the circuits 1G or 1H described elsewhere herein could be used to obtain these voltage measurements. These measurements may then be used to solve for a voltage at each considered electrode 802.

Figure 9B:
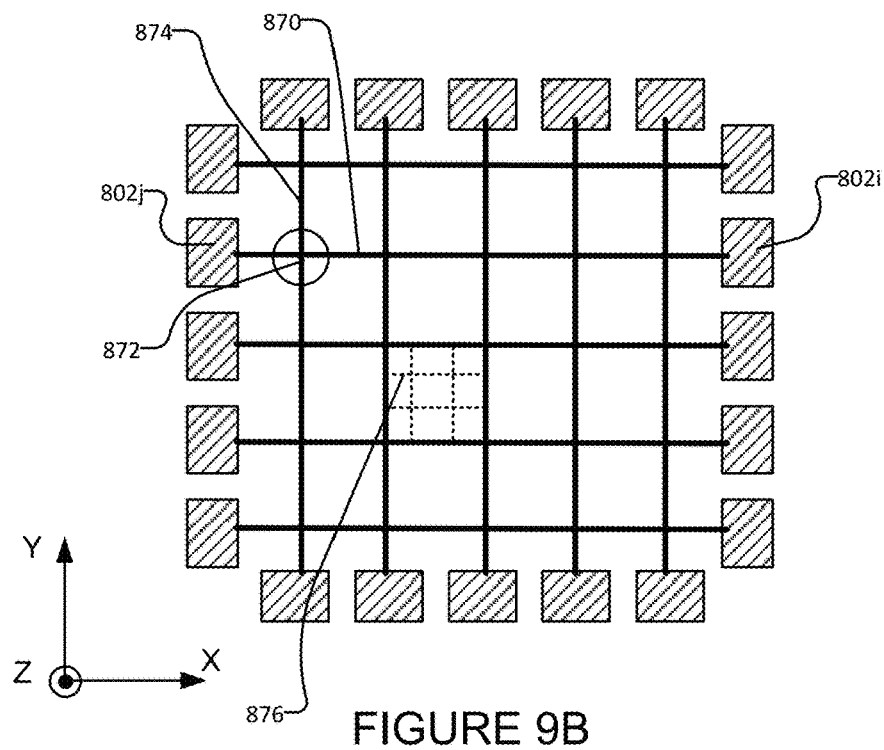
FIG. 9B schematically depicts a meshing process used to generate a pressure map of the FIG. 9A sensor array according to a particular embodiment.

Once these voltages are known for each considered electrode 802, sensing surface 110 may be meshed between electrodes 802. Any suitable meshing pattern could be used to parse up the sensing surface 110 between electrodes 802 into a mesh of intersecting lines between electrode pairs. A non-limiting example is shown in FIG. 9B. Then, based on the voltages measured at each electrode 802, the each mesh line may be assumed to have a linear potential drop between the electrodes 802. For example, in the FIG. 9B illustration, a linear voltage drop may be assumed on the mesh line 870 between the voltages at electrodes 802i and 802j. This assumption allows the prediction of specific voltages anywhere each mesh line between a corresponding pair of electrodes. Then, at intersections between mesh lines (e.g. at intersection 872 between mesh line 870 and mesh line 874, each intersection may be assigned a value based on a combination (e.g. a sum or average) of the values for the intersecting mesh lines. According to this technique, voltage values may be assigned for each mesh line intersection. If desired, finer meshes may be created between groups of mesh line intersections and the process can be repeated to obtain finer resolutions. An example of such a finer mesh 876 between a plurality of intersecting lines of the original mesh is shown in FIG. 9B. Once again, this finer mesh can be designed in any suitable manner that results in a plurality of intersecting finer mesh lines. Finally, once voltages are known for a plurality of mesh line intersections (and/or finer mesh line intersections) this voltage map maybe converted to a pressure map based on empirically determined relationship between voltage and pressure for piezoionic layer 804.

Sensor arrays 300, 300' shown in FIGS. 3A and 3B (collectively referred to hereinbelow as sensor array 300, unless the context dictates otherwise) may additionally or alternatively be used to estimate moisture maps corresponding to a sensing surface 110 (e.g. where the sensing surface is in moisture-transmitting contact with the sensor array). As discussed above, sensor arrays 300 comprise ionically conductive electrodes 304 disposed on either side of a dielectric material 302. Dielectric material 302 may be selected to be breathable or to be otherwise capable of absorbing (at least temporarily) moisture, including, by way of non-limiting example, liquid water and/or water vapor. The presence of localized moisture in the dielectric layer 302 will have an impact on the local dielectric constant of the dielectric material 302 and, consequently, will impact the impedance of the sensor elements in corresponding overlap regions $(x_i, y_j)$. In particular, the presence of moisture in dielectric layer 302 in a vicinity of an overlap region $(x_i, y_j)$ may increase both the capacitance and the resistance as between the overlapping electrodes $(x_i, y_j)$.

Methods for determining a moisture map may comprises estimating the impedance (e.g. the resistance $R_{xi,yi}$ and/or the capacitance $C_{xi,yi}$) between individual pairs of overlapping electrodes $(x_i, y_j)$ of sensor 300. Estimating the impedance between individual pairs of overlapping electrodes $(x_i, y_j)$ may comprise, for each individual pair of overlapping electrodes $(x_i, y_j)$, subjecting the pair of overlapping electrodes $(x_i, y_j)$ to a variable frequency input signal and obtaining a frequency response for the pair of overlapping electrodes $(x_i, y_j)$. FIG. 5A shows a model circuit between a pair of overlapping electrodes $(x_i, y_j)$ in the sensor arrays 300, 300' of FIG. 3A. The impedance of this FIG. 5A circuit in the Laplace domain is given by $$z_{EQ} = \frac{R}{1 + sCR}$$

where s is the Laplace variable s=jω, where ω is the angular frequency and j=√−1. It can be seen from this impedance formula, that at frequencies close to zero, the impedance will be equal to R, since the capacitor is open circuited and that at high frequencies the capacitor C will dominate the imped-ance. The amplitude component of a variety of typical frequency response curves for a pair of overlapping electrodes $(x_i, y_j)$ are shown in FIG. 5B. Determining values for R and C for a pair of overlapping electrodes $(x_i, y_j)$ may comprise subjecting the pair of overlapping electrodes $(x_i, y_j)$ to a variable frequency input signal, obtaining the frequency response and then performing a curve fitting operation to ascertain values for R and C that will best approximate the measured frequency response. Any suitable curve fitting technique, such as, by way of non-limiting example, a Levenberg-Marquardt algorithm, may be used for this purpose.

It can be seen from the shape of the FIG. 5 curves that for low frequencies, the impedance magnitude approaches the value R. Consequently, it may be possible to determine the quantity R (and the corresponding moisture content) without subjecting the pair of overlapping electrodes $(x_i, y_j)$ to a full range of variable frequency input signals and/or without performing a complete curve fitting technique to the frequency response. In some embodiments, a variable frequency input signal is not required and the values of R and C may be determined for example using a DC signal and a single frequency and/or a step response or the like. For a given sensor geometry, a relationship between the moisture content level in a portion of the dielectric layer 302 corresponding to an overlap region $(x_i, y_j)$ and a resistance between the corresponding pair of overlapping electrodes $(x_i, y_j)$ may be experimentally determined and stored in a look up table or the like which is accessible to a suitable controller (e.g. controller 126 described herein). In this manner, determining the resistance R for a pair of overlapping electrodes $(x_i, y_j)$ may be used to estimate the moisture content in a region of sensing surface 110 corresponding to overlap region $(x_i, y_j)$ and a moisture map corresponding to sensing surface 110 can thereby be determined by traversing the various overlap regions $(x_i, y_j)$ of a sensor array.

With the value of R known from the low frequency response (as discussed above), the curve fitting technique used to fit the measured frequency response of a pair of overlapping electrodes $(x_i, y_j)$ may be performed to ascertain the value of the capacitance C. Once the capacitance C is known, it may be desirable to interpret this capacitance, since the capacitance can vary with both pressure (as discussed above) and moisture content. One method by which the impact of pressure and moisture content may be distinguished (e.g. to determine the pressure from the measured capacitance C) may comprise having a plurality of look up tables which relate a measured capacitance C to pressure, with each look up table having an associated moisture content. Such look up tables can be determined experimentally, for example. Since the moisture content is determinable from the low frequency response and the resistance value R, as described above, it is possible to determine which look up table to select for the purposes of selecting a pressure corresponding to the measured capacitance.

Another method for by which the impact of pressure and moisture content may be distinguished (e.g. to determine the pressure from the measured capacitance C) may comprise interpreting the known moisture content to modify the dielectric constant E. For instance, if it is determined from the moisture level that 50% of by volume of the dielectric material 302 is filled with water, then the dielectric constant ∈ may be to have a new value (e.g. to set ∈=40, where ∈=1 corresponds to air and ∈=80 corresponds to water) and then the thickness t of the dielectric layer can be computed according to equation (11). The thickness t determined from equation (11), which is actually the deformed thickness $t=t_0-\Delta t$, can then be used with equation (10) to determine the pressure for the overlap region $(x_i,y_j)$. In some embodiments, a look up table may be experimentally determined and used by a suitable controller (e.g. controller 126) to determine the relationship between the measured moisture content and the dielectric constant $\in$.

In some embodiments, it is desirable to implement surface moisture sensing independently of pressure sensing in which case sensor array 300 can be used for moisture sensing. In some embodiments, it may be desirable to implement moisture sensors within a surface sensor array so that moisture can be detected separately from pressure (e.g. by having moisture sensors with a lower spatial frequency than pressure sensors). For example, every $i^{th}$ overlap region (where i can be any suitable integer) may be dedicated to moisture measurement, whereas the other overlap regions can be used for pressure. In some embodiments, any of the above described pressure measurement techniques may be calibrated to take moisture into account by a process similar to that described above for discerning the capacitive effect of pressure from moisture.

Figure 10A:
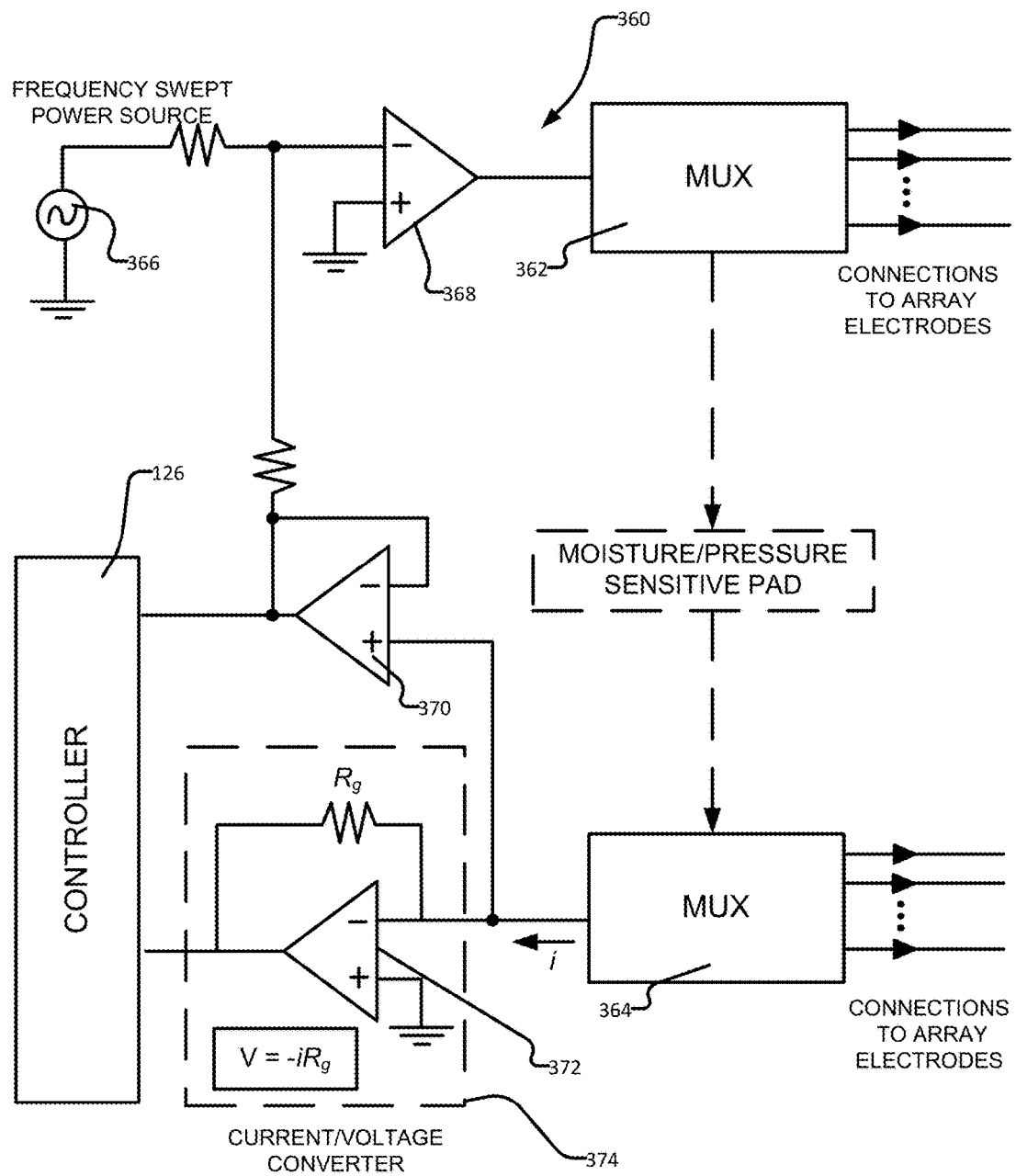
FIG. 10A schematically depicts a readout circuit that may be used for measuring the impedance of the individual sensor elements (i.e. an overlap region ($x_i$,$y_j$)) of the sensor arrays shown in FIGS. 3A and 3B according to a particular embodiment.

FIG. 10A schematically depicts a readout circuit 360 that may be used for measuring the impedance of the individual sensor elements (i.e. an overlap region $(x_i,y_j)$) of sensor arrays 300, 300' shown in FIGS. 3A and 3B according to a particular embodiment. Circuit 360 is described with reference to sensor array 300 without loss of generality. Circuit 360 comprises a first MUX 362 capable of effecting connections to any of the ionically conductive row electrodes 304A and a second MUX capable of effecting connections to any of the ionically conductive column electrodes 304B. MUXs 362, 364 may be controlled by controller 376 (although, for simplicity, such control is not explicity shown in FIG. 10A). Circuit 360 comprises a frequency sweeping AC (e.g. sinusoidal) power source 366 for exciting each overlap region of sensor array 300 with AC signals of different frequencies, so that controller 126 can determine the frequency response of each overlap region. Circuit 360 comprises a first operational amplifier 368 which functions as a driving amplifier for power source 366 and supplying AC signal to MUX 362, a second operational amplifier 370 which is a unity gain amplifier for delivering the voltage output from MUX 364 to controller 126 and a third operational amplifier 372 which functions as a current to voltage converter by outputting a voltage v to controller 126, where the voltage v is proportional to the current i output from MUX 364 according to $v=-iR_g$. Controller 126 may then use the ratio of the voltage output from op-amp 370 and the voltage (which is representative of the current) output from op-amp 372 as the impedance of the current overlap region.

It will be appreciated by those skilled in the art that circuit 360 may comprise a variety of signal conditioning elements and/or circuitry (not shown) between amplifiers 370, 372 and controller 126. By way of non-limiting example, such signal conditioning circuitry may comprise buffers, amplifiers, filtering elements, inverters, analog to digital converters and/or the like. Controller 126 may incorporate or otherwise have access to memory in which various input or output values of may be stored. Electrical circuit 360 is merely one example of a voltage amplification circuit suitable for determining impedances of overlap regions in sensor arrays 300, 300'. In some embodiments, other impedance measuring circuits may be used.

Figure 10B:
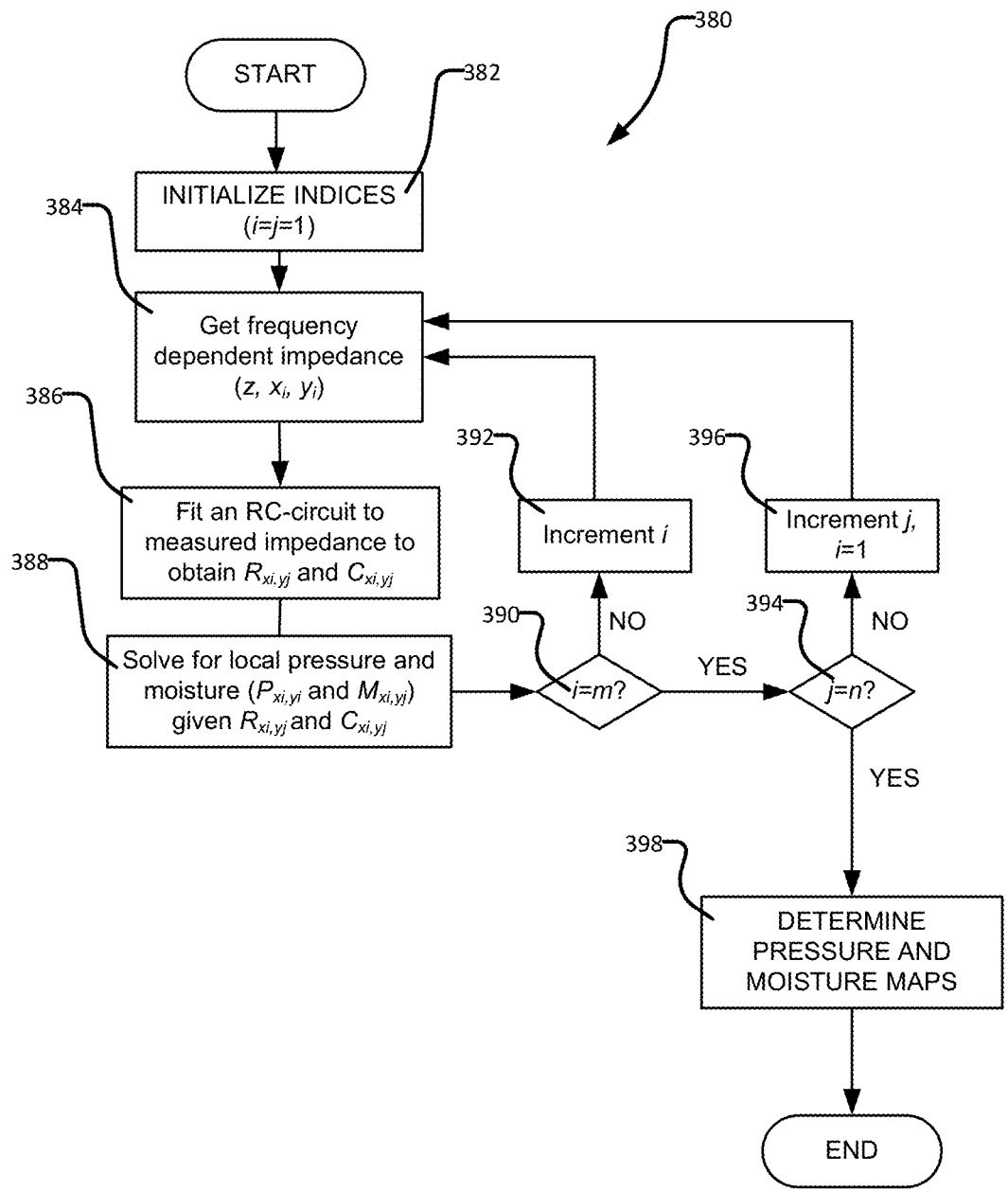
FIG. 10B shows an example of a method for determining pressure and moisture maps of a sensing surface using the sensor arrays shown in FIGS. 3A and 3B according to a particular embodiment.

FIG. 10B shows an example of a method 380 for determining pressure and moisture maps of a sensing surface 110 using the sensor arrays 300, 300' shown in FIGS. 3A and 3B according to a particular embodiment. Method 380 may be implemented by controller 126. Method 380 is explained in connection with sensor array 300 without loss of generality. It will be appreciated that method comprises a loop over the overlap regions $(x_i,y_j)$ in sensor array 300, which is implemented by initialization block 382, index increment blocks 392, 396 and inquiry blocks 390, 394. For each overlap region $(x_i,y_j)$ in sensor 300, method 380 obtains a frequency dependent impedance response $z_{ij}$. The frequency dependent impedance response may be obtained by circuit 360 (FIG. 10A) described above, for example. FIG. 5B shows a number of examples of these frequency dependent impedance responses. For each overlap region $(x_i,y_j)$ in sensor 300, method 380 then proceeds to block 386, where the block 384 frequency response is fit to the frequency response curve of a representative RC circuit (e.g. the RC circuit shown in FIG. 5) to yield resistance and capacitance values $R_{xi,yi}$, $C_{xiyj}$ for the overlap region $(x_i,y_j)$. For each overlap region $(x_i,y_j)$ in sensor 300, method 380 then proceeds to block 388 which involves estimating the pressure $P_{xiyj}$ and moisture $M_{xiyj}$ for the current overlap region $(x_i,y_j)$. Block 380 may involve solving a system of equations of the form $$C = \frac{\in (M)A}{d(P)} \text{ and } C = \frac{d(P)}{\sigma(P)A},$$

where M is the moisture, P is the pressure, $\varepsilon(M)$ is the permittivity of the dielectric (which is a function of the moisture M), d(P) is the thickness of the dielectric (which is a function of the pressure P), and $\sigma(P)$_is the conductivity of the overlap region (which is a function of moisture M). The relationships $\varepsilon(M)$, d(P) and/or $\sigma(P)$ may be emprically or experimentally determined and may be stored in look-up tables in a memory accessible to controller 126, for example. Once the pressure P and moisture M are known for all of the overlap regions in sensor array 300, then method 380 exits the loop and proceeds to block 398 where the pressure and moisture maps spanning sensing surface 110 may be assembled and stored or displayed, for example.

One non-limiting example of where the surface sensor arrays described herein may be employed is on a surface located in or on a mattress of a bed (e.g. in, on or adjacent to a bed sheet), to detect a pressure map and/or a moisture map associated with anyone located on top of the bed. Other similar examples where surface sensor arrays described herein may be used include in, on or adjacent to seats or chairs (e.g. vehicle (automobile) seats, wheel chairs and/or the like). A pressure sensor array implemented in, on or adjacent a mattress of a bed or in, on or adjacent to chair or seat may be monitored and used for a variety of applications. Such applications include, without limitation, monitoring body weight and pressure distribution, detecting and monitoring heart rate, detecting and monitoring respiratory rate, detection of restless leg syndrome (RLS), detection of seizures, detecting tremors associated with Parkinson's disease, sonic signals associated with organ activity (e.g. heart (phonocardiogram) and/or lung (phonorespirogram)) and/or the like. Some such applications may involve sensing characteristic frequencies of various types of events. Some embodiments may be tuned to provide increased accuracy at such frequency ranges and/or to discriminate various frequency ranges from one another. Moisture may additionally or alternatively be monitored by such sensor arrays to detect urination, perspiration and/or the like. Surface sensor arrays implemented in or on a mattress of a bed can be used in conjunction with suitable actuators to remind an individual to move and/or to actually move the individual. Such actuators may be triggered based on body weight and pressure distribution information detected using the sensor array—i.e. to strategically trigger particular actuators. Such reminders and/or physical movement can be used to help minimize bed sores, ulcers, RLS, sleep apnea and/or the like.

A sensor or array of sensors disclosed herein may be used in flexible electronics and hand held devices, or in an artificial skin for robotics applications. The sensors may be made biocompatible by selecting specific ionically conductive hydrogels as the conductive elements and using NaCl as the salt for the electrolyte. It is expected that suitable materials can be selected to embed such sensors into an artificial skin for replacing a human skin. The sensors may also be applied to the surface of the skin for medical applications or for entertainment applications. For example, pressure sensors described herein can be used as part of a drug dispensing patch to enable user or physician input for control of dosage. It may be used as an arm-band for interactions with users of a mobile music system such as an iPod™ or phone. With the use of biocompatible materials, it is expected that sensors disclosed herein can find various applications in the medical field.

A possible medical application of a ionically conductive sensor array disclosed herein is to use the sensor as part of a layer that conforms to a human body such as in an artificial skin. For example, artificial skin patches may be used to detect force, temperature, skin conductance, and other physiological parameters. Thin film transistor circuits or micro-fabricated electronics may be integrated in a thin adhesive film, which can be attached to a robotic or human body. A ionically conductive sensor array of the types disclosed herein may be imbedded in such thin film or skin patches to provide further flexibility, compliance, biocompatibility, and tune-ability of materials, to accommodate different body parts (even in vivo), possible integration with a therapeutic system such as drug pumping. Potential physiological parameters that may be detected or measured with an ionically conductive sensor based smart patch include: cardio-seismography derived heart rate, electrocardiogram, blood pressure, respiratory rate based on chest movements, respiration depth, tidal volume, oxygen saturation, electroencephalogram, vigilance, relaxation, digestion, emotion and stress level, or the like.

For example, an ionically conductive sensor may be provided in a wearable stethoscope. Patients may discretely attach such sensor patches on their chests such that the ionically conductive sensor in the patch can transduce acoustic and seismographic profiles continuously, enabling diagnosis of certain medical conditions, such as various heart conditions including mitral regurgitation, aortic regurgitation, arrhythmia, and etc. The wearable patch may contain an RF (radio frequency) transmitter so that signals can be wirelessly transmitted to a separate computer for processing. An ionically conductive sensor disclosed herein may be able to detect signals with a dynamic frequency range suitable for both the bell-mode (low frequency: breathing sounds) operation and the diaphragm-mode (high frequency: heart murmurs, blood perfusion) operation of a typical stethoscope.

Other non-limiting applications for surface sensor arrays described herein include, for example, on the floors of buildings to detect wet floors and the potential for human injury and/or to detect patterns of human movement atop the floor. For example, the floor of a retail outlet or subway station could be monitored to see how many people traverse a section of the floor in a given day or in a given hour. Other non-limiting applications for surface sensor arrays of the type described herein include, for example, in so-called "G-suits" to help astronauts and/or pilots by monitoring gravitational forces experienced by the astronauts or pilots and possibly to take supportive action in a case where the gravitational forces are ascertained to be too high.

Exemplary embodiments are illustrated in referenced figures of the drawings. It is intended that the embodiments and figures disclosed herein are to be considered illustrative rather than restrictive.

While a number of exemplary aspects and embodiments are discussed herein, those of skill in the art will recognize certain modifications, permutations, additions and sub-combinations thereof. For example:

- A number of the embodiments described herein comprise traversing various elements of sensor arrays in particular orders. This is not generally necessary. In some embodiments, the orders in which the elements of sensor arrays are traversed may be varied.
- In some embodiments or applications, it is not necessary to traverse every sensor element. In some embodiments, a sensor array can be undersampled.
- In some of the embodiments described above, various measure parameters (e.g. voltages, capacitances, resistance, pressures and/or the like) are described as being compared to reference parameters. In some instances, the reference parameters may be set to zero for convenience (e.g. because for many applications relative pressure may be more important than having a precise measurement of absolute pressure), but this is not necessary. In some instances, the reference parameters may be set to non-zero values and relative parameters may be obtained relative to these non-zero reference values. In some embodiments, the reference parameters may be static or may be associated with particular sensor elements. This is not necessary, however. In some embodiments, the reference parameters may be changed or the sensor elements used as reference sensor elements may be changed dynamically. In some such embodiments, a detected parameter for any taxel may comprise a differential parameter relative to that of the reference element/taxel. In such cases, it may be desirable to integrate the detected differential parameter relative to the reference parameter of the reference element/taxel to ascertain an absolute value of the parameter for the current taxel. Such integration techniques may be used for example in the methods of 2A and/or 2B.
- Sensing surface 110 described in the embodiments above may be implemented as a wearable surface, which may be operatively connected to a wearer. Such operative connection may involve adhesively connecting to a wearer (e.g. an adhesive patch and/or the like), elastically deformation to fit over a portion of a wearer's body and then connecting to the wearer by restorative deformation (e.g. a tensor bandage, compression garments and/or the like), connecting to the wearer's body using a closure mechanism (e.g. a zipper, snap mechanism or the like), connecting to a wearer by pressure of wearer's body (e.g. footbeds in a shoe, clothing worn in bed and/or the like).
- In some embodiments, dielectric materials used in the sensor arrays described above may comprise spatially varying stiffness/deformability within the overlap regions. These microstructured spatial variations can enhance deformability (for given pressures) and result in greater output (e.g. voltage) variation for a given pressure variation.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

What is claimed is:

1. A flexible sensor array for detecting pressure at one or more locations over a sensing surface, the sensor array comprising:
   a first plurality of conductive electrodes distributed over a working region adjacent the sensing surface, each of the first plurality of electrodes elongated in an x-direction that is generally tangential to the sensing surface and a second plurality of conductive electrodes distributed over the working region, each of the second plurality of electrodes elongated in a y-direction, the y-direction generally tangential to the sensing surface and non-parallel with the x-direction;
   each of the first plurality of electrodes overlapping each of the second plurality of electrodes in a z-direction generally normal to the sensing surface at a corresponding overlap region;
   for each overlap region between one of the first plurality of electrodes and one of the second plurality of electrodes, a corresponding region of piezoionic polymer interposed between, and in conductive contact with, the one of the first plurality of electrodes and the one of the second plurality of electrodes in the z-direction, wherein the corresponding region of piezoionic polymer exhibits ionic conductivity which generates a corresponding first electrical signal at the one of the first plurality of electrodes relative to a first electrical signal reference and a corresponding second electrical signal at the one of the second plurality of electrodes relative to a second electrical signal reference, the first and second corresponding electrical signals depending on a state of deformation of the corresponding region of piezoionic polymer.

2. A sensor array according to claim 1 wherein the piezoionic polymer comprises a contiguous layer of piezoionic polymer interposed between the first plurality of electrodes and the second plurality of electrodes in the z-direction and each corresponding region of piezoionic polymer is part of the contiguous layer.

3. A sensor array according to claim 1 wherein, for each overlap region between one of the first plurality of electrodes and one of the second plurality of electrodes, the corresponding electrical signal at the one of the first plurality of electrodes relative to the first electrical signal reference comprises at least one of: a voltage difference between the one of the first plurality of electrodes and the first electrical signal reference, the voltage difference depending on the state of deformation of the corresponding region of piezoionic polymer; and a current flow between the one of the first plurality of electrodes and the first electrical signal reference, the current flow depending on the state of deformation of the corresponding region of piezoionic polymer.

4. A sensor array according to claim 3 wherein, for each overlap region between one of the first plurality of electrodes and one of the second plurality of electrodes, the first electrical signal reference is another one of the first plurality of electrodes.

5. A sensor array according to claim 3 herein wherein the another one of the first plurality of electrodes is common for a least a sub-plurality of the first plurality of electrodes.

6. A sensor array according to claim 3 wherein, for each overlap region between one of the first plurality of electrodes and one of the second plurality of electrodes, the first electrical signal reference is an adjacent one of the first plurality of electrodes.

7. A sensor array according to claim 3 wherein, for each overlap region between one of the first plurality of electrodes and one of the second plurality of electrodes, the first electrical signal reference is a reference one of the second plurality of electrodes.

8. A sensor array according to claim 3 wherein, for each overlap region between one of the first plurality of electrodes and one of the second plurality of electrodes, the first electrical signal reference is the one of the second plurality of electrodes.

9. A sensor array according to claim 1 comprising a sensing circuit connectable to amplify the first electrical signal for each overlap region and one or more multiplexers for connecting, for each overlap region, the one of the first plurality of electrodes and the first electrical signal reference to inputs of the sensing circuit to thereby cause the sensing circuit to amplify the first electrical signal.

10. A sensor array according to claim 9 comprising a controller connected to provide control signals to the one or more multiplexers and configured to output control signals which control the one or more multiplexers to iteratively scan over the overlap regions in the working region and, for each overlap region, to effect the connections of the one of the first plurality of electrodes and the first electrical signal reference to the inputs of the sensing circuit.

11. A sensor array according to claim 10 wherein, for each overlap region, the controller is configured to determine a pressure estimate for the overlap region based at least in part on the first electrical signal.

12. A sensor array according to claim 10 wherein the controller is configured to effect an iteration of a scan over the overlap regions in the working region with a frequency in a range of 10 Hz-20 Hz.

13. A sensor array according to claim 12 wherein the sensing surface comprises a surface of a bed.

14. A sensor array according to claim 13 wherein the sensor array is used to estimate one or more of heart rate, respiratory rate, body configuration and location of a person atop the bed.

15. A sensor array according to claim 13 wherein the sensor array is used to estimate body configuration and location of a person atop the bed and is used to trigger one or more actuators to provide tactile stimulus to the patient in the hospital bed, the triggering of the one or more actuators based at least in part on the estimated body configuration and location.

16. A sensor array according to claim 12 wherein the sensing surface comprises a surface of a chair and the sensor array detects pressure associated with a person sitting in the chair.

17. A sensor array according to claim 1 used in a garment wearable by a human and the sensing surface is a surface of the garment in contact with the human.

18. A sensor array according to claim 10 herein wherein the controller is configured to effect a scan iteration over the overlap regions in the working region with a frequency in a range of 60 Hz-120 Hz.

19. A sensor array according to claim 18 wherein the sensing surface comprises a surface of an electronic device and the sensor array detects pressure associated with a person interacting with the electronic device.

20. A sensor array according to claim 1 wherein the sensor array is in force-transmitting contact with the sensing surface.

21. A sensor array according to claim 1 wherein the sensing surface is non-planar.

22. A sensor array according to claim 1 wherein each electrode of the first and second pluralities of electrodes have transmissivities of over 90% at visible light wavelengths.

23. A sensor array according to claim 1 wherein at least one electrode of the first and second pluralities of electrodes is elastically deformable.

24. A method for generating a pressure map of a sensing surface comprising:
   providing a flexible sensor array comprising:
      a first plurality of conductive electrodes distributed over a working region adjacent the sensing surface, each of the first plurality of electrodes elongated in an x-direction that is generally tangential to the sensing surface and a second plurality of conductive electrodes distributed over the working region, each of the second plurality of electrodes elongated in a y-direction, the y-direction generally tangential to the sensing surface and non-parallel with the x-direction;
      each of the first plurality of electrodes overlapping each of the second plurality of electrodes in a z-direction generally normal to the sensing surface at a corresponding overlap region;
      for each overlap region between one of the first plurality of electrodes and one of the second plurality of electrodes, a corresponding region of piezoionic polymer interposed between, and in conductive contact with, the one of the first plurality of electrodes and the one of the second plurality of electrodes in the z-direction;
   for each one of the first plurality of electrodes detecting a first electrical signal at the one of the first plurality of electrodes relative to a first electrical signal reference;
   for each one of the second plurality of electrodes detecting a second electrical signal at the one of the first plurality of electrodes relative to a second electrical signal reference;
   for each overlap region between one of the first plurality of electrodes and one of the second plurality of electrodes, estimating a pressure value for the overlap region based at least in part on: the first electrical signal corresponding to the one of the first plurality of electrodes;
   and the second electrical signal corresponding to the one of the second plurality of electrodes.

25. A method according to claim 24 comprising:
   estimating a first average pressure corresponding to each one of the first plurality of electrodes based at least in part on the first electrical signal at the one of the first plurality of electrodes relative to the first electrical signal reference;
   estimating a second average pressure corresponding to each one of the second plurality of electrodes based at least in part on the second electrical signal at the one of the second plurality of electrodes relative to the second electrical signal reference; and
   wherein, for each overlap region between one of the first plurality of electrodes and one of the second plurality of electrodes, estimating the pressure value for the overlap region comprises estimating the pressure value based on at least in part on the first average pressure corresponding to the one of the first plurality of electrodes and on the second average pressure corresponding to the one of the second plurality of electrodes.

26. A method according to claim 25 wherein, for each overlap region between one of the first plurality of electrodes and one of the second plurality of electrodes, estimating the pressure value based on at least in part on the first average pressure corresponding to the one of the first plurality of electrodes and on the second average pressure corresponding to the one of the second plurality of electrodes comprises:
   scaling the first average pressure corresponding to the one of the first plurality of electrodes by a first scaling factor that depends on the second average pressure corresponding to the one of the second plurality of electrodes, to thereby obtain a first scaled value;
   scaling the second average pressure corresponding to the one of the second plurality of electrodes by a second scaling factor that depends on the first average pressure corresponding to the one of the first plurality of electrodes, to thereby obtain a second scaled value; and
   averaging the first and second scaled values to thereby obtain the pressure value for the overlap region.

27. A method according to claim 26 wherein, for each overlap region between one of the first plurality of electrodes and one of the second plurality of electrodes, the first scaling factor comprises a ratio of: the second average pressure corresponding to the one of the second plurality of electrodes; and a sum of the second average pressures over the second plurality of electrodes.

28. A method according to claim 25 wherein estimating the first average pressure corresponding to each one of the first plurality of electrodes based at least in part on the first electrical signal at the one of the first plurality of electrodes relative to the first electrical signal reference comprises, for each one of the first plurality of electrodes, the first average pressure based on an empirically determined relationship between the first electrical signal and the corresponding first average pressure.

29. A method according to claim 25 comprising, for each one of the first plurality of electrodes, subjecting the detected first electrical signal at the one of the first plurality of electrodes relative to the first electrical signal reference to a thresholding process and, if the detected first electrical signal is less than a threshold, setting the first average pressure corresponding to the one of the first plurality of electrodes to be equal to atmospheric pressure.

30. A method for generating a pressure map of a sensing surface comprising:
   providing a flexible sensor array comprising:
      a first plurality of conductive electrodes distributed over a working region adjacent the sensing surface, each of the first plurality of electrodes elongated in an x-direction that is generally tangential to the sensing surface and a second plurality of conductive electrodes distributed over the working region, each of the second plurality of electrodes elongated in a y-direction, the y-direction generally tangential to the sensing surface and non-parallel with the x-direction;

each of the first plurality of electrodes overlapping each of the second plurality of electrodes in a z-direction generally normal to the sensing surface at a corresponding overlap region;

for each overlap region between one of the first plurality of electrodes and one of the second plurality of electrodes, a corresponding region of piezoionic polymer interposed between, and in conductive contact with, the one of the first plurality of electrodes and the one of the second plurality of electrodes in the z-direction;

for each overlap region:

detecting at least one electrical signal wherein the at least one electrical signal depends on a state of deformation of the corresponding region of piezoionic polymer; and estimating a pressure value for the overlap region based at least in part on the at least one electrical signal;

wherein, for each overlap region, detecting the at least one electrical signal comprises:

detecting a first electrical signal at the one of the first plurality of electrodes relative to a first electrical signal reference; and detecting a second electrical signal at the one of the second plurality of electrodes relative to a second electrical signal reference;

wherein the first and second electrical signals depend on a state of deformation of the corresponding region of piezoionic polymer.

31. A method according to claim 30 wherein, for each overlap region, detecting the at least one electrical signal comprises detecting at least one of: a voltage difference between the one of the first plurality of electrodes and the one of the second plurality of electrodes; and a current flow between the one of the first plurality of electrodes and the one of the second plurality of electrodes.

* * * * *